United States Patent
Zhang et al.

(10) Patent No.: US 9,198,902 B2
(45) Date of Patent: Dec. 1, 2015

(54) 1,4-DIHYDROPYRIDINE-3,5-DICARBOXYLATE DERIVATIVES AND PREPARATION AND USE THEREOF

(75) Inventors: Hui Zhang, Jinan (CN); Mingwei Fan, Jinan (CN); Liang Sun, Jinan (CN)

(73) Assignee: Xuanzhu Pharma Co., Ltd., Jinan, Shandong Province (CN)

( * ) Notice: Subject to any disclaimer, the term of this patent is extended or adjusted under 35 U.S.C. 154(b) by 0 days.

(21) Appl. No.: 14/114,346

(22) PCT Filed: May 2, 2012

(86) PCT No.: PCT/CN2012/000577
§ 371 (c)(1),
(2), (4) Date: Oct. 28, 2013

(87) PCT Pub. No.: WO2012/146067
PCT Pub. Date: Nov. 1, 2012

(65) Prior Publication Data
US 2014/0045896 A1  Feb. 13, 2014

(30) Foreign Application Priority Data
Apr. 29, 2011 (CN) .......................... 2011 1 0109496

(51) Int. Cl.
C07D 401/14 (2006.01)
C07D 401/12 (2006.01)
C07D 417/14 (2006.01)
A61K 31/4439 (2006.01)
A61K 31/444 (2006.01)
A61K 45/06 (2006.01)
A61K 31/44 (2006.01)

(52) U.S. Cl.
CPC .............. *A61K 31/4439* (2013.01); *A61K 31/44* (2013.01); *A61K 31/444* (2013.01); *A61K 45/06* (2013.01); *C07D 401/12* (2013.01); *C07D 401/14* (2013.01); *C07D 417/14* (2013.01)

(58) Field of Classification Search
USPC ........................................ 514/340; 546/279.1
See application file for complete search history.

(56) References Cited

U.S. PATENT DOCUMENTS 4,639,522 A * 1/1987 Muto et al. ..................... 546/194

FOREIGN PATENT DOCUMENTS

| CN | 87107150 | 5/1988 |
| JP | H01139577 A | 6/1989 |
| WO | 2009056934 | 5/2009 |

OTHER PUBLICATIONS

Malhotra; Drugs, 2001, 61, 989-996.*
Haller; Int. J. Clin. Pract., 2008, 62, 781-790.*
English abstract of CN87107150A, May 4, 1988.
Burnier et al., "Treatment of essential hypertension with calcium channel blockers: what is the place of lercanidipine?", Expert Opinion on Drug Metabolism & Toxicology Aug. 2009, vol. 5, No. 8: 981-987.
Ertel et al., "Mibefradil (Ro 40/5967): the first selective T-type Ca2+ channel blocker", Expert Opin Investig Drugs. (1997);6(5):569-82.
Ge et al., "Combined L-/T-Type Calcium Channel Blockers: Ready for Prime Time", Hypertension. 2009;53:592-594, published online before print Feb. 23 2009, doi:10.1161/HYPERTENSIONAHA.108. 127548.
Lee et al., "Identification of T-Type 1H Ca2 Channels (Cav3.2) in Major Pelvic Ganglion Neurons", J Neurophysiol 87: 2844-2850, 2002; 10.1152/jn.00645.2001.
Tanaka, H. et al., "Efonidipine hydrochloride: a dual blocker of L- and T-type ca(2+) channels", Cardiovasc Drug Rev. 2002;20(1):81-92.
Tanaka, H. et al., "Pathophysiological significance of T-type Ca2+ channels: T-type Ca2+ channels and drug development", J Pharmacol Sci 2005; 99: 214-220.
Yamanaka, K. et al., "Antihypertensive effects of amlodipine, a new calcium antagonist", Nihon yakurigaku zasshi. Folia pharmacologica Japonica 97.2 (1991): 115-126 (abstract in English).
McManus et al., "Sulfamylurea Hypoglycemic Agents. I. Synthesis and Screening", J. Med. Chem., 1965, 8 (6), pp. 766-776.
Kobayashi et al., "Novel 2-amino-1, 4-dihydropyridine calcium antagonists. II: Synthesis and antihypertensive effects of 2-amino-1, 4-dihydropyridine derivatives having N, N-dialkylaminoalkoxycarbonyl groups at 3-and/or 5-position", Chemical and pharmaceutical bulletin 43.5 (1995): 797-817.

(Continued)

*Primary Examiner* — Janet L Andres
*Assistant Examiner* — Daniel Carcanague
(74) *Attorney, Agent, or Firm* — Kilpatrick Townsend & Stockton LLP

(57) ABSTRACT

The present invention relates to a 1,4-dihydropyridine-3,5-dicarboxylate compound of general compound (I), a process for preparing the same, a use thereof for the manufacture of a medicament for treating and/or preventing kidney injury, cardiovascular diseases and/or endocrine diseases, as well as a pharmaceutical composition and a pharmaceutical formulation containing said compounds, wherein the definitions of $R^1$, $R^2$, $R^3$, $R^4$, $R^5$, $R^6$, $R^7$, $R^8$, m, $n^1$, $n^2$, p and q are the same as those defined in the description.

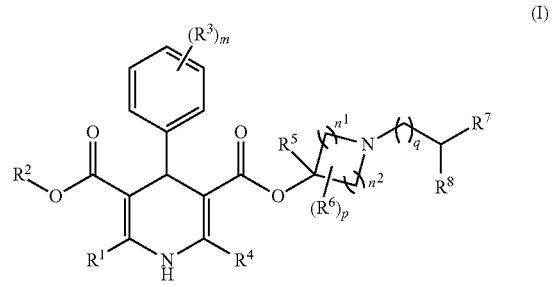

(I)

21 Claims, No Drawings

(56) References Cited

OTHER PUBLICATIONS

International Application No. PCT/CN2012/000577, "International Search Report" dated Jul. 26, 2012.
Shibanuma et al., "Synthesis of Optically Active 2-(N-Benzyl-N-methylamino)ethyl Methyl 2,6-Dimethyl-4-(m-nitrophenyl)-1,4-dihydropyridine-3,5-dicarboxylate (Nicardipine)", Chemical & Pharmaceutical Bulletin 28(9), 2809-2812, Sep. 25, 1980.
Office Action issued in corresponding JP Application No. 2014-506727, dated Dec. 24, 2014, 4 pages.

* cited by examiner

1,4-DIHYDROPYRIDINE-3,5-DICARBOXYLATE DERIVATIVES AND PREPARATION AND USE THEREOF

PRIOR RELATED APPLICATIONS

This application is a National Phase application of International Application No. PCT/CN2012/000577 filed May 2, 2012, which claims priority to Chinese Patent Application No. 201110109496.2 filed Apr. 29, 2011, each of which is incorporated herein by reference in its entirety.

TECHNICAL FIELD

The present invention is in the field of pharmaceutical technology, in particular relates to a 1,4-dihydropyridine-3,5-dicarboxylate compound, a process for preparing the same, a use thereof for the manufacture of a medicament for treating and/or preventing kidney injury, cardiovascular diseases and/or endocrine diseases, as well as a pharmaceutical composition and a pharmaceutical formulation containing said compounds.

INVENTION BACKGROUND

Dihydropyridine calcium ion channel blockers are agents for treating cardiovascular diseases since 1970s. They selectively block the $Ca^{2+}$ influx in the L-type or/and T-type calcium ion channels and reduce the intracellular $Ca^{2+}$ concentration by binding to protein receptor(s) so as to alter the cardiovascular function and exert a protective effect on heart and brain blood vessels. Dihydropyridine calcium ion channel blockers have high blood vessel selectivity, remarkable hypotensive effect, and wide applicability, and are therefore widely used clinically and become the first choice for the hypotensive agents.

Dihydropyridines are the most commonly used calcium ion channel blockers for treating high blood pressure. According to the duration of action and the pharmacological characteristics thereof, dihydropyridines can be divided into three generations (*Expert Opin. Drug Metab. Toxicol.* (2009) 5(8): 981-987). The first generation is the traditional short-acting blockers; and the representive agent is nifedipine. This kind of agents has a short duration time and a strong peripheral vasodilation effect, and causes facial flush, reflex tachycardia and peripheral edema. This kind of calcium ion channel blockers can produce a fast and substaintial hypotensive effect, and cause a large fluctuation in the blood pressure. Sometimes, it may increase the risk of the heart complication (e.g. myocardial infarction), and therefore has a remarkable negative effect on heart and increases the risk of heart attack for the hypertension patient. In addition, it may also cause reflective sympathetic excitation, resulting in the increase in myocardial oxygen consumption, and may easily induce arrhythmia and myocardial infarction. The second generation is the intermediate-acting blockers, which prolong the duration time of the blocking effect on the calcium ion channels and lower the acute vasodilation effect. One class is the sustained formulation of the first generation agents, and the representive agents include nifedipine controlled-release tablet (nifedipine GITS). Another class is the long-acting calcium ion channel blockers, and the representive agents include amlodipine. For this class of agents, the side effects caused by the acute vasodilation are almost disappeared, and the hypotensive effect lasts for more than 24 hours. The main side effect of the second generation agents is the peripheral edema caused by the continous peripheric vasodilation. The aim for the calcium ion channel blockers of the third generation is to maintain the long-acting hypotensive effect, while further descrease the occurrence of peripheral edema. The representive agents include barnidipine, lercanidipine, manidipine and the like. In comparison with amlodipine, this kind of agents has a longer acting effect and an increase in tolerance.

As the development in the L-type calcium ion channel blockers, both the pharmacological activity and the pharmacokinetic characterics of calcium ion channel blockers have been improved. However, the various side effects caused by the long term administration have not been overcome yet.

It was found in research that the T-type calcium ion channels are expressed in various arteries and veins. Being different from the L-type calcium ion channels, the T-type calcium ion channels participate in the adjust of the microcirculation, which has an important role in adjusting blood pressure, renal perfusion and coronary flow (*J Pharmacol Sci* (2005) 99: 214-220). In the renal microcirculation, the L-type calcium ion channels are mainly located in afferent glomerular arteriole, and the inhibition on the activity of L-type calcium ion channels can easily cause the side effect of vascular dilated edema. However, the T-type calcium ion channels are located in both afferent glomerular arteriole and efferent glomerular arteriole, and the inhibition on the T-type calcium ion channels can improve the microcirculation through the balanced hydrostatics, increase the glomerular filtration rate and decrease the vascular dilated edema without an influence on the glomerular internal pressure, and therefore have a long-term protective effect on kidney. On the other hand, the T-type calcium ion channel blockers can also adjust heart beat and regulate blood flow rate, and therefore have a protective effect on heart.

The L-type and T-type dual calcium ion channel blockers have the functions of decreasing the blood pressure, slowing down the tachycardia, and reducing the edema occurrence, and therefore have a protective effect on heart and kidney (*Hypertension.* 2009; 53: 592-594). It is found in the clinical research that the L-type and T-type dual calcium ion channel blocker mibefradil is an effective hypotensive and antiischemic agent. It can reduce the side effects caused by the conventional calcium ion channel blockers, relax the vascular smooth muscle, reduce the heart rate without decreasing the myocardial contractile force, and improve the heart function (*Exp. Opin. Invest. Drugs* (1997) 6(5): 569-582). The therapeutical effects of mibefradil and the L-type and T-type dual calcium ion channel blocker efonidipine further demonstrated the above inference (*Cardiovascular Drug Reviews,* 2002, 20(1):81-92). However, due to the drug interaction, mibefradil was withdrawn from the market less than one year after it was put into the market. Therefore, it is clinically urgent to develop compounds having better safety and dual blocking effects on L-type and T-type calcium ion channels. The blocking effect on both L-type calcium ion channels and T-type calcium ion channels can not only provide the utility of treating high blood pressure and solve the side effects that are insuperable for the L-type calcium ion channel blockers, but also exert the protective effect on heart and kidney.

SUMMARY OF INVENTION

Based on the aim of developing superordinary agents having hypotensive effect and protective effect on heart and kidney, the present inventors have found a class of 1,4-dihydropyridine-3,5-dicarboxylate derivatives having remarkable hypotensive effect, being capable of maintaining the hypotensive effect for a long time, and having dual blocking effects on L-type and T-type calcium ion channels through extensive experiments, and therefore accomplished the present invention.

Thus, the present invention provides a compound represented by the following general formula (I), and a pharmaceutically acceptable salt and a stereoisomer thereof:

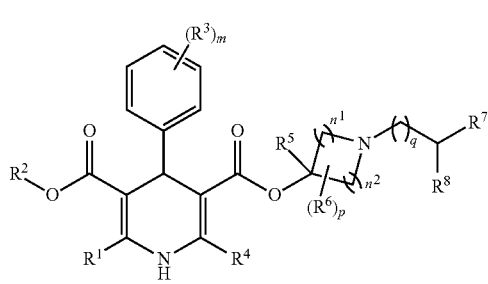

wherein:
$R^1$ and $R^4$ are each independently selected from amino, cyano, and $C_{1-6}$alkyl, $C_{1-4}$alkoxy$C_{1-3}$alkyl, $C_{2-6}$alkenyl or $C_{2-6}$alkynyl that is unsubstituted or substituted by 1-3 $Q^1$ substituents, and the carbon atom(s) therein can be optionally (i.e. non-compulsively) replaced with 1-3 groups from O, $S(O)_x$, $N(H)_x$, $NCH_3$ or $C(O)$, wherein x is selected from 0, 1 or 2; $Q^1$ is selected from halogen, hydroxy, amino, cyano, carboxyl and $C_{1-6}$alkoxy;
$R^2$ is selected from $C_{1-6}$alkyl, $C_{3-8}$cycloalkyl$C_{0-6}$alkyl or 3-8 membered heterocyclyl$C_{0-6}$alkyl that is unsubstituted or substituted by 1-3 $Q^2$ substituents, $Q^2$ is selected from halogen, hydroxy, amino, $C_{1-6}$alkyl, $C_{1-6}$alkoxy, and $C_{1-6}$alkyl and $C_{1-6}$alkoxy that are substituted with 1-3 halogen atoms;
$R^3$ is selected from hydrogen, halogen, hydroxy, cyano, nitro and $C_{1-6}$alkylamido;
$R^5$ and $R^6$ are each independently selected from $C_{1-6}$alkyl or $C_{3-8}$cycloalkyl$C_{0-6}$alkyl that is unsubstituted or substituted by 1-3 $Q^3$ substituents, $Q^3$ is selected from halogen, hydroxy, amino and $C_{1-6}$alkoxy;
$R^7$ and $R^8$ are each independently selected from hydrogen, $C_{1-6}$alkyl, aryl$C_{0-6}$alkyl that is unsubstituted or substituted by 1-3 $Q^4$ substituents, and 3-8 membered heterocyclyl$C_{0-6}$alkyl that is unsubstituted or substituted by 1-3 $Q^4$ substituents, and $R^7$ and $R^8$ are not both hydrogen at the same time, $Q^4$ is selected from halogen, hydroxy, cyano, nitro, amino, $C_{1-6}$alkyl, $C_{1-6}$alkyl substituted by 1-3 halogen atoms, $C_{1-6}$alkoxy and $C_{1-6}$alkylamido;
m is selected from 1, 2 or 3, when m is 2 or 3, $R^3$ can be identical or different;
$n^1$ and $n^2$ are each independently selected from an integer of 1-5, and $n^1$ and $n^2$ are not both 2, 4 and 5 at the same time; and
p and q are each independently selected from 0, 1, 2 or 3, but when q is 0, $R^7$ and $R^8$ are not both phenyl at the same time.

The present invention also provides a pharmaceutical composition and a pharmaceutical formulation containing the compound of general formula (I) or a pharmaceutically acceptable salt thereof or a stereoisomer thereof.

The present invention also provides the compound of general formula (I) or a pharmaceutically acceptable salt thereof or a stereoisomer thereof, or a pharmaceutical composition containing the compound of general formula (I) or a pharmaceutically acceptable salt thereof or a stereoisomer thereof, as a medicament for treating and/or preventing kidney injury, cardiovascular diseases and/or endocrine diseases.

The present invention also provides the use of the compound of general formula (I) or a pharmaceutically acceptable salt thereof or a stereoisomer thereof, or a pharmaceutical composition containing the compound of general formula (I) or a pharmaceutically acceptable salt thereof or a stereoisomer thereof in the manufacture of a medicament for treating and/or preventing kidney injury, cardiovascular diseases and/or endocrine diseases.

The present invention also provides a method for treating and/or preventing kidney injury, cardiovascular diseases and/or endocrine diseases, comprising the step of administrating an effective amount of the compound of general formula (I) or a pharmaceutically acceptable salt thereof or a stereoisomer thereof, or a pharmaceutical composition containing the compound of general formula (I) or a pharmaceutically acceptable salt thereof or a stereoisomer thereof to a subject in need thereof.

The present invention also provides a process for preparing the compound of general formula (I), comprising the following steps:

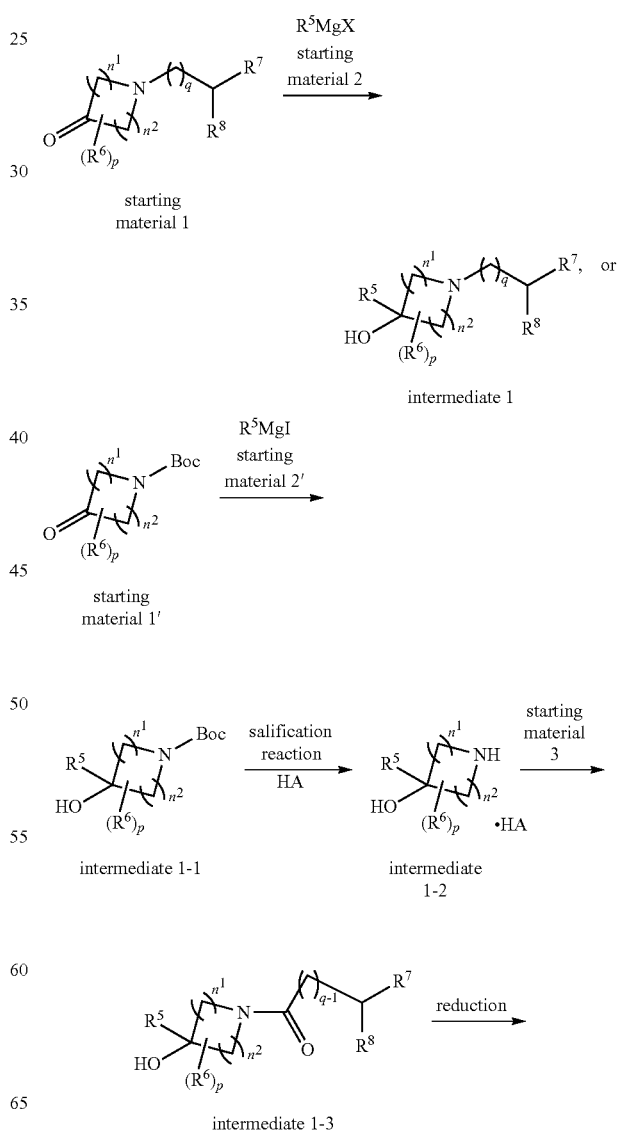

-continued

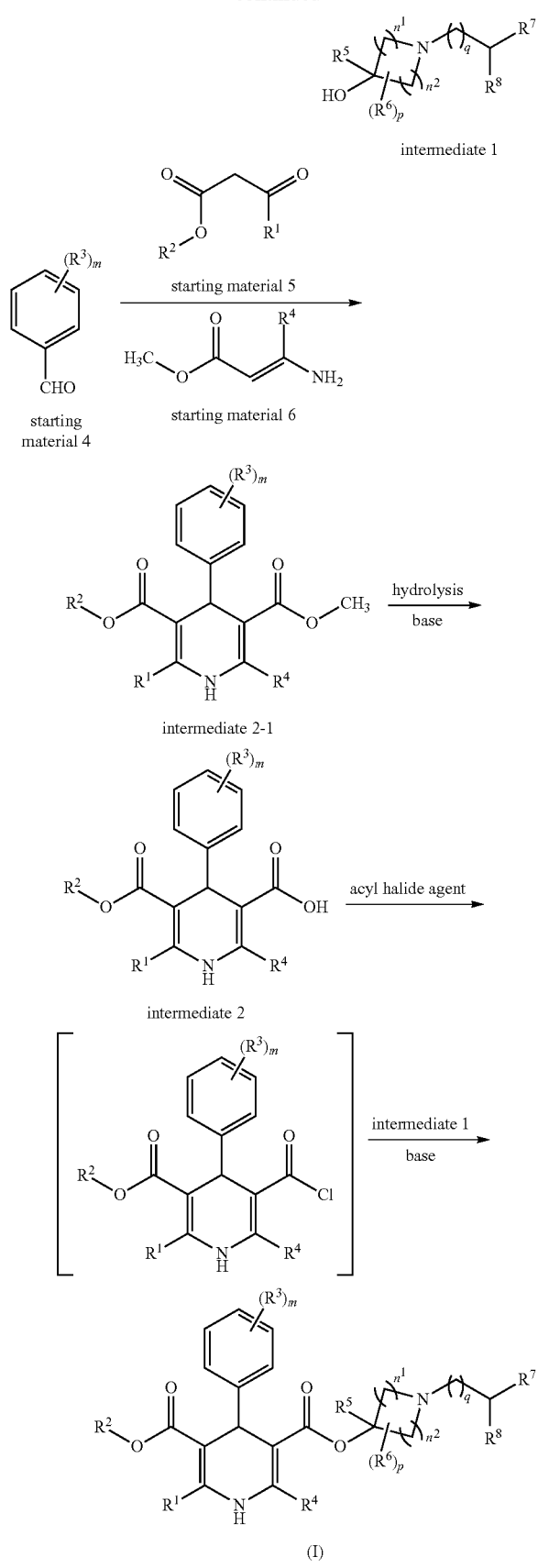

intermediate 1 intermediate 2-1 intermediate 2

(I)

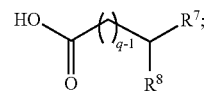

wherein $R^1$, $R^2$, $R^3$, $R^4$, $R^5$, $R^6$, $R^7$, $R^8$, m, $n^1$, $n^2$, p and q are as defined hereinbefore; starting material 2=$R^5$MgX, wherein X is Br or I; starting material 2'=$R^5$MgI, starting material 5

Step 1: Preparation of Intermediate 1

Method 1:
Starting material 1 and starting material 2 (Grignard reagent) are subjected to a nucleophilic substitution reaction at a low temperature such as from −30 to −10° C. to produce intermediate 1.

Method 2:
Starting material 1' and starting material 2' (Grignard reagent) are subjected to a nucleophilic substitution reaction to produce intermediate 1-1, which is subjected to a salification reaction with HA (an acid, being a conventional inorganic or organic acid, such as hydrochloric acid, nitric acid, sulfuric acid, acetic acid, formic acid, maleic acid, tartaric acid, methanesulfonic acid or fumaric acid, and the like) to produce intermediate 1-2; the resulting intermediate 1-2 and starting material 3 are subjected to a coupling reaction to produce intermediate 1-3; and then intermediate 1-3 is reduced with a reductant (e.g. a hydride ion reductant such as $LiAlH_4$ and $NaBH_4$, and the like) to produce intermediate 1.

Step 2: Preparation of Intermediate 2

Starting material 4, starting material 5 and starting material 6 are subjected to a condensation reaction under reflux in an organic solvent (e.g. an alcohol solvent such as ethanol, methanol, isopropanol, butanol, ethylene glycol, and the like) to produce intermediate 2-1, which is hydrolyzed in the presence of a base (e.g. NaOH, and $NaHCO_3$, and the like) to produce intermediate 2.

Step 3: Preparation of a Compound of Forumla (I)

Intermediate 2 and an acyl halide agent (e.g. thionyl chloride, acryloyl chloride, and the like) are reacted at a low temperature such as from −40 to −10° C. Then the resulting material and intermediate 1 are subject to a hydrolyzation reaction under a basic condition (e.g. in the presence of sodium bicarbonate, sodium hydroxide, and the like) at a low temperature such as from −40 to −10° C. to produce the compound of formula (I).

In the present invention, the term "halogen" means fluoro, chloro, bromo or iodo.

In the present invention, the term "$C_{1-6}$alkyl" means a straight-chain or branched chain alkyl containing 1-6 carbon atoms, preferably $C_{1-4}$alkyl, such as $C_{2-4}$alkyl, $C_{2-3}$alkyl, $C_{1-3}$alkyl, $C_{1-2}$alkyl; its example includes but is not limited to, e.g., methyl, ethyl, n-propyl, isopropyl, n-butyl, isobutyl, sec-butyl, tert-butyl, n-pentyl, isopentyl, 2-methylbutyl, neopentyl, 1-ethylpropyl, n-hexyl, 4-methylpentyl, 3-methylpentyl, 2-methylpentyl, 1-methylpentyl, 3,3-dimethyl butyl, 2,2-dimethylbutyl, 1,1-dimethyl butyl, 1,2-dimethyl butyl, 1,3-dimethyl butyl, 2,3-dimethyl butyl, 2-ethylbutyl, 1,2-dimethylpropyl, and the like.

In the present invention, the term "$C_{0-6}$alkyl" means a straight-chain or branched chain alkyl containing 0-6 carbon atoms, or means a bond when the carbon atom number is zero; preferably $C_{0-4}$alkyl, e.g. $C_{0-3}$alkyl, most preferably $C_{0-2}$alkyl.

In the present invention, the term "$C_{3-8}$cycloalkyl" means a monovalent cyclic alkyl derived from an alkane moiety of 3-8 carbon atoms by removing one hydrogen atom, preferably $C_{3-7}$cycloalkyl, e.g. $C_{5-7}$cycloalkyl, $C_{3-6}$cycloalkyl, $C_{5-6}$cycloalkyl, and the like; its example includes but is not limited to, e.g., cyclopropyl, cyclobutyl, 1-methylcyclobutyl, cyclopentyl, cyclohexyl, cycloheptyl, cyclooctyl, and the like.

In the present invention, the term "$C_{1-6}$alkoxy" means a "$C_{1-6}$alkyl" group attached to another structure via an oxygen atom, preferably $C_{1-4}$alkoxy, such as $C_{1-3}$alkoxy, $C_{1-2}$alkoxy, and the like; its example includes but is not limited to, e.g., methoxy, ethoxy, propoxy, isopropoxy, butoxy, isobutoxy, tert-butoxy, sec-butoxy, pentoxy, neo-pentoxy, hexoxy, and the like.

In the present invention, the term "$C_{2-6}$alkenyl" means a straight-chain, brached chain or cyclic hydrocarbonyl containing 2-6 carbon atoms and double bond(s), preferably $C_{2-4}$alkenyl, e.g. ethenyl, 1-propenyl, 2-propenyl, 1-butenyl, 2-butenyl, 1-pentenyl, 2-pentenyl, 3-pentenyl, 1-hexenyl, 2-hexenyl, 3-hexenyl, cyclopropenyl, cyclopentenyl, cyclohexenyl, and the like.

In the present invention, the term "$C_{2-6}$alkynyl" means a straight-chain, brached chain or cyclic alkynyl containing 2-6 carbon atoms and triple bond(s), preferably $C_{2-4}$alkynyl, e.g., ethynyl, propynyl, 2-butynyl, 2-pentynyl, 3-pentynyl, 2-hexynyl, 3-hexynyl, cyclopropynyl, cyclobutynyl, cyclopentynyl, cyclohexynyl, and the like.

In the present invention, the term "$C_{1-6}$alkylamido" means a "$C_{1-6}$alkyl-CO—NH—" group.

In the present invention, the term "aryl" means a 6-10 membered monocyclic or bicyclic aromatic hydrocarbon cyclic radical, e.g. phenyl, naphthyl, and the like.

In the present invention, the term "3-8 membered heterocyclyl" means a 3-8 membered saturated or unsaturated cyclic group containing one or more heteroatoms selected from N, O or S, e.g., 3-6 membered heterocyclyl, and the like, more preferably 5-6 membered heterocyclyl; its example includes but is not limited to, e.g., oxiranyl, dioxiranyl, thiiranyl, aziridinyl, 2H-aziridinyl, diaziridinyl, 3H-diazirinyl, oxaziridinyl, oxetanyl, 1,2-dioxetanyl, thietanyl, 1,2-dithietyl, azetidinyl, 1,2-diazetidinyl, azacyclobutadienyl, 1,2-diazacyclobutenyl, furyl, tetrahydrofuryl, thienyl, 2,5-dihydrothienyl, tetrahydrothienyl, pyrrolyl, dihydropyrrolyl, pyrrolidinyl, 1,3-dioxolanyl, 1,3-dioxole-2-one group, 1,2-dithiolenyl, 1,3-dithiolanyl, imidazolyl, 4,5-dihydroimidazolyl, imidazolidinyl, pyrazolyl, 4,5-dihydropyrazolyl, pyrazolidinyl, oxazolyl, 4,5-dihydrooxazolyl, isoxazolyl, 4,5-dihydroisoxazolyl, 2,3-dihydroisoxazolyl, 1,2,3-oxadiazolyl, 1,2,5-oxadiazolyl, thiazolyl, 4,5-dihydrothiazolyl, isothiazolyl, 1,2,3-thiadiazolyl, 1,2,4-thiadiazolyl, 1,3,4-thiadiazolyl, 1,2,3-triazolyl, 1,2,4-triazolyl, tetrazolyl, 2H-pyranyl, 2H-pyran-2-one group, 3,4-dihydro-2H-pyranyl, 4H-pyranyl, tetrahydropyranyl, 4H-pyran-4-one group, pyridyl, 2-pyridonyl, 4-pyridonyl, hydropyridonyl, piperidyl, 1,4-dioxinyl, 1,4-dithiinyl, 1,4-oxathiinyl, 1,4-dioxanyl, 1,3-dioxanyl, 1,3-oxathianyl, 2H-1,2-oxazinyl, 4H-1,2-oxazinyl, 6H-1,2-oxazinyl, 2H-1,3-oxazinyl, 4H-1,3-oxazinyl, 6H-1,3-oxazinyl, 2H-1,4-oxazinyl, 4H-1,4-oxazinyl, 5,6-dihydro-4H-1,3-oxazinyl, morpholinyl, 2H-1,3-thiazinyl, 4H-1,3-thiazinyl, 5,6-dihydro-4H-1,3-thiazinyl, 6H-1,3-thiazinyl, 2H-1,4-thiazinyl, 4H-1,4-thiazinyl, pyridazinyl, pyrimidinyl, pyrazinyl, piperazinyl, 1,2,3-triazinyl, 1,2,4-triazinyl, 1,3,5-triazinyl, 1,2,4,5-tetrazinyl, oxepinyl, thiepinyl, 1,4-dioxocinyl, azepinyl, 1,2-diazepinyl, 1,3-diazepinyl, 1,4-diazepinyl, azocinyl, 1,4-dihydro-1,4-diazocinyl, and the like. The saturated heterocyclyl is preferably, for example, aziridinyl, azetidinyl, pyrrolidinyl, imidazolidinyl, pyrazolidinyl, hydropyridonyl, piperidyl, piperazinyl, oxiranyl, tetrahydrofuryl, tetrahydrothienyl, 1,3-dioxolanyl, 1,3-dithiolanyl, tetrahydropyranyl, 1,4-dioxanyl, 1,3-dioxanyl, 1,3-oxathianyl, oxaziridinyl, morpholinyl, and the like; and the unsaturated heterocyclyl is preferably, for example, pyridyl, furyl, thienyl, pyrrolyl, oxazolyl, thiazolyl, and thiadiazolyl, and the like.

In a preferable embodiment of the compound of general formula (I) of the present invention, $R^1$ and $R^4$ are each independently selected from amino, cyano, and $C_{1-4}$alkyl, $C_{1-3}$alkoxy$C_{1-2}$alkyl, $C_{2-4}$alkenyl and $C_{2-4}$alkynyl that are unsubstituted or substituted by $Q^1$ substituent, and the carbon atom(s) therein can be non-compulsively replaced with O, $S(O)_x$, $N(H)_x$, $NCH_3$ or $C(O)$, wherein x is selected from 0, 1 or 2; $Q^1$ is selected from halogen, hydroxy, amino, carboxyl and $C_{1-4}$alkoxy.

In a further preferable embodiment of the compound of general formula (I) of the present invention, $R^1$ and $R^4$ are each independently selected from amino, cyano, and $C_{1-4}$alkyl and $C_{1-3}$alkoxy$C_{1-2}$alkyl that are unsubstituted or substituted by $Q^1$ substituent, and the carbon atom(s) therein can be non-compulsively replaced with O, $N(H)_x$ or $C(O)$, wherein x is selected from 0, 1 or 2; $Q^1$ is selected from halogen, hydroxy, amino and $C_{1-4}$alkoxy.

In a preferable embodiment of the compound of general formula (I) of the present invention, $R^2$ is selected from $C_{1-4}$alkyl, $C_{3-6}$cycloalkyl$C_{0-4}$alkyl or 3-6 membered saturated heterocyclyl$C_{0-4}$alkyl that is unsubstituted or substituted by $Q^2$ substituent, $Q^2$ is selected from halogen, hydroxy, amino, $C_{1-4}$alkyl, $C_{1-4}$alkoxy, and $C_{1-4}$alkyl and $C_{1-4}$alkoxy that are substituted by halogen.

In a further preferable embodiment of the compound of general formula (I) of the present invention, $R^2$ is selected from $C_{1-4}$alkyl, $C_{3-6}$cycloalkyl$C_{0-2}$alkyl or 5-6 membered saturated heterocyclyl$C_{0-2}$alkyl that is unsubstituted or substituted by $Q^2$ substituent, $Q^2$ is selected from fluoro, chloro, hydroxy, amino, $C_{1-4}$alkyl, $C_{1-4}$alkoxy, and $C_{1-4}$alkyl and $C_{1-4}$alkoxy that are substituted by fluoro and/or chloro.

In a preferable embodiment of the compound of general formula (I) of the present invention, $R^3$ is selected from hydrogen, halogen, hydroxy, cyano, nitro or $C_{1-4}$alkylamido.

In a further preferable embodiment of the compound of general formula (I) of the present invention, $R^3$ is selected from hydrogen, halogen or nitro.

In a preferable embodiment of the compound of general formula (I) of the present invention, $R^5$ and $R^6$ are each independently selected from $C_{1-4}$alkyl or $C_{3-6}$cycloalkyl$C_{0-4}$alkyl that is unsubstituted or substituted by $Q^3$ substituent, $Q^3$ is selected from halogen, hydroxy, amino and $C_{1-4}$alkoxy.

In a further preferable embodiment of the compound of general formula (I) of the present invention, $R^5$ and $R^6$ are each independently selected from $C_{1-4}$alkyl or $C_{3-6}$cycloalkyl$C_{0-2}$alkyl that is unsubstituted or substituted by $Q^3$ substituent, $Q^3$ is selected from halogen, hydroxy, amino and $C_{1-2}$alkoxy.

In a preferable embodiment of the compound of general formula (I) of the present invention, $R^7$ and $R^8$ are each independently selected from hydrogen, $C_{1-4}$alkyl, aryl$C_{0-4}$alkyl that is unsubstituted or substituted by $Q^4$ substituent, and 3-6 membered heterocyclyl$C_{0-4}$alkyl that is unsubstituted or substituted by $Q^4$ substituent, $Q^4$ is selected from halogen, hydroxy, amino, $C_{1-4}$alkyl, and $C_{1-4}$alkyl that are substituted by halogen, and $C_{1-4}$alkoxy.

In a further preferable embodiment of the compound of general formula (I) of the present invention, $R^7$ and $R^8$ are each independently selected from hydrogen, $C_{1-4}$alkyl, aryl$C_{0-2}$alkyl that is unsubstituted or substituted by $Q^4$ substituent, or 5-6 membered heterocyclyl$C_{0-2}$alkyl that is unsubstituted or substituted by $Q^4$ substituent, $Q^4$ is selected from halogen, hydroxy, amino, $C_{1-3}$alkyl, and $C_{1-3}$alkyl that are substituted by halogen, and $C_{1-3}$alkoxy.

In a preferable embodiment of the compound of general formula (I) of the present invention, m is 1 or 2.

In a preferable embodiment of the compound of general formula (I) of the present invention, $n^1$ and $n^2$ are each independently selected from 1, 2 or 3, in particular 1 or 2.

In another preferable embodiment of the compound of general formula (I) of the present invention,
$R^1$ and $R^4$ are each independently selected from amino, cyano, $C_{1-4}$alkyl, $C_{1-3}$alkoxy$C_{1-2}$alkyl, $C_{2-4}$alkenyl or $C_{2-4}$alkynyl that is unsubstituted or substituted by 1-3 $Q^1$ substituents, and the carbon atom(s) therein can be optionally replaced with 1-3 groups from O, S(O)$_x$, N(H)$_x$, NCH$_3$ or C(O), wherein x is selected from 0, 1 or 2; $Q^1$ is selected from halogen, hydroxy, amino, carboxyl and $C_{1-4}$alkoxy;
$R^2$ is selected from $C_{1-4}$alkyl, $C_{3-6}$cycloalkyl$C_{0-4}$alkyl or 3-6 membered saturated heterocyclyl$C_{0-4}$alkyl that is unsubstituted or substituted by 1-3 $Q^2$ substituents, $Q^2$ is selected from halogen, hydroxy, amino, $C_{1-4}$alkyl, $C_{1-4}$alkoxy, and $C_{1-4}$alkyl and $C_{1-4}$alkoxy that are substituted by 1-3 halogen atoms;
$R^7$ and $R^8$ are each independently selected from hydrogen, $C_{1-4}$alkyl, aryl$C_{0-4}$alkyl that is unsubstituted or substituted by 1-3 $Q^4$ substituents, and 3-8 membered heterocyclyl$C_{0-4}$alkyl that is unsubstituted or substituted by 1-3 $Q^4$ substituents, and $R^7$ and $R^8$ are not both hydrogen at the same time, $Q^4$ is selected from halogen, hydroxy, amino, $C_{1-4}$alkyl, and $C_{1-4}$alkyl that are substituted by 1-3 halogen atoms and $C_{1-4}$alkoxy;
m is selected from 1, 2 or 3, when m is 2 or 3, $R^3$ can be identical or different;
$n^1$ and $n^2$ are each independently selected from an integer of 1-4, and $n^1$ and $n^2$ are not both 2 and 4 at the same time; and
p and q are each independently selected from 0, 1, 2 or 3, but when q is 0, $R^7$ and $R^8$ are not both phenyl at the same time.

In another preferable embodiment of the compound of general formula (I) of the present invention,
$R^1$ and $R^4$ are each independently selected from amino, cyano, and $C_{1-4}$alkyl and $C_{1-3}$alkoxy$C_{1-2}$alkyl that are unsubstituted or substituted by 1-3 $Q^1$ substituents, and the carbon atom(s) therein can be optionally replaced with 1-3 groups from O, N(H)$_x$ or C(O), wherein x is selected from 0, 1 or 2; $Q^1$ is selected from halogen, hydroxy, amino and $C_{1-4}$alkoxy;
$R^2$ is selected from $C_{1-4}$alkyl, cyclopropyl, cyclopropylmethyl, cyclopropylethyl, azetidinyl, pyrrolidinyl, piperidyl, morpholinyl, piperazinyl, pyrrolidinylmethyl and morpholinylmethyl that are unsubstituted or substituted by 1-3 $Q^2$ substituents, wherein $Q^2$ is selected from fluoro, chloro, hydroxy, amino, $C_{1-4}$alkyl, $C_{1-4}$alkoxy, and $C_{1-4}$alkyl and $C_{1-4}$alkoxy that are substituted by 1-3 fluoro and/or chloro atoms;
$R^3$ is selected from hydrogen, halogen and nitro;
$R^5$ and $R^6$ are each independently selected from $C_{1-4}$alkyl or $C_{3-6}$cycloalkyl$C_{0-2}$alkyl that is unsubstituted or substituted by 1-3 $Q^3$ substituents, $Q^3$ is selected from halogen, hydroxy, amino and $C_{1-2}$alkoxy;
$R^7$ and $R^8$ are each independently selected from hydrogen, methyl, ethyl, aryl$C_{0-2}$alkyl that is unsubstituted or substituted by 1-3 $Q^4$ substituents, and 3-6 membered heterocyclyl$C_{0-2}$alkyl that is unsubstituted or substituted by 1-3 $Q^4$ substituents, and $R^7$ and $R^8$ are not both hydrogen at the same time, $Q^4$ is selected from halogen, hydroxy, amino, $C_{1-3}$alkyl, and $C_{1-3}$alkyl that are substituted by 1-3 halogen atoms, and $C_{1-3}$alkoxy;
m is each independently selected from 1, 2 or 3, when m is 2 or 3, $R^3$ can be identical or different;
$n^1$ and $n^2$ are each independently selected from 1, 2 or 3, and $n^1$ and $n^2$ are not both 2 at the same time; and
p and q are each independently selected from 0, 1, 2 or 3, but when q is 0, $R^7$ and $R^8$ are not both phenyl at the same time.

In another preferable embodiment of the compound of general formula (I) of the present invention,
$R^1$ and $R^4$ are each independently selected from methyl, ethyl and ethoxymethyl that are unsubstituted or substituted by 1-3 $Q^1$ substituents, and the carbon atom(s) therein can be optionally replaced with 1-3 groups from O, N(H)$_x$ or C(O), wherein x is selected from 1 or 2; $Q^1$ is selected from halogen, hydroxy, amino, methoxy and ethoxy;
$R^2$ is selected from methyl, ethyl, isopropyl, cyclopropyl, cyclopropylmethyl, azetidinyl, pyrrolidinyl, piperidyl, morpholinyl, pyrrolidinylmethyl and morpholinylmethyl that are unsubstituted or substituted by 1-3 $Q^2$ substituents, $Q^2$ is selected from fluoro, chloro, hydroxy, amino, $C_{1-4}$alkyl, $C_{1-4}$alkoxy, and $C_{1-4}$alkyl and $C_{1-4}$alkoxy that are substituted by 1-3 fluoro and/or chloro atoms;
$R^3$ is selected from hydrogen, fluoro, chloro and nitro;
$R^5$ and $R^6$ are each independently selected from methyl or ethyl that is unsubstituted or substituted by 1-3 $Q^3$ substituents, wherein $Q^3$ is selected from fluoro, chloro, hydroxy, amino, methoxy and ethoxy;
$R^7$ and $R^8$ are each independently selected from hydrogen, methyl, ethyl, and phenyl$C_{0-2}$alkyl, pyridyl$C_{0-2}$alkyl, furyl$C_{0-2}$alkyl, thienyl$C_{0-2}$alkyl, pyrrolyl$C_{0-2}$alkyl, thiazolyl$C_{0-2}$alkyl and thiadiazolyl$C_{0-2}$alkyl that are unsubstituted or substituted by 1-3 $Q^4$ substituents, and $R^7$ and $R^8$ are not both hydrogen at the same time, $Q^4$ is selected from fluoro, chloro, hydroxy, amino, methyl, ethyl, fluoromethyl, difluoromethyl, trifluoromethyl, methoxy and ethoxy;
m is selected from 1, 2 or 3, when m is 2 or 3, $R^3$ can be identical or different;
$n^1$ is 1, 2 or 3, $n^2$ is 1;
p and q are each independently selected from 0, 1, 2 or 3, when q is 0, $R^7$ and $R^8$ are not both phenyl at the same time.

In another preferable embodiment of the compound of general formula (I) of the present invention,
$R^1$ and $R^4$ are each independently selected from methyl, ethyl or ethoxymethyl that are unsubstituted or substituted by 1-3 $Q^1$ substituents, $Q^1$ is selected from fluoro, chloro, amino, methoxy or ethoxy;
$R^2$ is selected from methyl or ethyl that are unsubstituted or substituted by 1-3 $Q^2$ substituents, $Q^2$ is selected from fluoro, chloro, methyl, methoxy, or methoxy and ethoxy that are substituted by 1-3 fluoro, chloro atoms;
$R^3$ is selected from hydrogen, chloro or nitro;
$R^5$ is selected from methyl or ethyl that are unsubstituted or substituted by 1-3 $Q^3$ substituents, $Q^3$ is selected from fluoro, chloro, hydroxy or amino;
$R^6$ is selected from methyl that is unsubstituted or substituted by 1-3 $Q^3$ substituents, $Q^3$ is selected from fluoro, chloro, hydroxy or amino;
$R^7$ and $R^8$ are each independently selected from hydrogen, and phenyl, benzyl, pyridyl, furyl, thienyl, thiazolyl or pyrrolyl that are unsubstituted or substituted by 1-3 $Q^4$ substituents, and $R^7$ and $R^8$ are not both hydrogen at the same time, $Q^4$ is selected from fluoro, chloro, hydroxy, amino, methyl, trifluoromethyl or methoxy;
m is 1;
$n^1$ is 1 or 2, $n^2$ is 1;
p and q is each independently selected from 0, 1 or 2, when q is 0, $R^7$ and $R^8$ are not both phenyl at the same time.

In the present invention, the specific preferable compounds of general formula (I) include the following compounds and pharmaceutically acceptable salts thereof and stereoisomers thereof:

| Compound | Structure | Chemical Name |
|---|---|---|
| 1 | 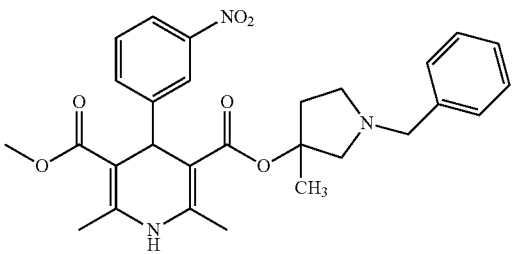 | 3-(1-benzyl-3-methylpyrrolidin-3-yl) 5-methyl 2,6-dimethyl-4-(3-nitrophenyl)-1,4-dihydropyridine-3,5-dicarboxylate |
| 2 | 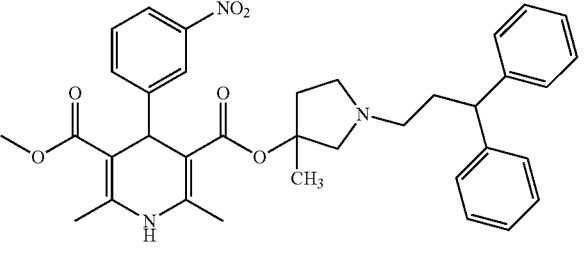 [SMILES: COC(=O)C1=C(C)NC(C)=C(C(=O)OC2(C)CCN(CCC(c3ccccc3)c3ccccc3)C2)C1c1cccc([N+](=O)[O-])c1] | 3-[1-(3,3-diphenylpropyl)-3-methylpyrrolidin-3-yl] 5-methyl 2,6-dimethyl-4-(3-nitrophenyl)-1,4-dihydropyridine-3,5-dicarboxylate |
| 3 | 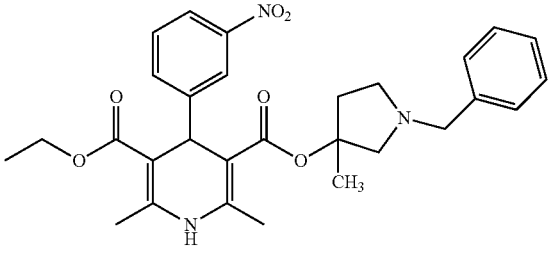 | 3-(1-benzyl-3-methylpyrrolidin-3-yl) 5-ethyl 2,6-dimethyl-4-(3-nitrophenyl)-1,4-dihydropyridine-3,5-dicarboxylate |
| 4 | 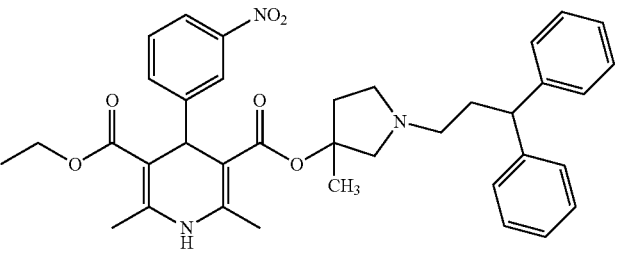 | 3-[1-(3,3-diphenylpropyl)-3-methylpyrrolidin-3-yl] 5-ethyl 2,6-dimethyl-4-(3-nitrophenyl)-1,4-dihydropyridine-3,5-dicarboxylate |
| 5 | 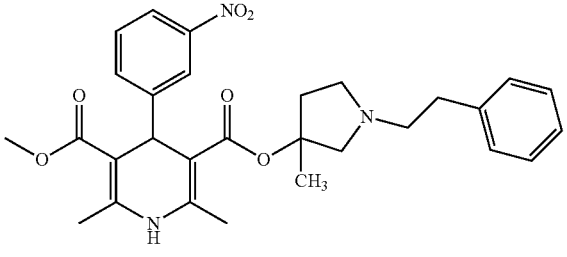 [SMILES: COC(=O)C1=C(C)NC(C)=C(C(=O)OC2(C)CCN(CCc3ccccc3)C2)C1c1cccc([N+](=O)[O-])c1] | 3-(1-phenylethyl-3-methylpyrrolidin-3-yl) 5-methyl 2,6-dimethyl-4-(3-nitrophenyl)-1,4-dihydropyridine-3,5-dicarboxylate |

-continued

| Compound Structure | Chemical Name |
|---|---|
| 6 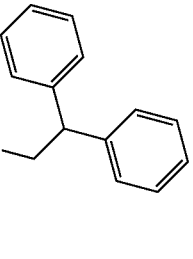 | 3-[1-(2,2-diphenylethyl)-3-methylpyrrolidin-3-yl] 5-methyl 2,6-dimethyl-4-(3-nitrophenyl)-1,4-dihydropyridine-3,5-dicarboxylate |
| 7 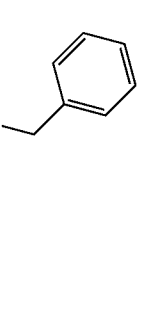 | 3-(1-benzyl-3-methylpyrrolidin-3-yl) 5-methyl 2-[(2-aminoethoxy)methyl]-4-(2-chlorophenyl)-6-methyl-1,4-dihydropyridine-3,5-dicarboxylate |
| 8 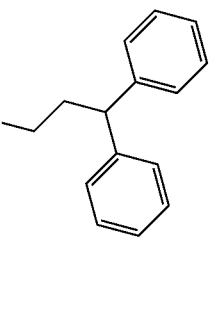 | 3-[1-(3,3-diphenylpropyl)-3-methylpyrrolidin-3-yl] 5-methyl 2-[(2-aminoethoxy)methyl]-4-(2-chlorophenyl)-6-methyl-1,4-dihydropyridine-3,5-dicarboxylate |
| 9 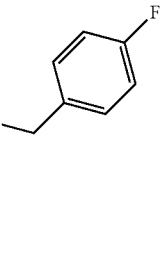 | 3-[1-(4-fluorobenzyl)-3-methylpyrrolidin-3-yl] 5-methyl 2,6-dimethyl-4-(3-nitrophenyl)-1,4-dihydropyridine-3,5-dicarboxylate |
| 10 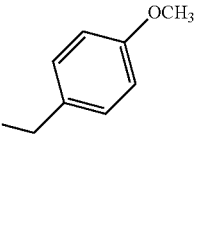 | 3-[1-(4-methoxybenzyl)-3-methylpyrrolidin-3-yl] 5-methyl 2,6-dimethyl-4-(3-nitrophenyl)-1,4-dihydropyridine-3,5-dicarboxylate |

-continued

| Compound | Structure | Chemical Name |
|---|---|---|
| 11 | 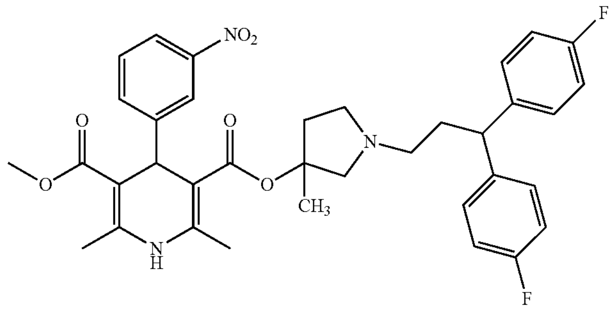 | 3-[1-(3,3-bis(4-fluorophenyl)propyl)-3-methylpyrrolidin-3-yl] 5-methyl 2,6-dimethyl-4-(3-nitrophenyl)-1,4-dihydropyridine-3,5-dicarboxylate |
| 12 | 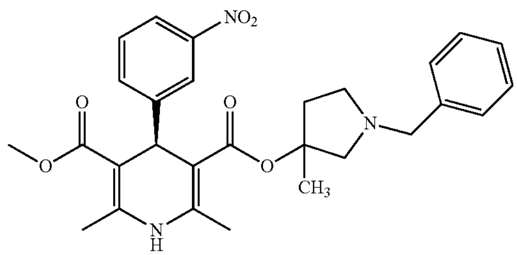 | (4R)-3-(1-benzyl-3-methylpyrrolidin-3-yl) 5-methyl 2,6-dimethyl-4-(3-nitrophenyl)-1,4-dihydropyridine-3,5-dicarboxylate |
| 13 | 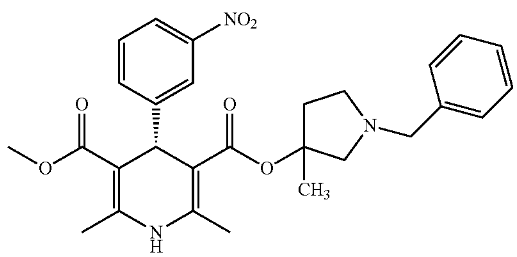 [SMILES: COC(=O)C1=C(C)NC(C)=C(C(=O)OC2(C)CCN(Cc3ccccc3)C2)[C@H]1c1cccc([N+](=O)[O-])c1] | (4S)-3-(1-benzyl-3-methylpyrrolidin-3-yl) 5-methyl 2,6-dimethyl-4-(3-nitrophenyl)-1,4-dihydropyridine-3,5-dicarboxylate |
| 14 | 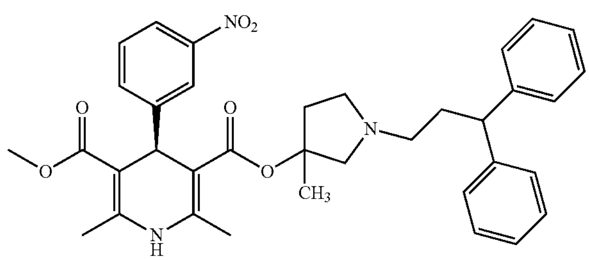 [SMILES: COC(=O)C1=C(C)NC(C)=C(C(=O)OC2(C)CCN(CCC(c3ccccc3)c3ccccc3)C2)[C@@H]1c1cccc([N+](=O)[O-])c1] | (4R)-3-[1-(3,3-diphenylpropyl)-3-methylpyrrolidin-3-yl] 5-methyl 2,6-dimethyl-4-(3-nitrophenyl)-1,4-dihydropyridine-3,5-dicarboxylate |
| 15 | 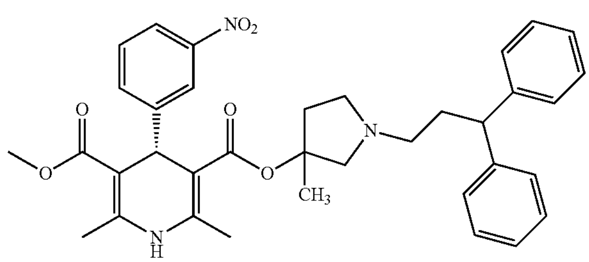 [SMILES: COC(=O)C1=C(C)NC(C)=C(C(=O)OC2(C)CCN(CCC(c3ccccc3)c3ccccc3)C2)[C@H]1c1cccc([N+](=O)[O-])c1] | (4S)-3-[1-(3,3-diphenylpropyl)-3-methylpyrrolidin-3-yl] 5-methyl 2,6-dimethyl-4-(3-nitrophenyl)-1,4-dihydropyridine-3,5-dicarboxylate |

| Compound Structure | | Chemical Name |
|---|---|---|
| 16 | 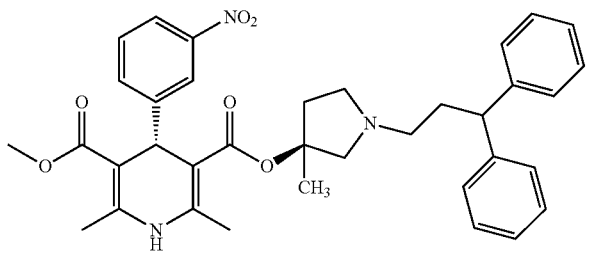 [SMILES: COC(=O)C1=C(C)NC(C)=C(C(=O)O[C@@]2(C)CCN(CCC(c3ccccc3)c3ccccc3)C2)[C@H]1c1cccc([N+](=O)[O-])c1] | (S)-3-[(S)-1-(3,3-diphenylpropyl)-3-methylpyrrolidin-3-yl] 5-methyl 2,6-dimethyl-4-(3-nitrophenyl)-1,4-dihydropyridine-3,5-dicarboxylate |
| 17 | 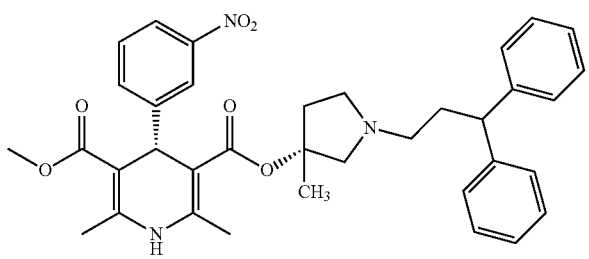 | (S)-3-[(R)-1-(3,3-diphenylpropyl)-3-methylpyrrolidin-3-yl] 5-methyl 2,6-dimethyl-4-(3-nitrophenyl)-1,4-dihydropyridine-3,5-dicarboxylate |
| 18 | 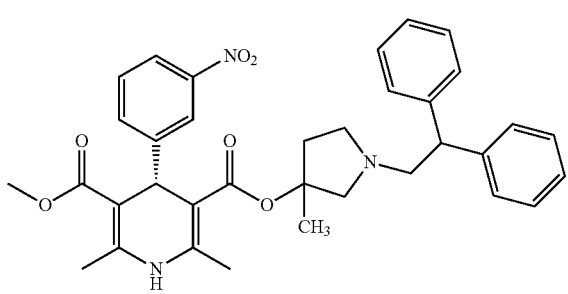 | (4S)-3-[1-(2,2-diphenylethyl)-3-methylpyrrolidin-3-yl] 5-methyl 2,6-dimethyl-4-(3-nitrophenyl)-1,4-dihydropyridine-3,5-dicarboxylate |
| 19 | 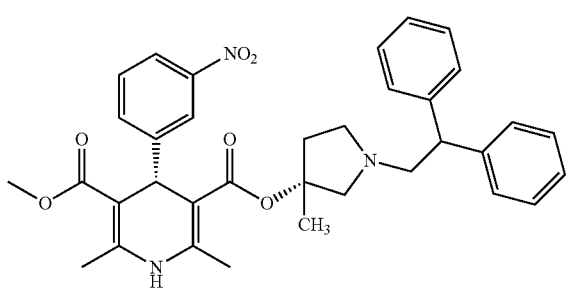 [SMILES: COC(=O)C1=C(C)NC(C)=C(C(=O)O[C@]2(C)CCN(CC(c3ccccc3)c3ccccc3)C2)[C@H]1c1cccc([N+](=O)[O-])c1] | (S)-3-[(R)-1-(2,2-diphenylethyl)-3-methylpyrrolidin-3-yl] 5-methyl 2,6-dimethyl-4-(3-nitrophenyl)-1,4-dihydropyridine-3,5-dicarboxylate |
| 20 | 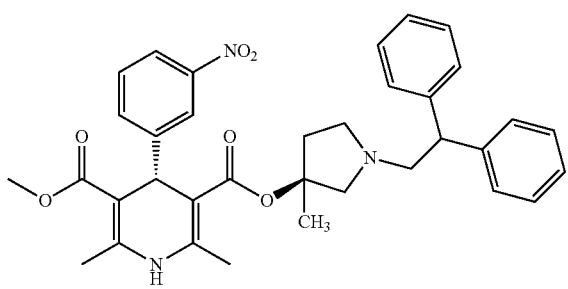 [SMILES: COC(=O)C1=C(C)NC(C)=C(C(=O)O[C@@]2(C)CCN(CC(c3ccccc3)c3ccccc3)C2)[C@H]1c1cccc([N+](=O)[O-])c1] | (S)-3-[(S)-1-(2,2-diphenylethyl)-3-methylpyrrolidin-3-yl] 5-methyl 2,6-dimethyl-4-(3-nitrophenyl)-1,4-dihydropyridine-3,5-dicarboxylate |

-continued

| Compound | Structure | Chemical Name |
|---|---|---|
| 21 | 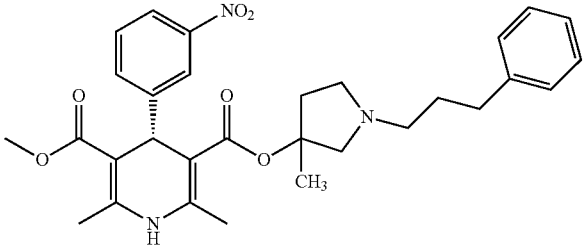 [SMILES: COC(=O)C1=C(C)NC(C)=C(C(=O)OC2(C)CCN(CCCc3ccccc3)C2)[C@H]1c1cccc([N+](=O)[O-])c1] | (4S)-3-[3-methyl-1-(3-phenylpropyl)pyrrolidin-3-yl] 5-methyl 2,6-dimethyl-4-(3-nitrophenyl)-1,4-dihydropyridine-3,5-dicarboxylate |
| 22 | 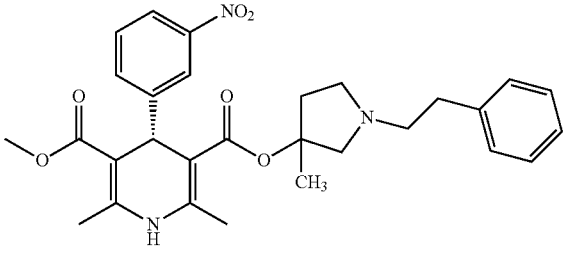 | (4S)-3-(3-methyl-1-phenylethylpyrrolidin-3-yl) 5-methyl 2,6-dimethyl-4-(3-nitrophenyl)-1,4-dihydropyridine-3,5-dicarboxylate |
| 23 | 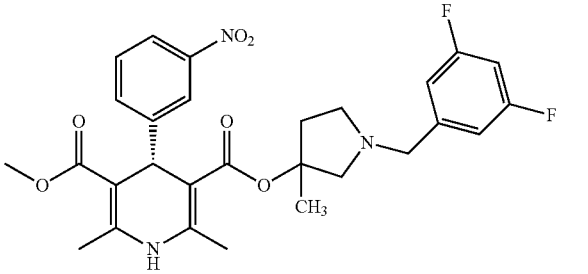 | (4S)-3-[1-(3,5-difluorobenzyl)-3-methylpyrrolidin-3-yl] 5-methyl 2,6-dimethyl-4-(3-nitrophenyl)-1,4-dihydropyridine-3,5-dicarboxylate |
| 24 | 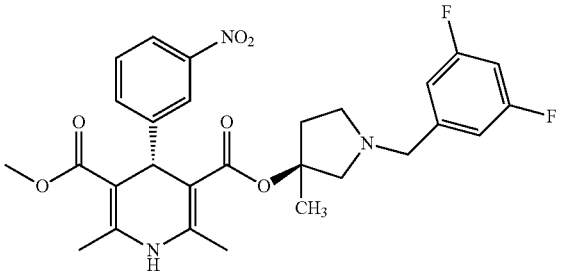 [SMILES: COC(=O)C1=C(C)NC(C)=C(C(=O)O[C@@]2(C)CCN(Cc3cc(F)cc(F)c3)C2)[C@H]1c1cccc([N+](=O)[O-])c1] | (S)-3-[(S)-1-(3,5-difluorobenzyl)-3-methylpyrrolidin-3-yl] 5-methyl 2,6-dimethyl-4-(3-nitrophenyl)-1,4-dihydropyridine-3,5-dicarboxylate |
| 25 | 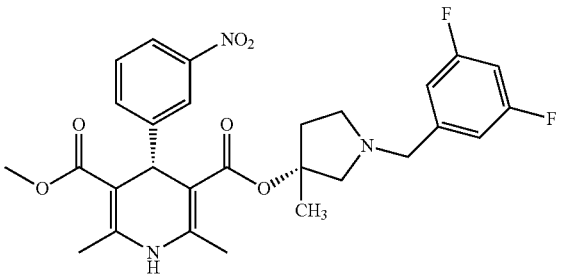 [SMILES: COC(=O)C1=C(C)NC(C)=C(C(=O)O[C@]2(C)CCN(Cc3cc(F)cc(F)c3)C2)[C@H]1c1cccc([N+](=O)[O-])c1] | (S)-3-[(R)1-(3,5-difluorobenzyl)-3-methylpyrrolidin-3-yl] 5-methyl 2,6-dimethyl-4-(3-nitrophenyl)-1,4-dihydropyridine-3,5-dicarboxylate |

-continued

| Compound | Structure | Chemical Name |
|---|---|---|
| 26 | 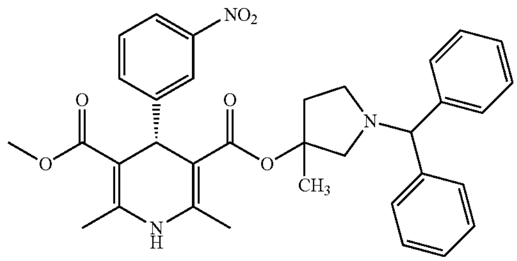 [SMILES: COC(=O)C1=C(C)NC(C)=C(C(=O)OC2(C)CCN(C(c3ccccc3)c3ccccc3)C2)[C@H]1c1cccc([N+](=O)[O-])c1] | (4S)-3-[1-diphenylmethyl-3-methylpyrrolidin-3-yl] 5-methyl 2,6-dimethyl-4-(3-nitrophenyl)-1,4-dihydropyridine-3,5-dicarboxylate |
| 27 | 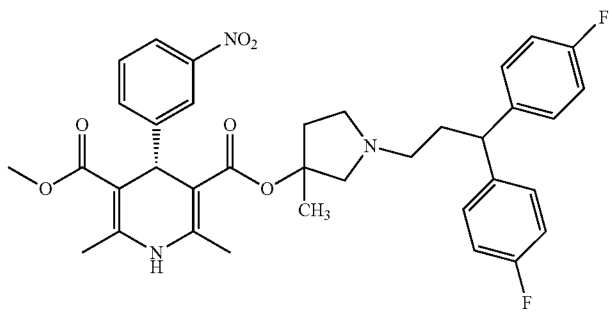 | (4S)-3-[1-(3,3-bis(4-fluorophenyl)propyl)-3-methylpyrrolidin-3-yl] 5-methyl 2,6-dimethyl-4-(3-nitrophenyl)-1,4-dihydropyridine-3,5-dicarboxylate |
| 28 | 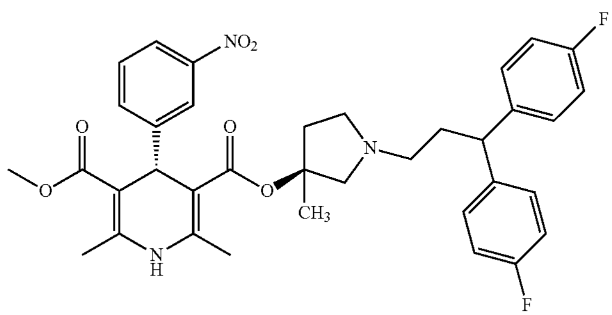 | (S)-3-[(S)-1-(3,3-bis(4-fluorophenyl)propyl)-3-methyl-pyrrolidin-3-yl] 5-methyl 2,6-dimethyl-4-(3-nitrophenyl)-1,4-dihydropyridine-3,5-dicarboxylate |
| 29 | 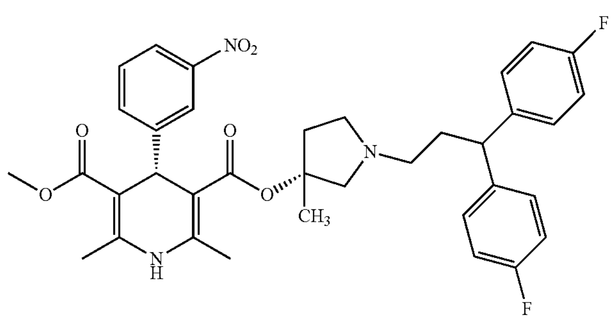 [SMILES: COC(=O)C1=C(C)NC(C)=C(C(=O)O[C@]2(C)CCN(CCC(c3ccc(F)cc3)c3ccc(F)cc3)C2)[C@H]1c1cccc([N+](=O)[O-])c1] | (S)-3-[(R)-1-(3,3-bis(4-fluorophenyl)propyl)-3-methylpyrrolidin-3-yl] 5-methyl 2,6-dimethyl-4-(3-nitrophenyl)-1,4-dihydropyridine-3,5-dicarboxylate |
| 30 | 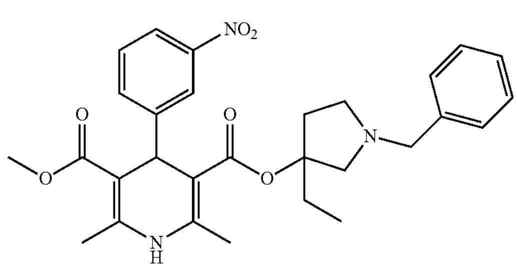 [SMILES: CCC1(OC(=O)C2=C(C)NC(C)=C(C(=O)OC)C2c2cccc([N+](=O)[O-])c2)CCN(Cc2ccccc2)C1] | 3-(1-benzyl-3-ethylpyrrolidin-3-yl) 5-methyl 2,6-dimethyl-4-(3-nitrophenyl)-1,4-dihydropyridine-3,5-dicarboxylate |

| Compound | Structure | Chemical Name |
|---|---|---|
| 31 | 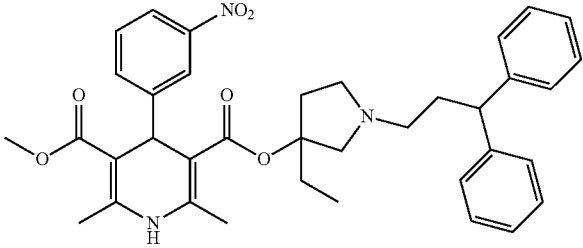 [SMILES: CCC1(OC(=O)C2=C(C)NC(C)=C(C(=O)OC)C2c2cccc([N+](=O)[O-])c2)CCN(CCC(c2ccccc2)c2ccccc2)C1] | 3-[1-(3,3-diphenylpropyl)-3-ethylpyrrolidin-3-yl] 5-methyl 2,6-dimethyl-4-(3-nitrophenyl)-1,4-dihydropyridine-3,5-dicarboxylate |
| 32 | 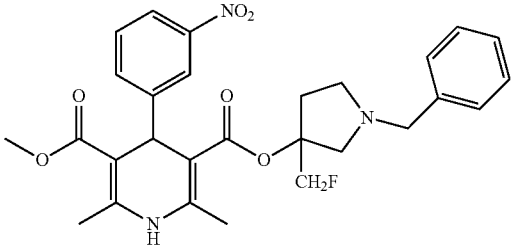 | 3-(1-benzyl-3-fluoromethylpyrrolidin-3-yl) 5-methyl 2,6-dimethyl-4-(3-nitrophenyl)-1,4-dihydropyridine-3,5-dicarboxylate |
| 33 | 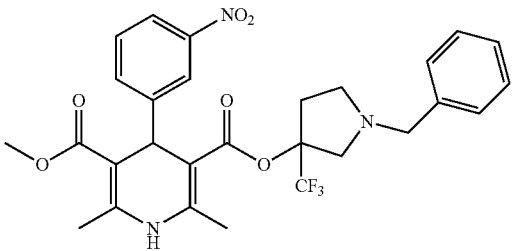 | 3-(1-benzyl-3-trifluoromethylpyrrolidin-3-yl) 5-methyl 2,6-dimethyl-4-(3-nitrophenyl)-1,4-dihydropyridine-3,5-dicarboxylate |
| 34 | 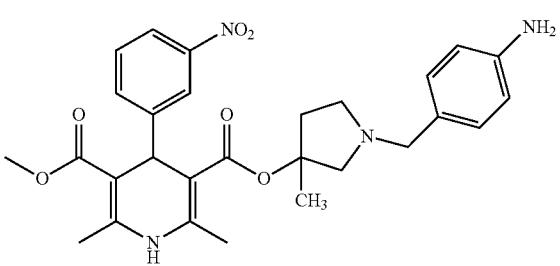 [SMILES: COC(=O)C1=C(C)NC(C)=C(C(=O)OC2(C)CCN(Cc3ccc(N)cc3)C2)C1c1cccc([N+](=O)[O-])c1] | 3-[1-(4-aminobenzyl)-3-methylpyrrolidin-3-yl] 5-methyl 2,6-dimethyl-4-(3-nitrophenyl)-1,4-dihydropyridine-3,5-dicarboxylate |
| 35 | 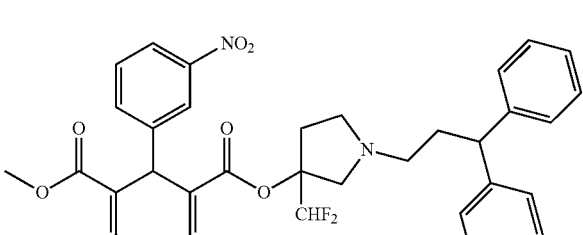 | 3-[3-difluoromethyl-1-(3,3-diphenylpropyl)pyrrolidin-3-yl] 5-methyl 2,6-dimethyl-4-(3-nitrophenyl)-1,4-dihydropyridine-3,5-dicarboxylate |

| Compound | Structure | Chemical Name |
|---|---|---|
| 36 | 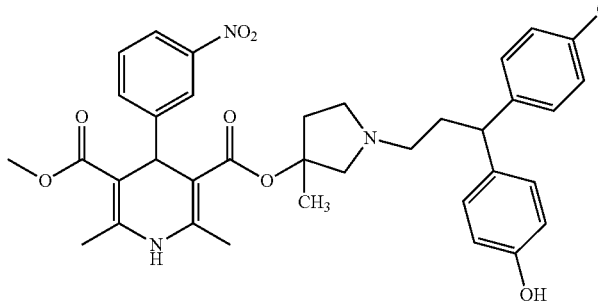 | 3-[1-(3,3-bis(4-hydroxyphenyl)propyl-3-methylpyrrolidin-3-yl] 5-methyl 2,6-dimethyl-4-(3-nitrophenyl)-1,4-dihydropyridine-3,5-dicarboxylate |
| 37 | 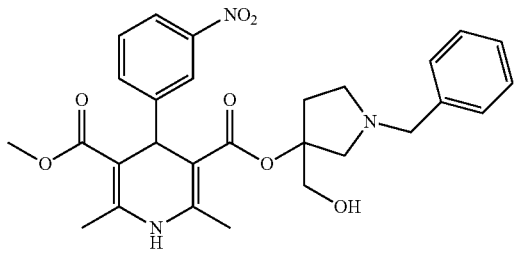 | 3-(1-benzyl-3-hydroxymethylpyrrolidin-3-yl) 5-methyl 2,6-dimethyl-4-(3-nitrophenyl)-1,4-dihydropyridine-3,5-dicarboxylate |
| 38 | 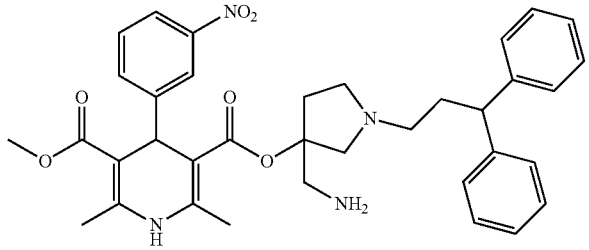 [SMILES: COC(=O)C1=C(C)NC(C)=C(C(=O)OC2(CN)CCN(CCC(c3ccccc3)c3ccccc3)C2)C1c1cccc([N+](=O)[O-])c1] | 3-[3-aminomethyl-1-(3,3-diphenylpropyl)pyrrolidin-3-yl) 5-methyl 2,6-dimethyl-4-(3-nitrophenyl)-1,4-dihydropyridine-3,5-dicarboxylate |
| 39 | 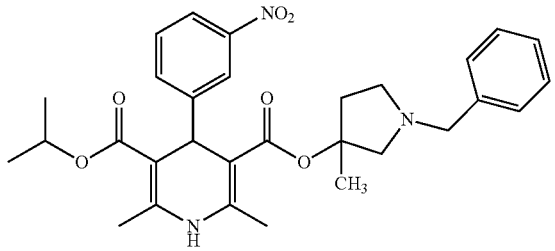 | 3-(1-benzyl-3-methylpyrrolidin-3-yl) 5-isopropyl 2,6-dimethyl-4-(3-nitrophenyl)-1,4-dihydropyridine-3,5-dicarboxylate |
| 40 | 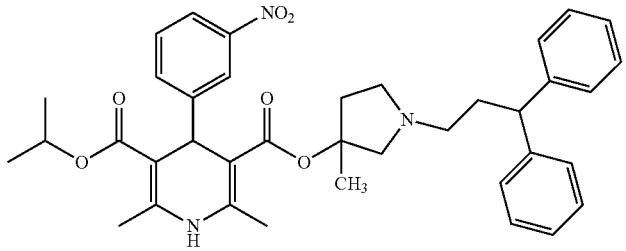 | 3-[1-(3,3-diphenylpropyl)-3-methylpyrrolidin-3-yl] 5-isopropyl 2,6-dimethyl-4-(3-nitrophenyl)-1,4-dihydropyridine-3,5-dicarboxylate |

| Compound Structure | | Chemical Name |
|---|---|---|
| 41 | 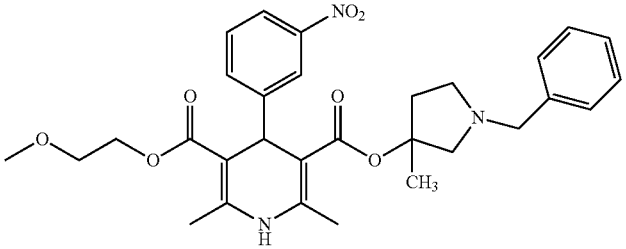 [SMILES: COCCOC(=O)C1=C(C)NC(C)=C(C(=O)OC2(C)CCN(Cc3ccccc3)C2)C1c1cccc([N+](=O)[O-])c1] | 3-(1-benzyl-3-methylpyrrolidin-3-yl) 5-(2-methoxyethyl) 2,6-dimethyl-4-(3-nitrophenyl)-1,4-dihydropyridine-3,5-dicarboxylate |
| 42 | 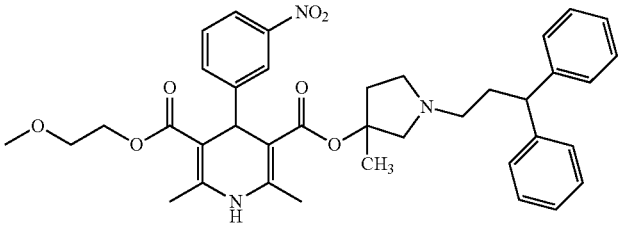 [SMILES: COCCOC(=O)C1=C(C)NC(C)=C(C(=O)OC2(C)CCN(CCC(c3ccccc3)c3ccccc3)C2)C1c1cccc([N+](=O)[O-])c1] | 3-[1-(3,3-diphenylpropyl)-3-methylpyrrolidin-3-yl] 5-(2-methoxyethyl) 2,6-dimethyl-4-(3-nitrophenyl)-1,4-dihydropyridine-3,5-dicarboxylate |
| 43 | 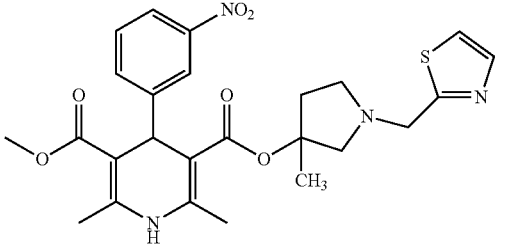 [SMILES: COC(=O)C1=C(C)NC(C)=C(C(=O)OC2(C)CCN(Cc3nccs3)C2)C1c1cccc([N+](=O)[O-])c1] | 3-[3-methyl-1-(thiazol-2-ylmethyl)pyrrolidin-3-yl] 5-methyl 2,6-dimethyl-4-(3-nitrophenyl)-1,4-dihydropyridine-3,5-dicarboxylate |
| 44 | 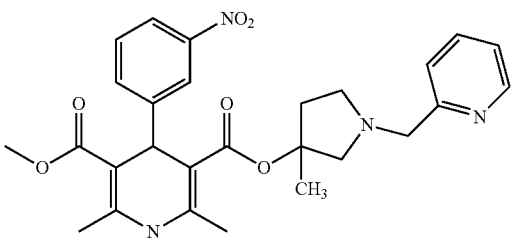 | 3-[3-methyl-1-(pyrid-2-ylmethyl)pyrrolidin-3-yl] 5-methyl 2,6-dimethyl-4-(3-nitrophenyl)-1,4-dihydropyridine-3,5-dicarboxylate |
| 45 | 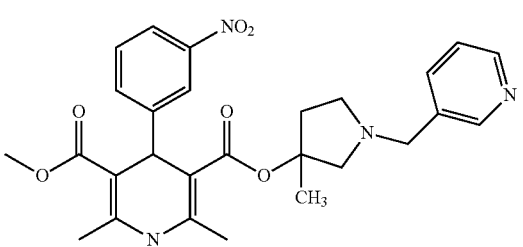 | 3-[3-methyl-1-(pyrid-3-ylmethyl)pyrrolidin-3-yl] 5-methyl 2,6-dimethyl-4-(3-nitrophenyl)-1,4-dihydropyridine-3,5-dicarboxylate |
| 46 | 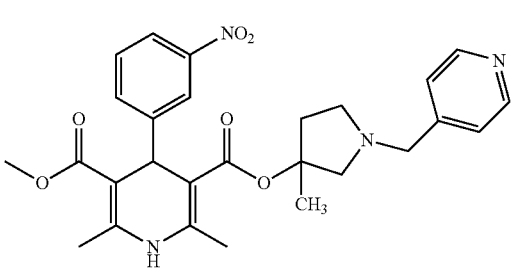 [SMILES: COC(=O)C1=C(C)NC(C)=C(C(=O)OC2(C)CCN(Cc3ccncc3)C2)C1c1cccc([N+](=O)[O-])c1] | 3-[3-methyl-1-(pyrid-4-ylmethyl)pyrrolidin-3-yl]) 5-methyl 2,6-dimethyl-4-(3-nitrophenyl)-1,4-dihydropyridine-3,5-dicarboxylate |

| Compound | Structure | Chemical Name |
|---|---|---|
| 47 | 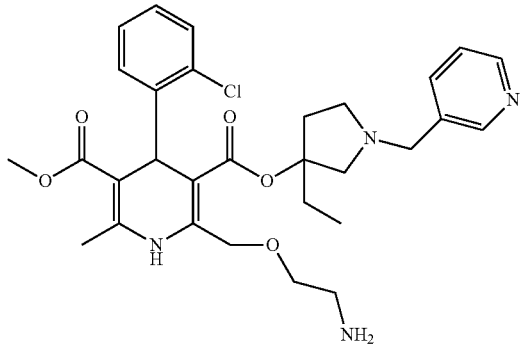 [SMILES: CCC1(OC(=O)C2=C(COCCN)NC(C)=C(C(=O)OC)C2c2ccccc2Cl)CCN(Cc2cccnc2)C1] | 3-[3-ethyl-1-(pyridine-3-ylmethyl)pyrrolidin-3-yl] 5-methyl 2-(2-aminoethoxy)methyl-4-(2-chlorophenyl)-6-methyl-1,4-dihydropyridine-3,5-dicarboxylate |
| 48 | 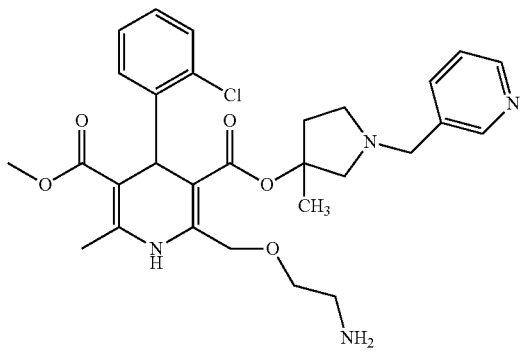 [SMILES: COC(=O)C1=C(C)NC(COCCN)=C(C(=O)OC2(C)CCN(Cc3cccnc3)C2)C1c1ccccc1Cl] | 3-[3-methyl-1-(pyridine-3-ylmethyl)pyrrolidin-3-yl] 5-methyl 2-(2-aminoethoxy)methyl-4-(2-chlorophenyl)-6-methyl-1,4-dihydropyridine-3,5-dicarboxylate |
| 49 | 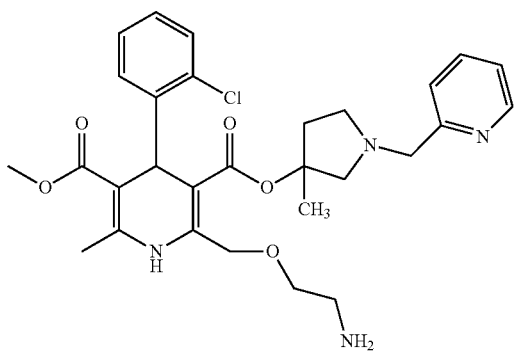 [SMILES: COC(=O)C1=C(C)NC(COCCN)=C(C(=O)OC2(C)CCN(Cc3ccccn3)C2)C1c1ccccc1Cl] | 3-[3-methyl-1-(pyridine-2-ylmethyl)pyrrolidin-3-yl] 5-methyl 2-(2-aminoethoxy)methyl-4-(2-chlorophenyl)-6-methyl-1,4-dihydropyridine-3,5-dicarboxylate |
| 50 | 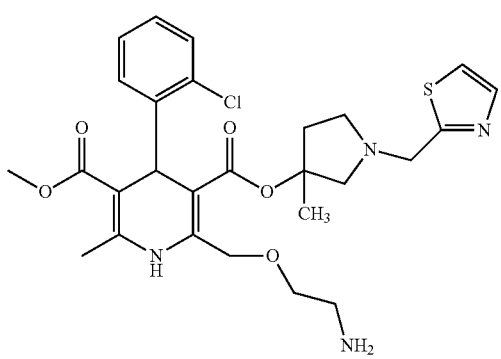 [SMILES: COC(=O)C1=C(C)NC(COCCN)=C(C(=O)OC2(C)CCN(Cc3nccs3)C2)C1c1ccccc1Cl] | 3-[3-methyl-1-(thiazol-2-ylmethyl)pyrrolidin-3-yl] 5-methyl 2-(2-aminoethoxy)methyl-4-(2-chlorophenyl)-6-methyl-1,4-dihydropyridine-3,5-dicarboxylate |

-continued

| Compound | Structure | Chemical Name |
|---|---|---|
| 51 | 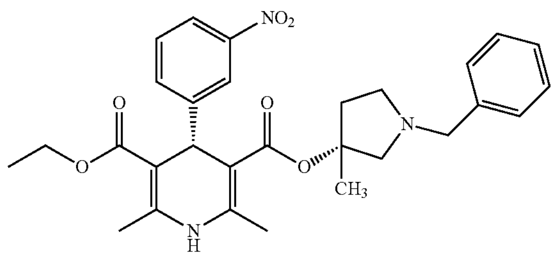 | (S)-3-[(R)-1-benzyl-3-methylpyrrolidin-3-yl] 5-ethyl 2,6-dimethyl-4-(3-nitrophenyl)-1,4-dihydropyridine-3,5-dicarboxylate |
| 52 | 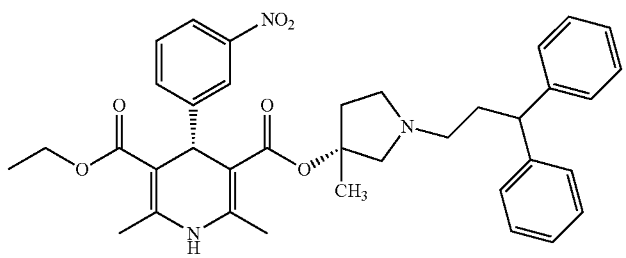 [SMILES: CCOC(=O)C1=C(C)NC(C)=C(C(=O)O[C@]2(C)CCN(CCC(c3ccccc3)c3ccccc3)C2)[C@H]1c1cccc([N+](=O)[O-])c1] | (S)-3-[(R)-1-(3,3-diphenylpropyl)-3-methylpyrrolidin-3-yl] 5-ethyl 2,6-dimethyl-4-(3-nitrophenyl)-1,4-dihydropyridine-3,5-dicarboxylate |
| 53 | 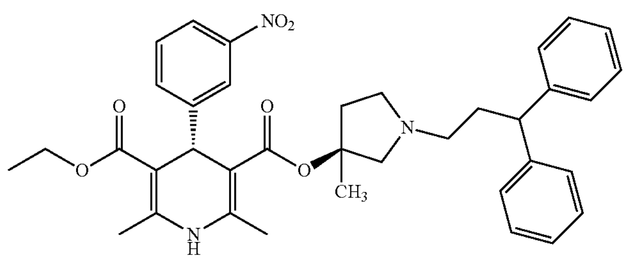 [SMILES: CCOC(=O)C1=C(C)NC(C)=C(C(=O)O[C@@]2(C)CCN(CCC(c3ccccc3)c3ccccc3)C2)[C@H]1c1cccc([N+](=O)[O-])c1] | (S)-3-[(S)-1-(3,3-diphenylpropyl)-3-methylpyrrolidin-3-yl] 5-ethyl 2,6-dimethyl-4-(3-nitrophenyl)-1,4-dihydropyridine-3,5-dicarboxylate |
| 54 | 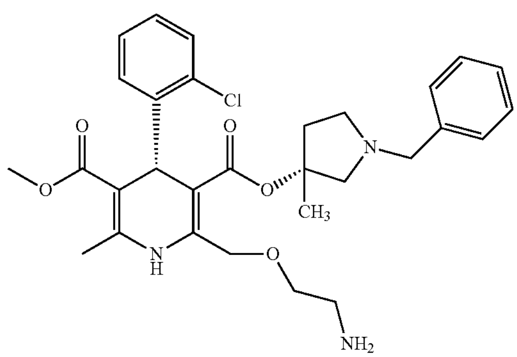 [SMILES: COC(=O)C1=C(C)NC(COCCN)=C(C(=O)O[C@]2(C)CCN(Cc3ccccc3)C2)[C@H]1c1ccccc1Cl] | (S)-3-[(R)-1-benzyl-3-methylpyrrolidin-3-yl] 5-methyl 2-(2-aminoethoxy)methyl-4-(2-chlorophenyl)-6-methyl-1,4-dihydropyridine-3,5-dicarboxylate |
| 55 | 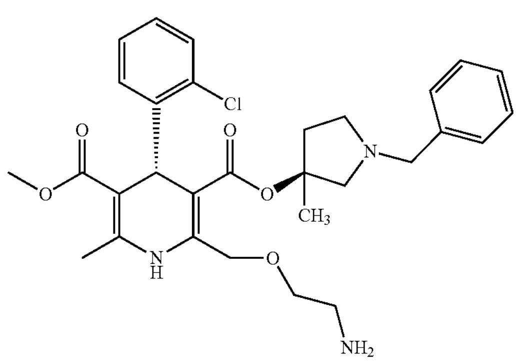 [SMILES: COC(=O)C1=C(C)NC(COCCN)=C(C(=O)O[C@@]2(C)CCN(Cc3ccccc3)C2)[C@H]1c1ccccc1Cl] | (S)-3-[(S)-1-benzyl-3-methylpyrrolidin-3-yl] 5-methyl 2-(2-aminoethoxy)methyl-4-(2-chlorophenyl)-6-methyl-1,4-dihydropyridine-3,5-dicarboxylate |

-continued

| Compound Structure | Chemical Name |
|---|---|
| 56 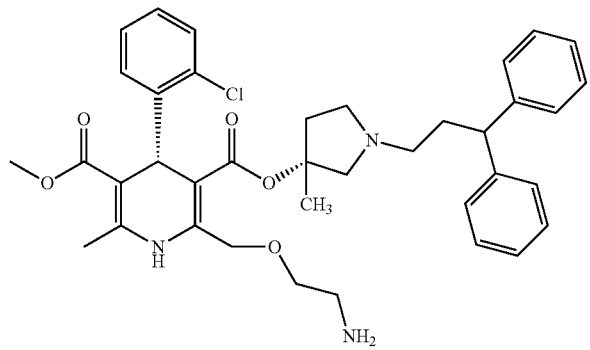 | (S)-3-[(R)-1-(3,3-diphenylpropyl)-3-methylpyrrolidin-3-yl] 5-methyl 2-(2-aminoethoxy)methyl-4-(2-chlorophenyl)-6-methyl-1,4-dihydropyridine-3,5-dicarboxylate |
| 57 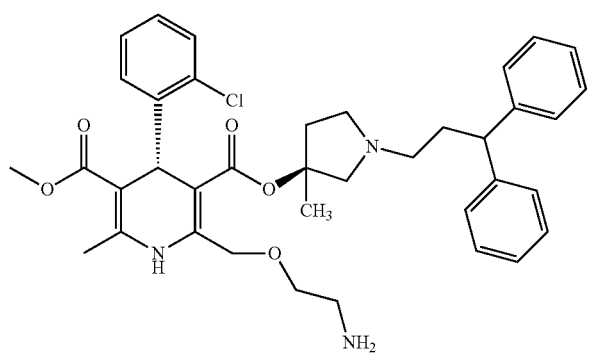 [SMILES: COC(=O)C1=C(C)NC(COCCN)=C(C(=O)O[C@@]2(C)CCN(CCC(c3ccccc3)c3ccccc3)C2)[C@H]1c1ccccc1Cl] | (S)-3-[(S)-1-(3,3-diphenylpropyl)-3-methylpyrrolidin-3-yl] 5-methyl 2-(2-aminoethoxy)methyl-4-(2-chlorophenyl)-6-methyl-1,4-dihydropyridine-3,5-dicarboxylate |
| 58 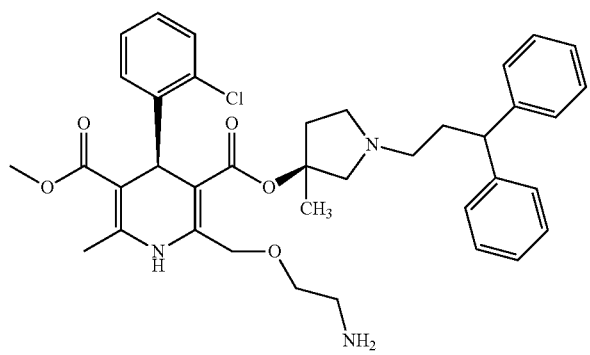 [SMILES: COC(=O)C1=C(C)NC(COCCN)=C(C(=O)O[C@@]2(C)CCN(CCC(c3ccccc3)c3ccccc3)C2)[C@@H]1c1ccccc1Cl] | (R)-3-[(S)-1-(3,3-diphenylpropyl)-3-methylpyrrolidin-3-yl] 5-methyl 2-(2-aminoethoxy)methyl-4-(2-chlorophenyl)-6-methyl-1,4-dihydropyridine-3,5-dicarboxylate |
| 59 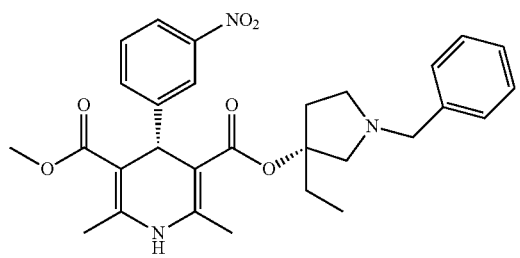 | (S)-3-[(R)-1-benzyl-3-ethylpyrrolidin-3-yl] 5-methyl 2,6-dimethyl-4-(3-nitrophenyl)-1,4-dihydropyridine-3,5-dicarboxylate |
| 60 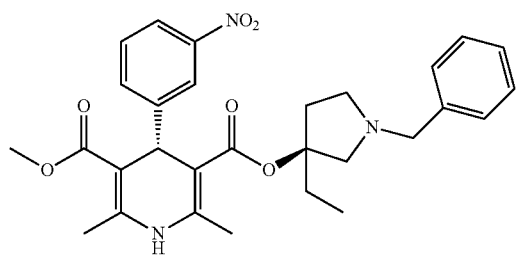 [SMILES: CC[C@]1(OC(=O)C2=C(C)NC(C)=C(C(=O)OC)[C@@H]2c2cccc([N+](=O)[O-])c2)CCN(Cc2ccccc2)C1] | (S)-3-[(S)-1-benzyl-3-ethylpyrrolidin-3-yl] 5-methyl 2,6-dimethyl-4-(3-nitrophenyl)-1,4-dihydropyridine-3,5-dicarboxylate |

| Compound | Structure | Chemical Name |
|---|---|---|
| 61 | 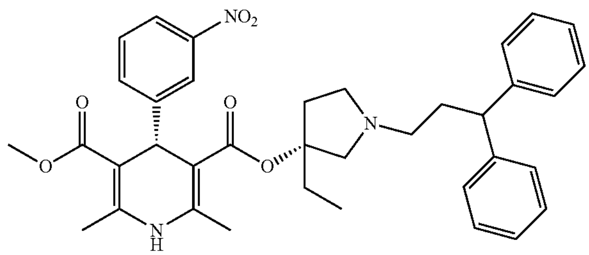 | (S)-3-[(R)-1-(3,3-diphenylpropyl)-3-ethylpyrrolidin-3-yl] 5-methyl 2,6-dimethyl-4-(3-nitrophenyl)-1,4-dihydropyridine-3,5-dicarboxylate |
| 62 | 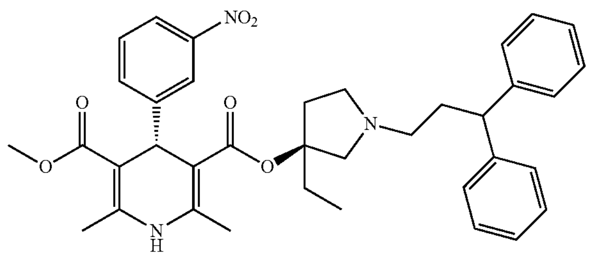 [SMILES: CC[C@]1(OC(=O)C2=C(C)NC(C)=C(C(=O)OC)[C@@H]2c2cccc([N+](=O)[O-])c2)CCN(CCC(c2ccccc2)c2ccccc2)C1] | (S)-3-[(S)-1-(3,3-diphenylpropyl)-3-ethylpyrrolidin-3-yl] 5-methyl 2,6-dimethyl-4-(3-nitrophenyl)-1,4-dihydropyridine-3,5-dicarboxylate |
| 63 | 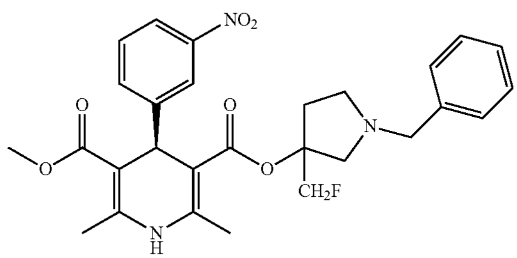 | (4R)-3-(1-benzyl-3-fluoromethylpyrrolidin-3-yl) 5-methyl 2,6-dimethyl-4-(3-nitrophenyl)-1,4-dihydropyridine-3,5-dicarboxylate |
| 64 | 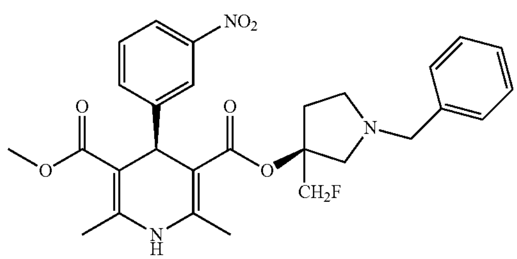 | (R)-3-[(S)-1-benzyl-3-fluoromethylpyrrolidin-3-yl] 5-methyl 2,6-dimethyl-4-(3-nitrophenyl)-1,4-dihydropyridine-3,5-dicarboxylate |
| 65 | 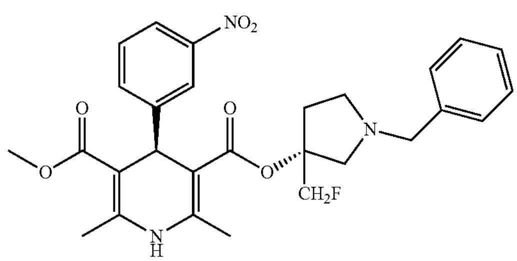 | (R)-3-[(R)-1-benzyl-3-fluoromethylpyrrolidin-3-yl] 5-methyl 2,6-dimethyl-4-(3-nitrophenyl)-1,4-dihydropyridine-3,5-dicarboxylate |
| 66 | 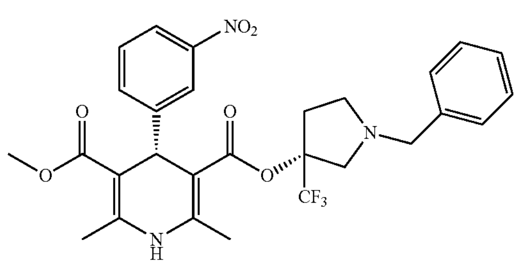 [SMILES: COC(=O)C1=C(C)NC(C)=C(C(=O)O[C@]2(C(F)(F)F)CCN(Cc3ccccc3)C2)[C@H]1c1cccc([N+](=O)[O-])c1] | (S)-3-[(R)-1-benzyl-3-trifluoromethylpyrrolidin-3-yl] 5-methyl 2,6-dimethyl-4-(3-nitrophenyl)-1,4-dihydropyridine-3,5-dicarboxylate |

| Compound | Structure | Chemical Name |
|---|---|---|
| 67 | 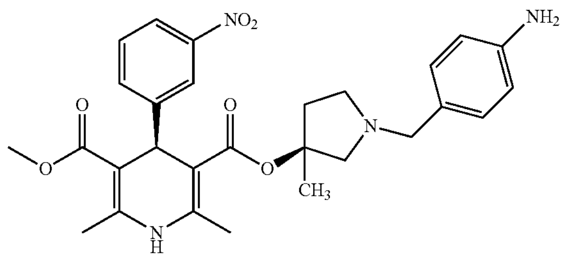 [SMILES: COC(=O)C1=C(C)NC(C)=C(C(=O)O[C@@]2(C)CCN(Cc3ccc(N)cc3)C2)[C@@H]1c1cccc([N+](=O)[O-])c1] | (R)-3-[(S)-1-(4-aminobenzyl)-3-methylpyrrolidin-3-yl] 5-methyl 2,6-dimethyl-4-(3-nitrophenyl)-1,4-dihydropyridine-3,5-dicarboxylate |
| 68 | 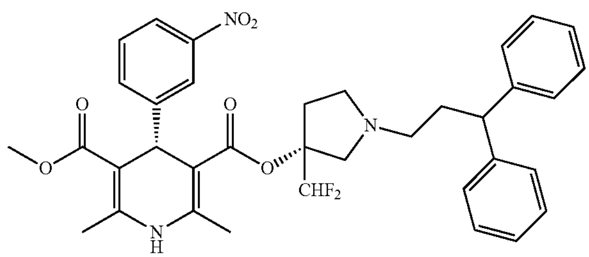 | (S)-3-[(R)-3-difluoromethyl-1-(3,3-diphenylpropyl)pyrrolidin-3-yl] 5-methyl 2,6-dimethyl-4-(3-nitrophenyl)-1,4-dihydropyridine-3,5-dicarboxylate |
| 69 | 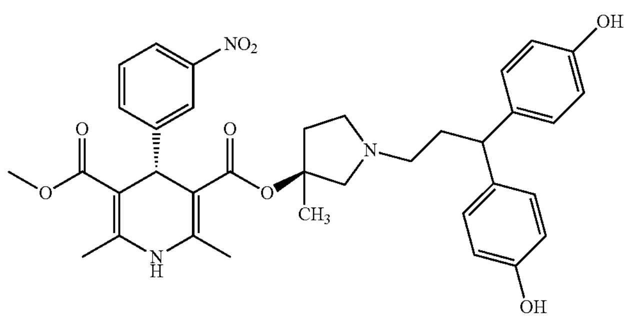 [SMILES: COC(=O)C1=C(C)NC(C)=C(C(=O)O[C@@]2(C)CCN(CCC(c3ccc(O)cc3)c3ccc(O)cc3)C2)[C@H]1c1cccc([N+](=O)[O-])c1] | (S)-3-[(S)-1-(3,3-bis(4-hydroxyphenylpropyl)-3-methyl-pyrrolidin-3-yl] 5-methyl 2,6-dimethyl-4-(3-nitrophenyl)-1,4-dihydropyridine-3,5-dicarboxylate |
| 70 | 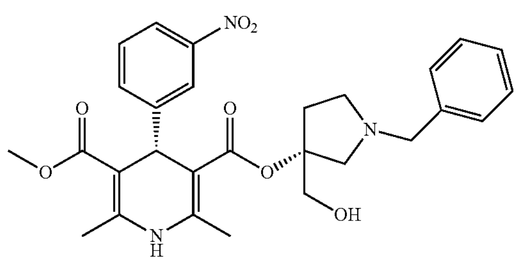 [SMILES: COC(=O)C1=C(C)NC(C)=C(C(=O)O[C@]2(CO)CCN(Cc3ccccc3)C2)[C@H]1c1cccc([N+](=O)[O-])c1] | (S)-3-[(R)-1-benzyl-3-hydroxymethylpyrrolidin-3-yl] 5-methyl 2,6-dimethyl-4-(3-nitrophenyl)-1,4-dihydropyridine-3,5-dicarboxylate |
| 71 | 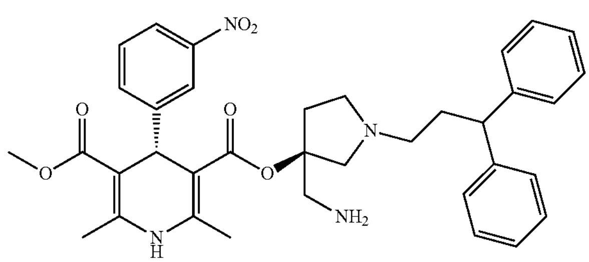 [SMILES: COC(=O)C1=C(C)NC(C)=C(C(=O)O[C@@]2(CN)CCN(CCC(c3ccccc3)c3ccccc3)C2)[C@H]1c1cccc([N+](=O)[O-])c1] | (S)-3-[(R)-3-aminomethyl-1-(3,3-diphenylpropyl)pyrrolidin-3-yl] 5-methyl 2,6-dimethyl-4-(3-nitrophenyl)-1,4-dihydropyridine-3,5-dicarboxylate |

| Compound | Structure | Chemical Name |
|---|---|---|
| 72 | 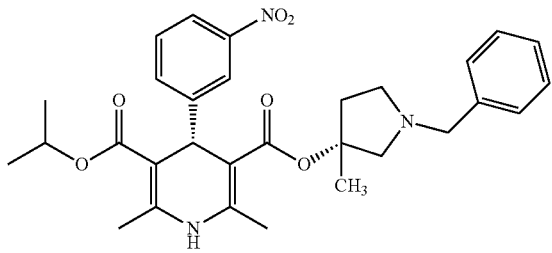 [SMILES: CC1=C(C(=O)OC(C)C)[C@H](c2cccc([N+](=O)[O-])c2)C(C(=O)O[C@]2(C)CCN(Cc3ccccc3)C2)=C(C)N1] | (S)-3-[(R)-1-benzyl-3-methylpyrrolidin-3-yl] 5-isopropyl 2,6-dimethyl-4-(3-nitrophenyl)-1,4-dihydropyridine-3,5-dicarboxylate |
| 73 | 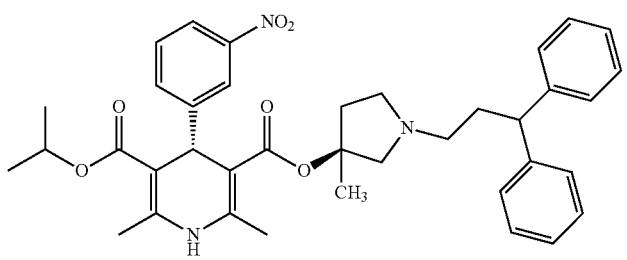 | (S)-3-[(S)-1-(3,3-diphenylpropyl)-3-methylpyrrolidin-3-yl] 5-isopropyl 2,6-dimethyl-4-(3-nitrophenyl)-1,4-dihydropyridine-3,5-dicarboxylate |
| 74 | 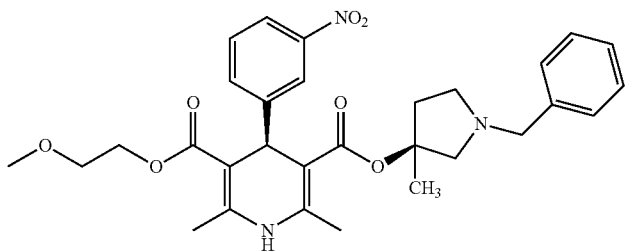 [SMILES: COCCOC(=O)C1=C(C)NC(C)=C(C(=O)O[C@@]2(C)CCN(Cc3ccccc3)C2)[C@@H]1c1cccc([N+](=O)[O-])c1] | (R)-3-[(S)-1-benzyl-3-methylpyrrolidin-3-yl] 5-(2-methoxyethyl) 2,6-dimethyl-4-(3-nitrophenyl)-1,4-dihydropyridine-3,5-dicarboxylate |
| 75 | 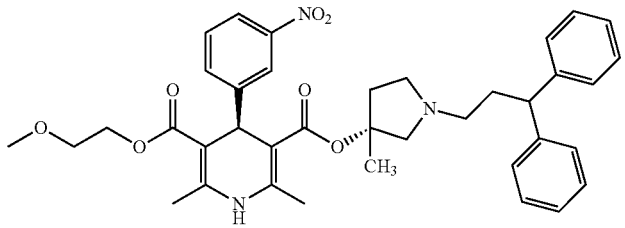 [SMILES: COCCOC(=O)C1=C(C)NC(C)=C(C(=O)O[C@]2(C)CCN(CCC(c3ccccc3)c3ccccc3)C2)[C@@H]1c1cccc([N+](=O)[O-])c1] | (R)-3-[(R)-1-(3,3-diphenylpropyl)-3-methylpyrrolidin-3-yl] 5-(2-methoxyethyl) 2,6-dimethyl-4-(3-nitrophenyl)-1,4-dihydropyridine-3,5-dicarboxylate |
| 76 | 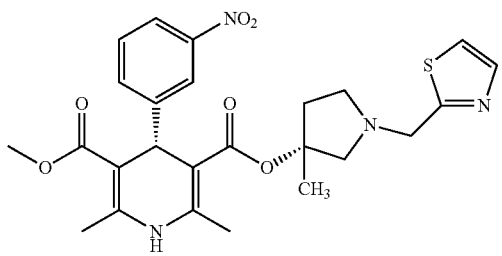 | (S)-3-[(R)-3-methyl-1-(thiazol-2-ylmethyl)pyrrolidin-3-yl] 5-methyl 2,6-dimethyl-4-(3-nitrophenyl)-1,4-dihydropyridine-3,5-dicarboxylate |

| Compound | Structure | Chemical Name |
|---|---|---|
| 77 | 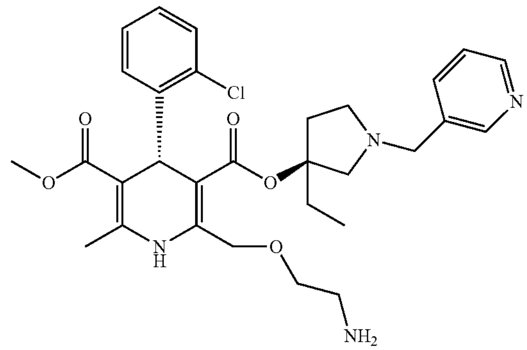 [SMILES: CC[C@]1(OC(=O)C2=C(COCCN)NC(C)=C(C(=O)OC)[C@@H]2c2ccccc2Cl)CCN(Cc2cccnc2)C1] | (S)-3-[(S)-3-ethyl-1-(pyridine-3-ylmethyl)pyrrolidin-3-yl] 5-methyl 2-(2-aminoethoxy)methyl-4-(2-chlorophenyl)-6-methyl-1,4-dihydropyridine-3,5-dicarboxylate |
| 78 | 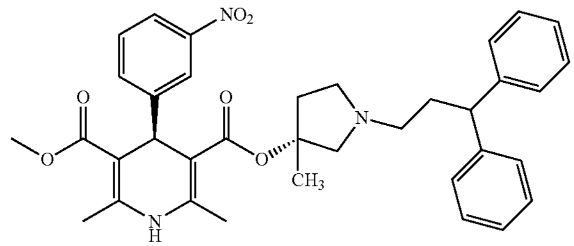 [SMILES: COC(=O)C1=C(C)NC(C)=C(C(=O)O[C@]2(C)CCN(CCC(c3ccccc3)c3ccccc3)C2)[C@@H]1c1cccc([N+](=O)[O-])c1] | (R)-3-[(R)-1-(3,3-diphenylpropyl)-3-methylpyrrolidin-3-yl] 5-methyl 2,6-dimethyl-4-(3-nitrophenyl)-1,4-dihydropyridine-3,5-dicarboxylate |
| 79 | 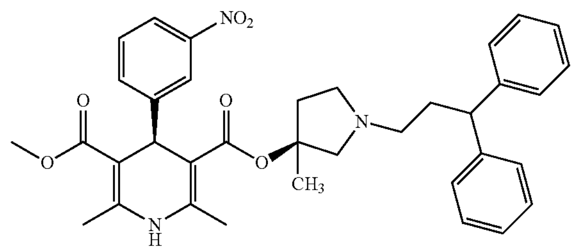 [SMILES: COC(=O)C1=C(C)NC(C)=C(C(=O)O[C@@]2(C)CCN(CCC(c3ccccc3)c3ccccc3)C2)[C@@H]1c1cccc([N+](=O)[O-])c1] | (R)-3-[(S)-1-(3,3-diphenylpropyl)-3-methylpyrrolidin-3-yl] 5-methyl 2,6-dimethyl-4-(3-nitrophenyl)-1,4-dihydropyridine-3,5-dicarboxylate |

In an embodiment of the process for preparing a compound of general formula (I) of the present invention, the compound of general formula (I) of the present invention can be prepared, for example, by the following specific steps:

Reaction schemes:

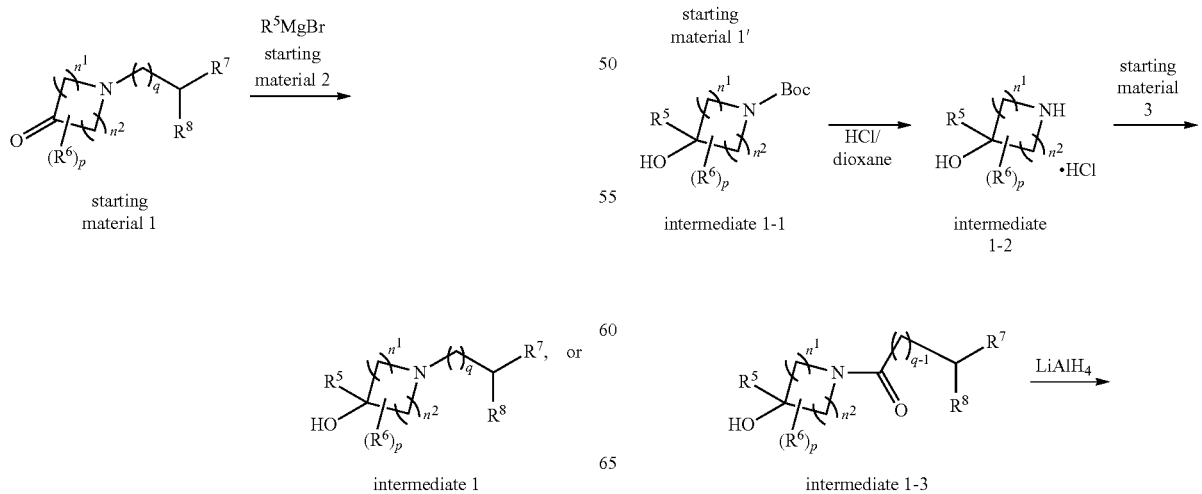

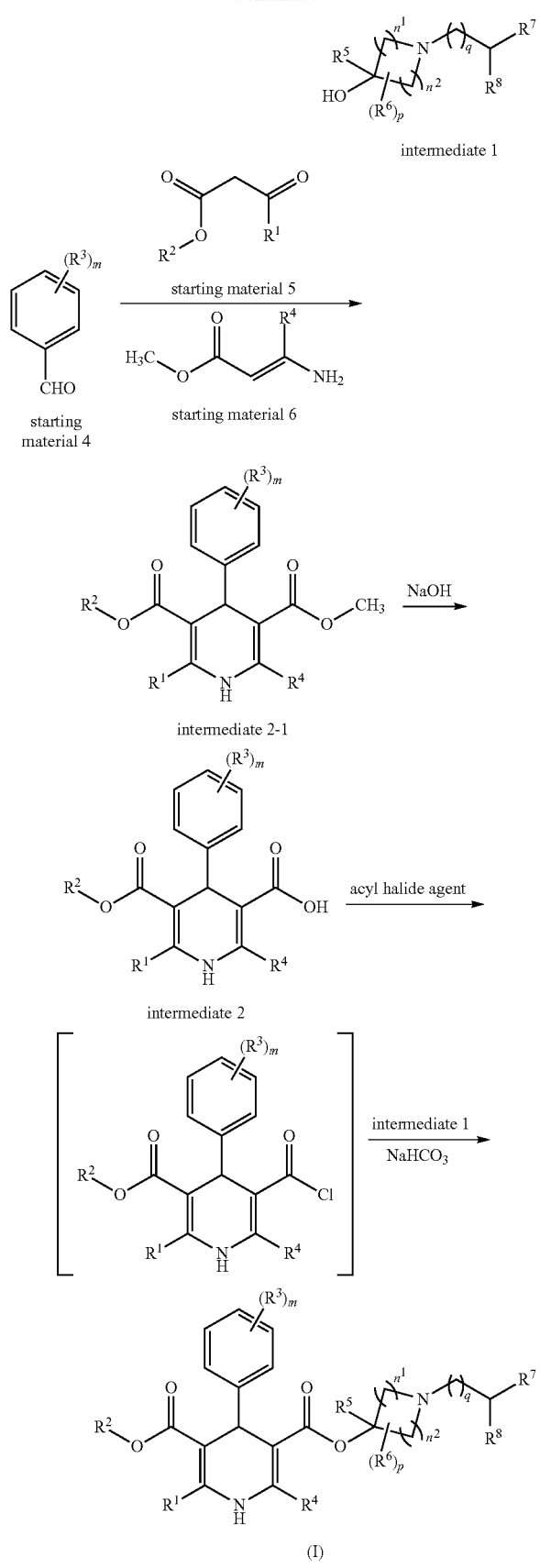

intermediate 1

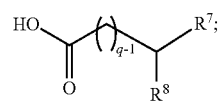

wherein $R^1$, $R^2$, $R^3$, $R^4$, $R^5$, $R^6$, $R^7$, $R^8$, m, $n^1$, $n^2$, p and q are as defined above;
starting material 2=$R^5MgX$, wherein X is Br or I;
starting material 2'=$R^5MgI$,
starting material Reaction Steps Step 1: Preparation of Intermediate 1

Method 1:
Starting material 1 (1 equivalent) is dissolved in an organic solvent (e.g. THF (tetrahydrofuran), diethyl ether, 1,4-dioxane, DMF (dimethylformamide), DMSO (dimethyl sulfoxide) or acetonitrile, and the like) at a low temperature such as from −30 to −10° C., and the resulting solution is dropwisely added to a solution of starting material 2 (2 equivalents) in said organic solvent. The reaction is conducted under stirring to produce intermediate 1.

Method 2:
A solution of starting material 1' (1 equivalent) in an organic solvent (e.g. THF, diethyl ether, 1,4-dioxane, DMF, DMSO or acetonitrile, and the like) is slowly added to a solution of starting material 2' (2 equivalents) in an organic solvent (e.g. diethyl ether, 1,4-dioxane, acetonitrile, and the like). The reaction is conducted under stirring at a low temperature (from −30 to −10° C., e.g. −20° C.) to produce a crude product of intermediate 1-1.

Then the above crude product is dissolved in an organic solvent such as 1,4-dioxane (or diethyl ether, acetonitrile, and the like). Then a gaseous HCl is introduced. The reaction is conducted overnight under stirring to produce intermediate 1-2.

The intermediate 1-2 (1 equivalent), starting material 3 (1.1 equivalents), DIEA (N,N-diisopropylethylamine, 2 equivalents) and an organic solvent such as DMF are stirred at 0° C. HATU (2-(7-azabenzotriazole)-N,N,N',N'-tetramethyluronium hexafluorophosphate, 1.1 equivalents) is further added. The reaction is conducted overnight under stirring to produce intermediate 1-3.

A reductant such as $LiAlH_4$ (3 equivalents) and a solvent such as THF are stirred at a low temperature such as from −30 to −10° C. A solution of intermediate 1-3 (1 equivalent) in said organic solvent is further added dropwisely. The reaction is conducted under stirring to produce intermediate 1.

Step 2: Preparation of Intermediate 2

Starting material 4, starting material 5 and starting material 6 are dissolved in an organic solvent (e.g. an alcohol solvent such as ethanol, methanol, isopropanol, butanol, ethylene glycol, and the like). An inorganic base, such as ammonium bicarbonate, sodium bicarbonate, sodium hydroxide, and the like, is optionally added. The reaction is conducted under stirring and under reflux to produce intermediate 2-1. The intermediate 2-1 is dissolved in an organic solvent (e.g. an alcohol solvent such as methanol, ethanol, isopropanol, butanol or ethylene glycol, and the like). A base such as an aqueous NaOH solution is added under stirring. The reaction is conducted under stirring to produce intermediate 2.

Step 3: Preparation of a Compound of Forumla (I)

Thionyl chloride is slowly added to a solution of the intermediate 2 in an organic solvent (e.g. a low polar organic solvent such as dichloromethane, ethyl acetate, methyl tert-butyl ether or toluene, and the like) at a low temperature such as from −40 to −10° C. The reaction is conducted until the solution becomes clear. The reaction solution is rotary evaporated to dryness to produce a crude product. The resulting crude product and intermediate 1 are reacted under stirring under a basic condition (e.g. in the presence of sodium bicarbonate, sodium hydroxide) at a low temperature such as from −40 to −10° C. to produce a compound of formula (I).

The compound of formula (I) or a stereoisomer thereof of the present invention can be used in a free form or in a form of its pharmaceutically acceptable salt. The compound of formula (I) of the present invention is alkaline and can form an acid addition salt with an inorganic acid or an organic acid, said acid addition salt including but not limited to, e.g., hydrochloride, hydrofluoride, hydrobromide, hydroiodide, sulfate, trifluoroacetate, benzenesulphonate, mesylate, trifluoromesylate, esylate, carbonate, nitrate, phosphate, phosphite, maleate, tartrate, citrate, acetate, benzoate, esylate, fumarate, oxalate, glyconate, glycolate, isethionate, lactate, lactobionate, lactobionate, malate, mesylate, succinate, p-tosylate, glycinate, trimethylglycinate, argininate, ornithinate, glutamate, asprtate, and the like.

The compound of formula (I) or a pharmaceutically acceptable salt thereof of the present invention has an asymmetric carbon atom in its structure, and therefore can be present in optically active isomers. Therefore, the present invention further comprises these optically active isomers and a mixture thereof.

The compound of general formula (I) and a pharmaceutically acceptable salt thereof and a stereoisomer thereof of the present invention can be administered, for example, orally, parenterally (intravenously, intramuscularly, subcutaneously or rectally, and the like), pulmonarily, topically to a mammal e.g. human being. The daily dosage of the compound of the present invention can be in a range of about 0.05 mg/kg body weight to about 0.5 mg/kg body weight.

The compound of formula (I) or a pharmaceutically acceptable salt thereof or a stereoisomer thereof of the present invention and one or more pharmaceutically acceptable carriers can be combined to form a pharmaceutical composition. Said composition can be prepared by mixing the compound of general formula (I) or a pharmaceutically acceptable salt thereof or a stereoisomer thereof of the present invention and one or more conventional pharmaceutically acceptable carriers and/or diluents. Said pharmaceutical composition can be formulated into conventional formulations that are clinically used or pharmaceutically acceptable, and administered to a patient in need thereof by e.g. oral or parenteral administration; including but not limited to, e.g., tablet, granule, capsule, powder, injection, inhalant, sublingual preparation, syrup, gel, salve, suppository, lotion, nasal drop, spray, transdermal preparation, and the like. These formulations can be prepared according to the conventional methods by the addition of suitable pharmaceutically acceptable carriers such as conventional excipients, binders, moisturizers, disintegrants, thickeners, and the like.

The compound of formula (I) or a pharmaceutically acceptable salt thereof or a stereoisomer thereof of the present invention can be administered in combination with other therapeutical agents. Said therapeutical agents include but is not limited to angiotensin II antagonists or a pharmaceutically acceptable salt thereof, including e.g. losartan, valsartan, irbesartan, olmesartan, candesartan, and the like; HMG-Co-A reductase inhibitors or a pharmaceutically acceptable salt thereof, including e.g. lovastatin, simvastatin, pravastatin, mevastatin, fluvastatin, atorvastatin, cerivastatin, lovastatin, and the like; aldosterone receptor antagonists (MRA) or a pharmaceutically acceptable salt thereof, including e.g. spironolactone, eplerenone, and the like; angiotensin converting enzyme/neutral endopeptidase (ACE/NEP) dual inhibitors or a pharmaceutically acceptable salt thereof, including e.g. captopril, alacepril, enalapril, lisinopril, perindopril, ramipril, quinapril, delapril, cilazapril, benazepril, spirapril, trandolapril, moexipril, imidapril, fosinopril, and the like; antidiabetics, including e.g. metformin, glibenclamide, glipizide, glibornuride, gliclazide, gliquidone, sitagliptin, vildagliptin, saxagliptin, alogliptin benzoate, linagliptin, and the like; antiobesics; endothelin receptor blockers, including e.g. bosentan, and the like; CETP inhibitors; Na-K-ATPase membrane pump inhibitors; β-adrenergic receptor inhibitors, including e.g. metoprolol, carvedilol, and the like; α-adrenergic receptor blockers, including e.g. prazosin, terazosin, doxazosin, and the like; neutral endopeptidase (NEP) inhibitors and inotropic agents, and the like.

It is experimentally demonstrated that the compound of the present invention has a remarkable hypotensive activity and can maintain a long acting hypotensive effect, and therefore is a good hypotensive drug. It also has a dual L-type and T-type calcium ion channel blocking effect. Therefore, the compound has a protective effect on heart and kidney, and has a low side effect of ankle edema. Therefore, the compound of formula (I) and a pharmaceutically acceptable salt, and a stereoisomer thereof of the present invention can be used for treating and/or preventing kidney injury, cardiovascular diseases and/or endocrine diseases, including high blood pressure, heart failure, myocardial infarction, angina pectoris, cardiac hypertrophy, myocarditis, cardiovascular fibrosis, baroreceptor dysfunction, fluid overload and arhythmia, primary/secondary aldosteronism, Addison's disease, Cushing's syndrome, Bartter's syndrome, and the like.

In comparison with the prior art, the compound of the present invention has the following advantages:
(1) the compound of the present invention has a good hypotensive effect and a low side effect;
(2) the compound of the present invention has a good inhibition activity on both L-type and T-type calcium ion channels;
(3) the compound of the present invention shows a good biological stability, more lasting effect and a high biological availability;
(4) the process for preparing the compound of the present invention is easy, can provide high purity product with high yield and stable quality, and is easy to be conducted on a large industrial scale.

BEST MODE FOR CARRYING OUT THE INVENTION

Hereinafter, the present invention will be further illustrated in details by the following specific examples. It should be understood that the scope of the present invention is not limited by the following examples, and any technology that can be achieved based on the above disclosures of the present invention falls within the scope of the present invention.

In the examples, the abbreviations have the following meanings:

THF represents tetrahydrofuran
DMF represents dimethylformamide
DIEA represents N,N-diisopropylethylamine
HATU represents 2-(7-azabenzotriazole)-N,N,N',N'-tetramethyluronium hexafluorophosphate
MsCl represents p-methyl benzene sulfonyl chloride
DCM represents dichloromethane

EXAMPLES

I. Examples for Preparing the Compounds of the Present Invention

Example 1

Preparation of 3-(1-benzyl-3-methylpyrrolidin-3-yl) 5-methyl 2,6-dimethyl-4-(3-nitrophenyl)-1,4-dihydropyridine-3,5-dicarboxylate (Compound 1) and its hydrochloride

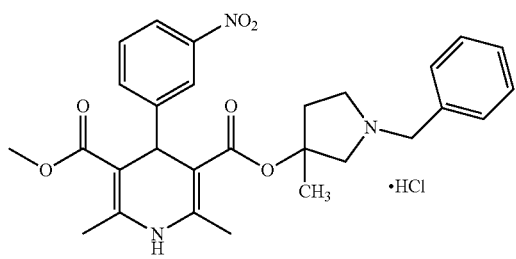 [SMILES: COC(=O)C1=C(C)NC(C)=C(C(=O)OC2(C)CCN(Cc3ccccc3)C2)C1c1cccc([N+](=O)[O-])c1 ; Cl]

(1) Preparation of 1-benzyl-3-methylpyrrolidin-3-ol

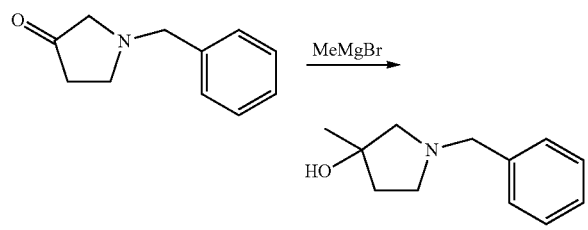

1-benzylpyrrolidone (1.1 g, 6.3 mmol) was dissolved in 4 mL THF under stirring at −20° C. The resulting solution was dropwisely added to a solution of methyl magnesium bromide (13.2 mL, 12.2 mmol) in THF. The stirring was continued for 3 hours. After the completion of reaction, the reaction solution was dropwisely added to an ice water. The resulting mixture was washed with a saturated aqueous NaCl solution, dried over $Na_2SO_4$, and purified by column chromatography (silica gel column, eluted with petroleum ether: ethyl acetate=20:1 (volumetric ratio)) to produce the product of 1-benzyl-3-methylpyrrolidinyl-3-ol (0.7 g) in a yield of 58.1%.

(2) Preparation of dimethyl 2,6-dimethyl-4-(3-nitrophenyl)-1,4-dihydropyridine-3,5-dicarboxylate

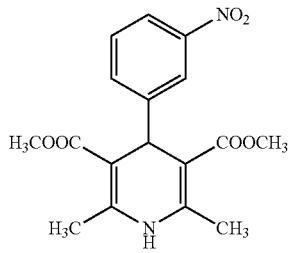

5 g meta-nitrobenzaldehyde (0.033 mol), 8 mL methyl acetoacetate (0.072 mol), 10 mL ethanol, 4 g ammonium bicarbonate (0.05 mol) and 4 mL water were mixed and stirred at 55-60° C. until no bubble formed (about 1 hour). The mixture was continued to react under reflux for 1-2 hours, cooled, and filtered by suction. The filter cake was dried in vacuum to produce the title product as a yellow solid (8.1 g) in a yield of 70.9%.

(3) Preparation of 5-methoxycarbonyl-2,6-dimethyl-4-(3-nitrophenyl)-1,4-dihydropyridine-3-carboxylic acid

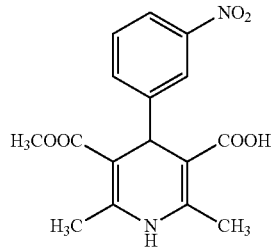

3.5 g dimethyl 2,6-dimethyl-4-(3-nitrophenyl)-1,4-dihydropyridine-3,5-dicarboxylate (0.01 mol) and 150 mL methanol were mixed. To the mixture was added a saturated aqueous NaOH solution (9 g, 0.225 mol) under stirring. The reaction was conducted at 70° C. under violent stirring for 6 hours, and evaporated under reduced pressure to remove 80 mL methanol. To the residue was added 200 mL water. The unreacted starting materials are removed by filtration. The filtrate was adjusted to a pH of about 2.5 with 1 mol/L hydrochloric acid to separate a yellow solid, which was filtered and dried to produce a khaki powder. The resulting powder was treated with methanol to produce the title product as a yellow solid (1.9 g) in a yield of 57.2%.

(4) Preparation of methyl 5-chlorocarbonyl-2,6-dimethyl-4-(3-nitrophenyl)-1,4-dihydropyridine-3-carboxylate

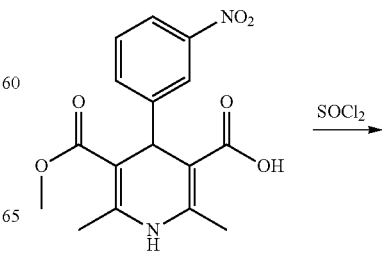

-continued

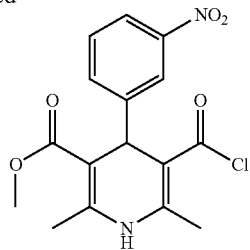

Thionyl chloride (0.4 g, 3.4 mmol) was slowly added to a solution of 5-methoxycarbonyl-2,6-dimethyl-4-(3-nitrophenyl)-1,4-dihydropyridine-3-carboxylic acid (1.0 g, 3 mmol) in dichloromethane dropwisely at −25° C. After the completion of the dropwise addition, the reaction was continued under cooling in an ice bath until the solution became clear. After the completion of reaction, the reaction solution was rotary evaporated to dryness to produce a crude product, which was directly used in the next step.

(5) Preparation of 3-(1-benzyl-3-methylpyrrolidin-3-yl)-5-methyl-2,6-dimethyl-4-(3-nitrophenyl)-1,4-dihydropyridine-3,5-dicarboxylate and its hydrochloride

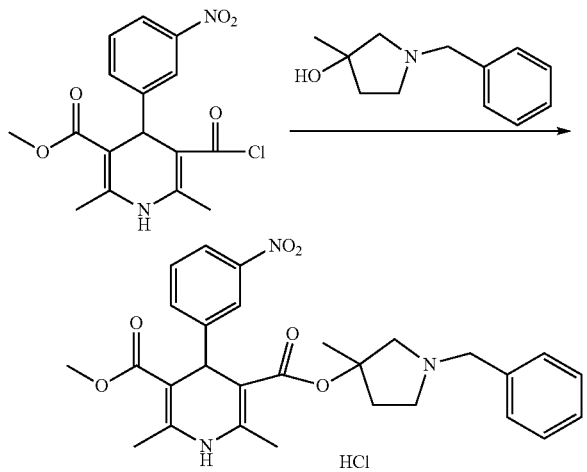

Methyl 5-chlorocarbonyl-2,6-dimethyl-4-(3-nitrophenyl)-1,4-dihydropyridine-3-carboxylate (1.0 g, 2.85 mmol) was added to a solution of 1-benzyl-3-methylpyrrolidinyl-3-ol (0.6 g, 3 mmol) in dichloromethane under stirring at −25° C. After the completion of addition, the solution was moved to room temperature and the stirring was continued for 12 hours. After the completion of reaction, the reaction solution was rotary evaporated to dryness, and purified by column chromatography (silica gel column, eluted with petroleum ether: ethyl acetate=10:1 (volumetric ratio)) to produce Compound 1.

The resulting Compound 1 was dissolved in dichloromethane. To the solution was introduced an HCl gas, and the resulting material was rotary evaporated to dryness to produce the hydrochloride of Compound 1 (0.4 g) in a yield of 25.9%.

MS (M+H): 506.1

1H-NMR (CDCl$_3$, 400 MHz): δ 8.10 (1H, d); 8.02 (1H, d); 7.64 (1H, m); 7.40-7.34 (5H, m); 7.31-7.28 (1H, m); 5.65 (1H, s); 5.07 (1H, s); 3.66 (3H, d); 3.65-3.52 (2H, m); 2.82 (2H, s); 2.76-2.55 (2H, m), 2.38 (3H, s), 2.35 (3H, d), 2.24-2.22 (1H, m), 2.06-1.98 (1H, m), 1.50-1.46 (3H, d).

Example 2

Preparation of 3-[1-(3,3-diphenylpropyl)-3-methylpyrrolidin-3-yl]5-methyl 2,6-dimethyl-4-(3-nitrophenyl)-1,4-dihydropyridine-3,5-dicarboxylate (Compound 2) and its hydrochloride

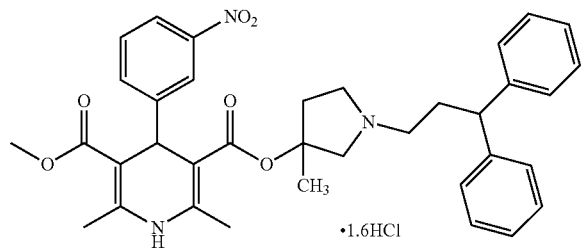 [SMILES: COC(=O)C1=C(C)NC(C)=C(C(=O)OC2(C)CCN(CCC(c3ccccc3)c3ccccc3)C2)C1c1cccc([N+](=O)[O-])c1 ; "·1.6HCl"]

(1) Preparation of 3-methylpyrrolidin-3-ol hydrochloride

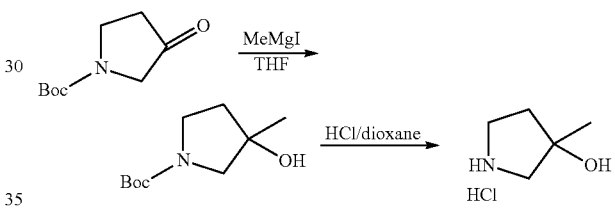

A solution of tert-butyl 3-carbonylpyrrolidine-1-carboxylate (11.17 g, 0.06 mol) in THF (45 mL) was slowly added to a solution of MeMgI (21.41 g, 0.129 mol) in diethyl ether. The reaction was conducted at −20° C. under stirring for 3 hours. A small amount of water was added to the reaction solution. The resulting reaction solution was filtered by suction. The filtrate was extracted with dichloromethane. The organic layer was dried over anhydrous sodium sulfate and filtered. The filtrate was concentrated to produce a crude product of tert-butyl 3-hydroxy-3-methyl-pyrrolidine-1-carboxylate. The above crude product was dissolved in 20 mL 1,4-dioxane. To the resulting solution was introduced an HCl gas. The resulting mixute was stirred overnight and filtered by suction to produce the title product as a red solid (1.67 g) in a yield of 20% (two steps).

(2) Preparation of 1-(3-hydroxy-3-methylpyrrolidin-1-yl)-3,3-diphenylpropyl-1-one

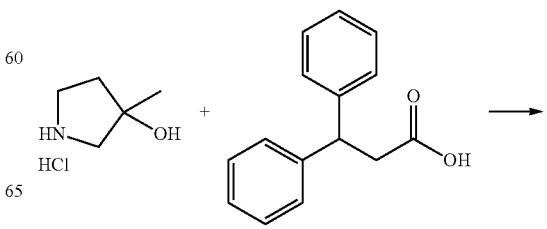

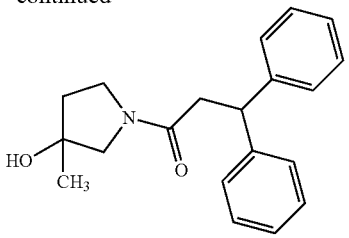

To a 100 mL eggplant-shaped flask were added 3-methylpyrrolidin-3-ol hydrochloride (1.6 g, 11.6 mmol), 3,3-diphenylpropanic acid (2.89 g, 12.9 mmol), DIEA (3.0 g, 23.3 mmol) and DMF (8 mL). The mixture was stirred at 0° C. for 15 minutes, and then HATU (4.86 g, 12.8 mmol) was slowly added thereto. The resulting mixture was stirred for 10 minutes, then moved to room temperature and stirred overnight. The reaction solution was poured into water, adjusted with a diluted hydrochloric acid (10%) to a pH of about 6, and extracted with ethyl acetate. The organic phase was dried over anhydrous sodium sulfate, and filtered. The filtrate was evaporated to dryness, and purified by column chromatography (silica gel column, eluted with petroleum ether: ethyl acetate=15:1 (volumetric ratio)) to produce a light red oily product (1.0 g) in a yield of 28%.

(3) Preparation of 1-(3,3-diphenylpropyl)-3-methylpyrrolidin-3-ol

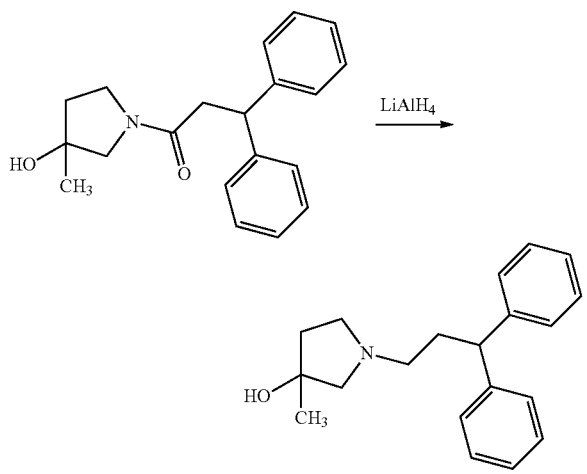

To a 250 mL eggplant-shaped flask were added LiAlH₄ (0.36 g, 9.49 mmol) and THF (10 mL). The mixture was stirred at −20° C. for 15 minutes. Then to the mixture was slowly added a solution of 1-(3-hydroxy-3-methylpyrrolidin-1-yl)-3,3-diphenylpropyl-1-one (1.0 g, 3.24 mmol) in THF (5 mL). After the completion of addition, the temperature was warmed up to 70° C., and the stirring was continued for 4 hours. The mixture was cooled to room temperature. To the mixture were added 0.36 g water, then 0.72 g 10% sodium hydroxide solution, and finally 1.08 g water. After filtering, the filtrate was distilled to remove THF, and extracted with dichloromethane. The organic layer was washed successively with water and a saturated aqueous NaCl solution, dried over anhydrous sodium sulfate, and filtered. The filtrate was evaporated to dryness to give 100 mg product. To the filter cake was added dichloromethane. After stirring, the resulting mixture was filtered by suction. The filtrate was evaporated to dryness to give 550 mg product. The product was 650 mg in total in a yield of 68%.

(4) Preparation of 3-[1-(3,3-diphenylpropyl)-3-methylpyrrolidin-3-yl]5-methyl 2,6-dimethyl-4-(3-nitrophenyl)-1,4-dihydropyridine-3,5-dicarboxylate and its hydrochloride

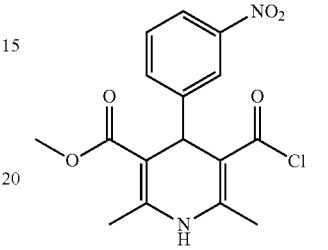

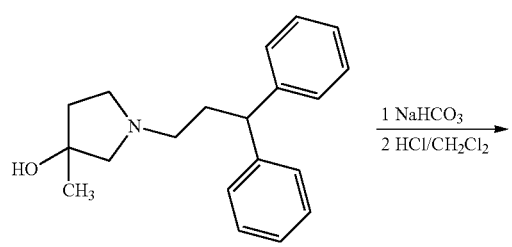

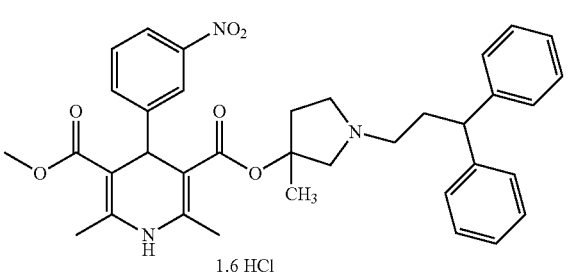

To a 100 mL eggplant-shaped flask were added 1-(3,3-diphenylpropyl)-3-methylpyrrolidin-3-ol (0.65 g, 2.2 mmol), sodium bicarbonate (0.37 g, 4.4 mmol) and dichloromethane (4 mL). The resulting mixture was stirred at −25° C. for 15 minutes. Then to the mixture was slowly added methyl 5-(chlorocarbonyl)-2,6-dimethyl-4-(3-nitrophenyl)-1,4-dihydropyridine-3-carboxylate (0.93 g, 2.64 mmol). The resulting mixture was stirred for 10 minutes, then warmed up to 0° C., and stirred overnight. After filtering, the filtrate was evaporated to dryness, and purified by column chromatography to produce Compound 2.

The resulting Compound 2 was dissolved in dichloromethane. To the resulting solution was introduced an HCl gas. After 10 minutes, the mixture was filtered. The filter cake was dried to produce 168 mg of the hydrochloride of Compound 2 in a yield of 11.4%.

MS (M+H): 610.2.

Example 3

Preparation of 3-(1-benzyl-3-methylpyrrolidin-3-yl) 5-ethyl 2,6-dimethyl-4-(3-nitrophenyl)-1,4-dihydropyridine-3,5-dicarboxylate (Compound 3)

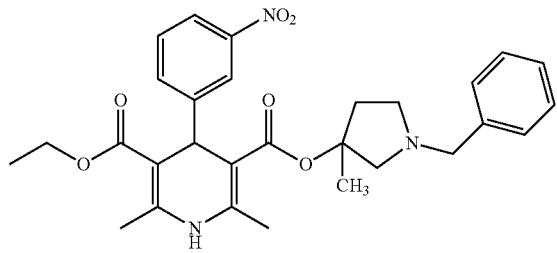 [SMILES: CCOC(=O)C1=C(C)NC(C)=C(C(=O)OC2(C)CCN(Cc3ccccc3)C2)C1c1cccc([N+](=O)[O-])c1]

The steps in Example 1 were repeated, except that the reactant in step (2) methyl acetoacetate was replaced with ethyl acetoacetate to obtain Compound 3.
MS (M+H): 520.3.

Example 4

Preparation of 3-(1-(3,3-diphenylpropyl)-3-methylpyrrolidin-3-yl) 5-ethyl 2,6-dimethyl-4-(3-nitrophenyl)-1,4-dihydropyridine-3,5-dicarboxylate (Compound 4)

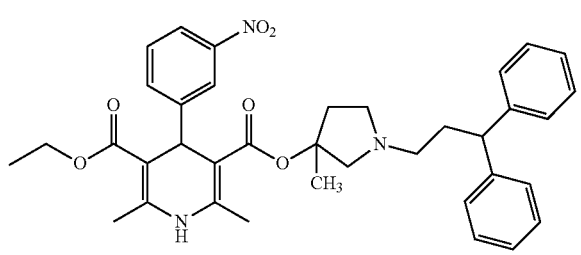 [SMILES: CCOC(=O)C1=C(C)NC(C)=C(C(=O)OC2(C)CCN(CCC(c3ccccc3)c3ccccc3)C2)C1c1cccc([N+](=O)[O-])c1]

The steps in Example 2 were repeated, except that the reactant in step (4) methyl 5-(chlorocarbonyl)-2,6-dimethyl-4-(3-nitrophenyl)-1,4-dihydropyridine-3-carboxylate was replaced with ethyl 5-(chlorocarbonyl)-2,6-dimethyl-4-(3-nitrophenyl)-1,4-dihydropyridine-3-carboxylate to obtain Compound 4.
MS (M+H): 624.2.

Example 5

Preparation of 3-(1-phenylpropyl-3-methylpyrrolidin-3-yl) 5-methyl 2,6-dimethyl-4-(3-nitrophenyl)-1,4-dihydropyridine-3,5-dicarboxylate (Compound 5)

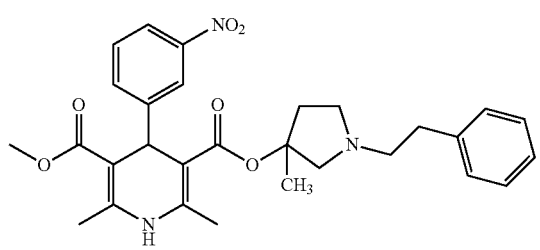 [SMILES: COC(=O)C1=C(C)NC(C)=C(C(=O)OC2(C)CCN(CCc3ccccc3)C2)C1c1cccc([N+](=O)[O-])c1]

The steps in Example 1 were repeated, except that the reactant in step (1) 1-benzylpyrrolidin-3-one was replaced with 1-phenylethylpyrrolidin-3-one to obtain Compound 5.
MS (M+H): 520.3.

Example 6

Preparation of 3-[1-(2,2-diphenylethyl)-3-methylpyrrolidin-3-yl]5-methyl 2,6-dimethyl-4-(3-nitrophenyl)-1,4-dihydropyridine-3,5-dicarboxylate (Compound 6)

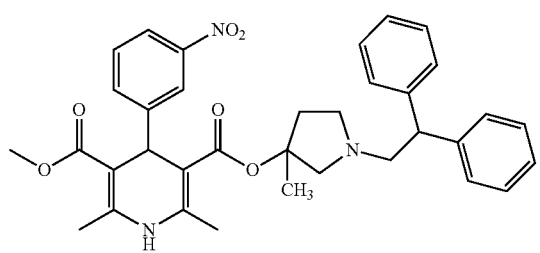 [SMILES: COC(=O)C1=C(C)NC(C)=C(C(=O)OC2(C)CCN(CC(c3ccccc3)c3ccccc3)C2)C1c1cccc([N+](=O)[O-])c1]

The steps in Example 2 were repeated, except that the reactant in step (2) 3,3-diphenylpropanic acid was replaced with 2,2-diphenylacetic acid to obtain Compound 6.
MS (M+H): 596.2.

Example 7

Preparation of 3-(1-benzyl-3-methylpyrrolidin-3-yl) 5-methyl 2-[(2-aminoethoxy)methyl]-4-(2-chlorophenyl)-6-methyl-1,4-dihydropyridine-3,5-dicarboxylate (Compound 7)

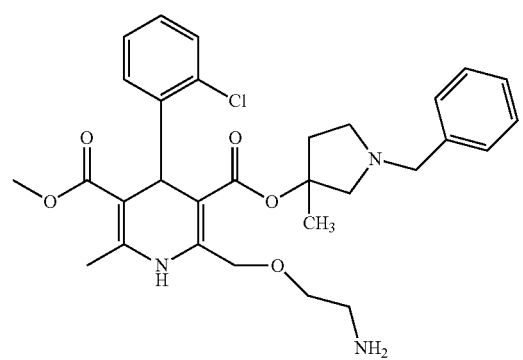 [SMILES: COC(=O)C1=C(C)NC(COCCN)=C(C(=O)OC2(C)CCN(Cc3ccccc3)C2)C1c1ccccc1Cl]

The steps in Example 1 were repeated, except that the reactant in step (2) meta-nitrobenzaldehyde was replaced with 2-chlorobenzaldehyde to obtain Compound 7.
MS (M+H): 554.3.

Example 8

Preparation of 3-[1-(3,3-diphenylpropyl)-3-methylpyrrolidin-3-yl]5-methyl 2-[(2-aminoethoxy)methyl]-4-(2-chlorophenyl)-6-methyl-1,4-dihydropyridine-3,5-dicarboxylate (Compound 8)

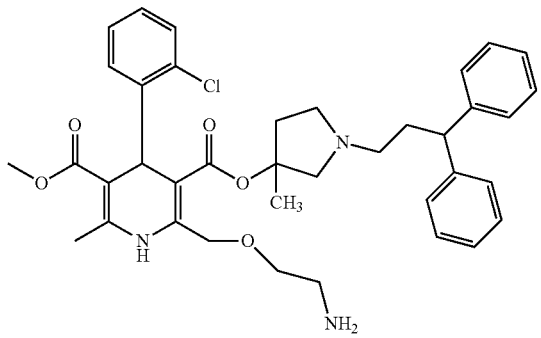 [SMILES: COC(=O)C1=C(C)NC(COCCN)=C(C(=O)OC2(C)CCN(CCC(c3ccccc3)c3ccccc3)C2)C1c1ccccc1Cl]

The steps in Example 2 were repeated, except that methyl 5-(chlorocarbonyl)-2,6-dimethyl-4-(3-nitrophenyl)-1,4-dihydropyridine-3-carboxylate in step (4) was replaced with methyl 5-(chlorocarbonyl)-2,6-dimethyl-4-(2-chlorophenyl)-1,4-dihydropyridine-3-carboxylate to obtain Compound 8.

MS (M+H): 658.2.

Example 9

Preparation of 3-[1-(4-fluorobenzyl)-3-methylpyrrolidin-3-yl]5-methyl 2,6-dimethyl-4-(3-nitrophenyl)-1,4-dihydropyridine-3,5-dicarboxylate (Compound 9)

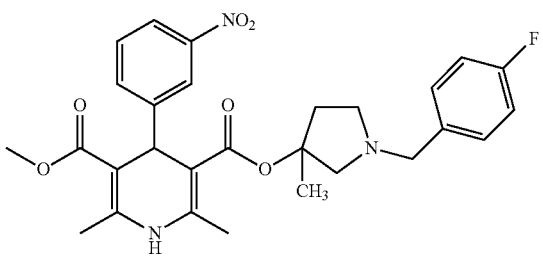 [SMILES: COC(=O)C1=C(C)NC(C)=C(C(=O)OC2(C)CCN(Cc3ccc(F)cc3)C2)C1c1cccc([N+](=O)[O-])c1]

The steps in Example 1 were repeated, except that the reactant in step (1) 1-benzylpyrrolidin-3-one was replaced with 1-(4-fluorobenzyl)pyrrolidin-3-one to obtain Compound 9.

MS (M+H): 524.2.

Example 10

Preparation of 3-[1-(4-methoxybenzyl)-3-methylpyrrolidin-3-yl]5-methyl 2,6-dimethyl-4-(3-nitrophenyl)-1,4-dihydropyridine-3,5-dicarboxylate (Compound 10)

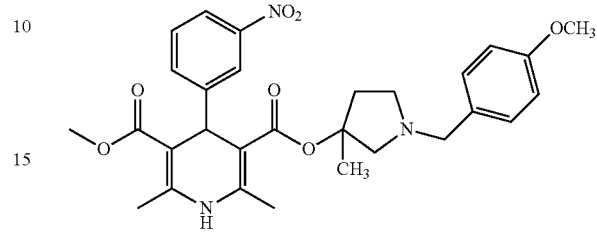

The steps in Example 1 were repeated, except that the reactant in step (1) 1-benzylpyrrolidin-3-one was replaced with 1-(4-methoxybenzyl)pyrrolidin-3-one to obtain Compound 10.

MS (M+H): 536.3.

Example 11

Preparation of 3-[1-(3,3-bis(4-fluorophenyl)propyl)-3-methylpyrrolidin-3-yl]5-methyl 2,6-dimethyl-4-(3-nitrophenyl)-1,4-dihydropyridine-3,5-dicarboxylate (Compound 11)

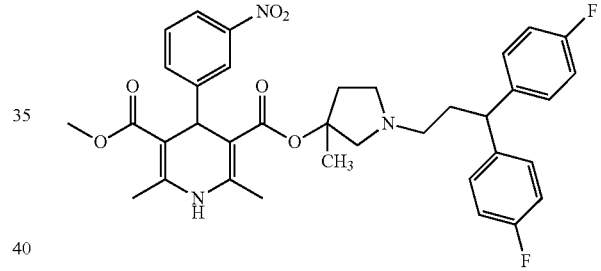

The steps in Example 2 were repeated, except that the reactant in step (2) 1-(3-hydroxy-3-methylpyrrolidin-1-yl)-3,3-diphenylpropyl-1-one was replaced with 1-(3,3-bis(4-fluorophenyl)propyl)-3-methylpyrrolidin-3-one to obtain Compound 11.

MS (M+H): 646.2.

Example 12

Preparation of (4R)-3-(1-benzyl-3-methylpyrrolidin-3-yl) 5-methyl 2,6-dimethyl-4-(3-nitrophenyl)-1,4-dihydropyridine-3,5-dicarboxylate hydrochloride (Compound 12)

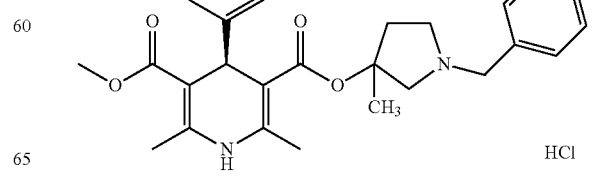

(1) Preparation of (S)-5-methoxycarbonyl-2,6-dimethyl-4-(3-nitrophenyl)-1,4-dihydropyridine-3-carboxylic acid

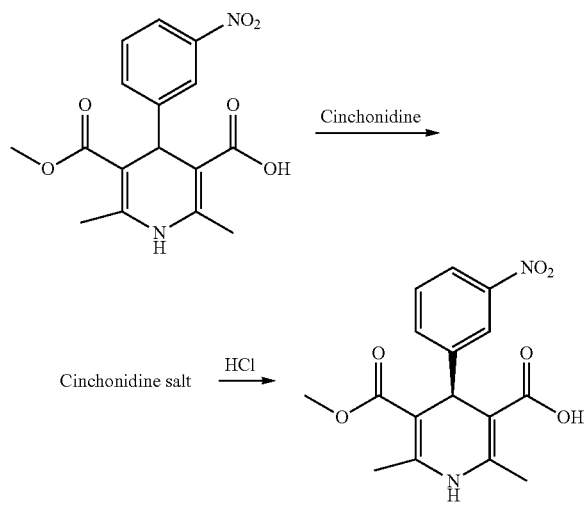

To a solution of 5-methoxycarbonyl-2,6-dimethyl-4-(3-nitrophenyl)-1,4-dihydropyridine-3-carboxylic acid (700 g, 2.1 mol) in methanol (14 L) was added cinchonidine (617 g, 2.1 mol). The mixture was stirred at 90° C. under reflux until cinchonidine was completely dissolved. The stirring was continued for 3 hours. 4.5 L water was added. The stirring was continued for 0.5 hour. The mixture was cooled down slowly. A solid was precipitated out and was filtered. The filter cake was treated with hydrochloric acid to produce (S)-5-(methoxycarbonyl)-2,6-dimethyl-4-(3-nitrophenyl)-1,4-dihydropyridine-3-carboxyl is acid (130 g) in a yield of 18.6%.

(2) Preparation of methyl (R)-5-chlorocarbonyl-2,6-dimethyl-4-(3-nitrophenyl)-1,4-dihydropyridine-3-carboxylate

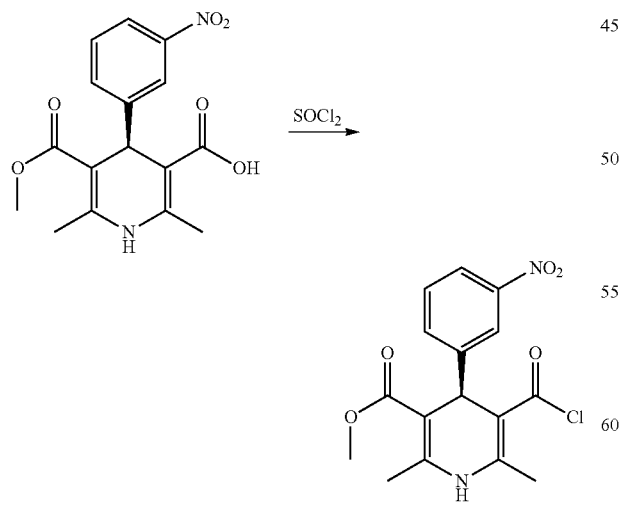

Thionyl chloride (0.4 g, 3.4 mmol) was slowly added to a solution of 5-methoxycarbonyl-2,6-dimethyl-4-(3-nitrophenyl)-1,4-dihydropyridine-3-carboxylic acid (1.0 g, 3 mmol) in dichloromethane dropwisely at −25° C. After the completion of the dropwise addition, the reaction was continued under cooling in an ice bath until the solution became clear. After the completion of reaction, the reaction solution was rotary evaporated to dryness. The product was directly used in the next step.

(3) Preparation of (4R)-3-(1-benzyl-3-methylpyrrolidin-3-yl) 5-methyl 2,6-dimethyl-4-(3-nitrophenyl)-1,4-dihydropyridine-3,5-dicarboxylate hydrochloride

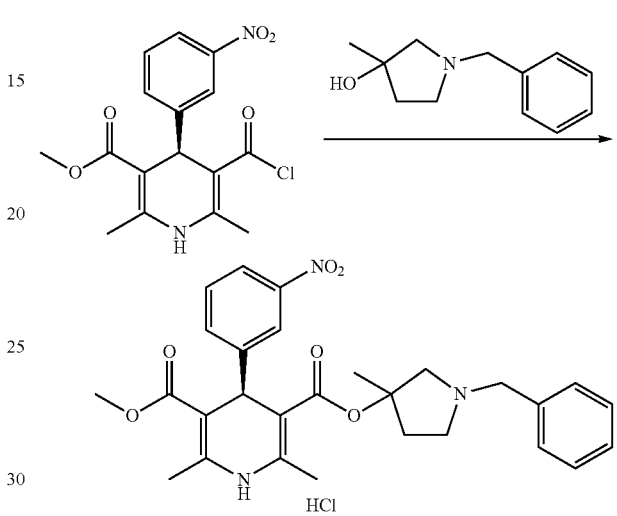

Methyl 5-chlorocarbonyl-2,6-dimethyl-4-(3-nitrophenyl)-1,4-dihydropyridine-3-carboxylate (1.0 g, 2.85 mmol) was added dropwisely to a solution of 1-benzyl-3-methylpyrrolidin-3-ol (0.6 g, 3 mmol) in dichloromethane at −25° C. After the completion of the dropwise addition, the mixture was moved to room temperature. The stirring was continued for 12 hours. After the completion of reaction, the reaction solution was rotary evaporated to dryness, and purified by column chromatography (silica gel column, eluted with petroleum ether: ethyl acetate=10:1 (volumetric ratio)) to obtain a solid. The resulting solid was dissolved in dichloromethane. To the resulting solution was introduced an HCl gas. The resulting mixture was rotary evaporated to dryness to produce the target product (0.4 g) in a yield of 27.8%.

Example 13

Preparation of (4S)-3-(1-benzyl-3-methylpyrrolidin-3-yl) 5-methyl 2,6-dimethyl-4-(3-nitrophenyl)-1,4-dihydropyridine-3,5-dicarboxylate (Compound 13)

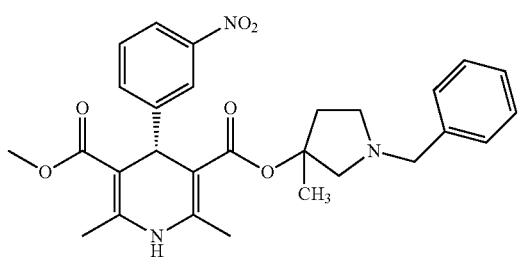 [SMILES: COC(=O)C1=C(C)NC(C)=C(C(=O)OC2(C)CCN(Cc3ccccc3)C2)[C@H]1c1cccc([N+](=O)[O-])c1]

The steps in Example 12 were repeated, except that (S)-5-methoxycarbonyl-2,6-dimethyl-4-(3-nitrophenyl)-1,4-dihydropyridine-3-carboxylic acid in step (3) was replaced with (R)-5-methoxycarbonyl-2,6-dimethyl-4-(3-nitrophenyl)-1,4-dihydropyridine-3-carboxylic acid.

(R)-5-methoxycarbonyl-2,6-dimethyl-4-(3-nitrophenyl)-1,4-dihydropyridine-3-carboxylic acid was prepared with reference to the step (1) of Example 15.

Example 14

Preparation of (4R)-3-[1-(3,3-diphenylpropyl)-3-methylpyrrolidin-3-yl]5-methyl 2,6-dimethyl-4-(3-nitrophenyl)-1,4-dihydropyridine-3,5-dicarboxylate (Compound 14)

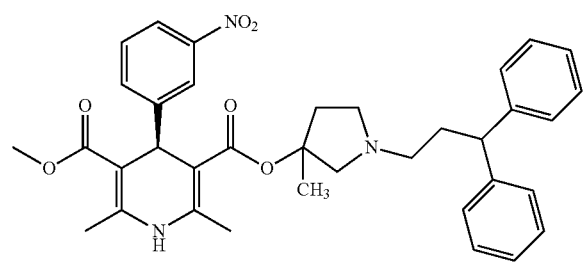 [SMILES: COC(=O)C1=C(C)NC(C)=C(C(=O)OC2(C)CCN(CCC(c3ccccc3)c3ccccc3)C2)[C@@H]1c1cccc([N+](=O)[O-])c1]

The steps in Example 15 were repeated, except that (R)-5-methoxycarbonyl-2,6-dimethyl-4-(3-nitrophenyl)-1,4-dihydropyridine-3-carboxylic acid in step (5) was replaced with (S)-5-methoxycarbonyl-2,6-dimethyl-4-(3-nitrophenyl)-1,4-dihydropyridine-3-carboxylic acid.

(R)-5-methoxycarbonyl-2,6-dimethyl-4-(3-nitrophenyl)-1,4-dihydropyridine-3-carboxylic acid was prepared with reference to the step (1) of Example 12.

Example 15

Preparation of (4S)-3-[1-(3,3-diphenylpropyl)-3-methylpyrrolidin-3-yl]5-methyl 2,6-dimethyl-4-(3-nitrophenyl)-1,4-dihydropyridine-3,5-dicarboxylate (Compound 15)

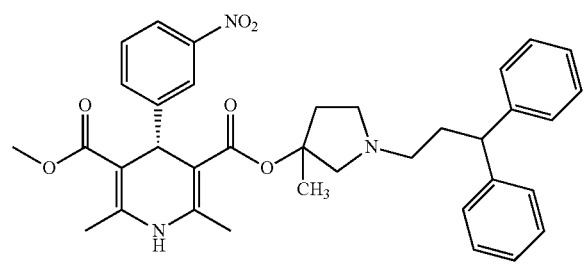 [SMILES: COC(=O)C1=C(C)NC(C)=C(C(=O)OC2(C)CCN(CCC(c3ccccc3)c3ccccc3)C2)[C@H]1c1cccc([N+](=O)[O-])c1]

(1) Preparation of (R)-5-(methoxycarbonyl)-2,6-dimethyl-4-(3-nitrophenyl)-1,4-dihydropyridine-3-carboxylic acid

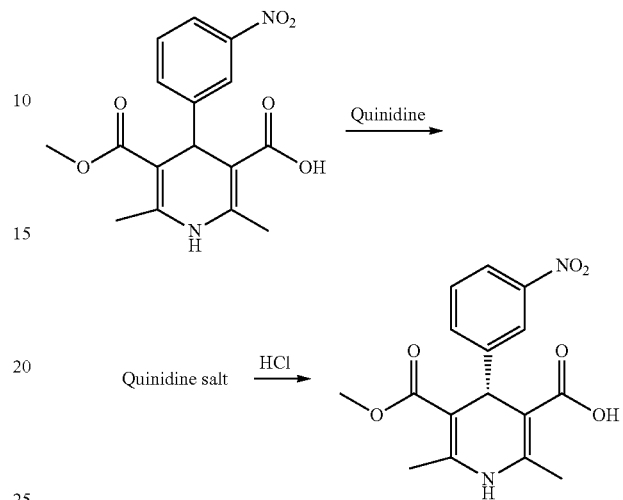

To a solution of 5-(methoxycarbonyl)-2,6-dimethyl-4-(3-nitrophenyl)-1,4-dihydropyridine-3-carboxylic acid (700 g, 2.1 mol) in methanol (14 L) was added Quinidine (617 g, 1.90 mol). The mixture was stirred at 90° C. under reflux until Quinidine was completely dissolved. The stirring was continued for 3 hours. 4.5 L water was added. The stirring was continued for 0.5 hour. The mixture was cooled down slowly. A solid was precipitated out and was filtered. The filter cake was treated with hydrochloric acid to produce (R)-5-(methoxycarbonyl)-2,6-dimethyl-4-(3-nitrophenyl)-1,4-dihydropyridine-3-carboxylic acid (130 g) in a yield of 18.6%.

(2) Preparation of tert-butyl 3-hydroxy-3-methylpyrrolidine-1-carboxylate

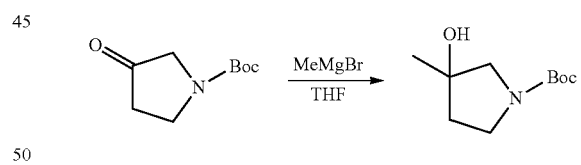

To a 30 L reaction kettle was added 4 L dry THF at −10° C. After stirring, to the mixture were added $ZnCl_2$ (118 g, 0.86 mol) and LiCl (402 g, 9.5 mol). After half an 0.5 hour, to the resulting mixture was slowly added a solution of MeMgBr (3 mol/L) in diethyl ether (6.4 L, 19.2 mol) dropwisely. The stirring was continued for half an hour. To the resulting mixture was slowly added a solution of tert-butyl 3-oxopyrrolidine-1-carboxylate (1600 g, 8.6 mol) in THF dropwisely. After the completion of reaction by HPLC detection, to the system was dropwisely added a saturated $NH_4Cl$ solution to quench off the reaction. The reaction was extracted with ethyl acetate. The organic phase was washed with a saturated aqueous NaCl solution, dried over anhydrous sodium sulfate, and evaporated to remove the solvent to produce tert-butyl 3-hydroxy-3-methylpyrrolidine-1-carboxylate as a pale yellow solid (1450 g) in a yield of 83.8%.

(3) Preparation of 3-methylpyrrolidin-3-ol hydrochloride

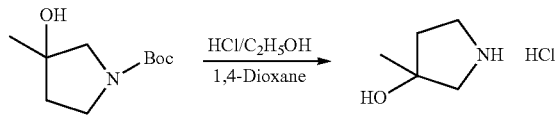

To a 10 L three-opening flask were added 5 L 1,4-dioxane and tert-butyl 3-hydroxy-3-methylpyrrolidine-1-carboxylate (1450 g, 7.2 mol) under cooling in an ice bath. After stirring, to the resulting mixture was slowly added 2.2 L HCl/ethanol solution (30%) dropwisely. After the completion of addition, the reaction was conducted at 25° C. for 12 hours. After the completion of reaction monitored by TLC, the reaction was filtered by suction to produce 3-methylpyrrolidin-3-ol hydrochloride as a red-brown solid (750 g) in a yield of 75.6%.

(4) Preparation of 3,3-diphenyl-1-propanol

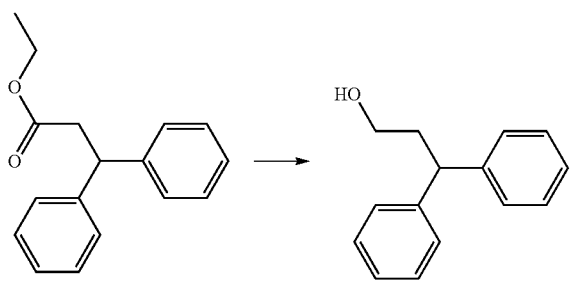 [SMILES: CCOC(=O)CC(c1ccccc1)c1ccccc1 ; OCCC(c1ccccc1)c1ccccc1]

To a 30 L reaction kettle was slowly added a solution of diisobutylaluminum hydride in toluene (15 L, 1 mol/L) at −20° C. After stirring, to the resulting mixture was slowly added a solution of ethyl 3,3-diphenyl-1-propanate (1200 g, 4.7 mol) in dichloromethane dropwisely. After the completion of dropwise addition, the reaction was conducted at 25° C. for 12 hours. After the completion of reaction monitored by TLC, the reaction solution was divided into three parts. 200 mL methanol and 1000 mL water were slowly added respectively at −20° C. to quench off the reaction. The reaction solutions were combined and extracted with dichloromethane. The organic phase was dried over anhydrous sodium sulfate, and evaporated to remove the solvent to produce an oily crude product of 3,3-diphenyl-1-propanol (1000 g), which was directly used in the next reaction.

(5) Preparation of 3,3-diphenylpropyl methanesulfonate

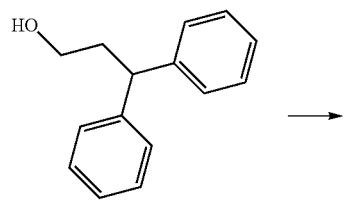

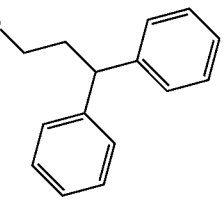

3,3-diphenyl-1-propanol (1000 g, 4.7 mol) was dissolved in 3 L dichloromethane. To the mixture was added triethylamine (712 g, 7.05 mol). After stirring at 0° C. for half an hour, to the resulting mixture was slowly added MsCl (645 g, 5.64 mol) dropwisely. The reaction was conducted at 25° C. After the completion of reaction monitored by TLC, the reaction solution was washed with water thrice. The organic phase was dried over anhydrous sodium sulfate, and evaporated to remove the solvent to produce an oily crude product. To the crude product was added isopropanol. The resulting mixture was filtered by suction to produce 3,3-diphenylpropyl methanesulfonate as a solid (1000 g) in a yield of 73% (two steps together).

(6) Preparation of 1-(3,3-diphenylpropyl)-3-methylpyrrolidin-3-ol

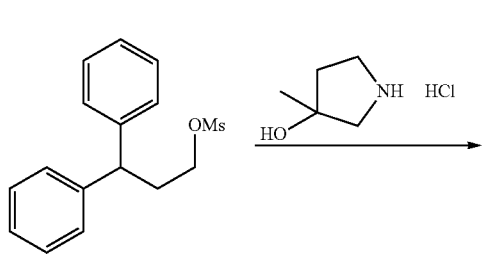

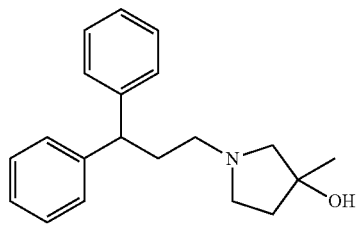

To a 10 L reaction flask were added 3-methylpyrrolidin-3-ol hydrochloride (616 g, 4.48 mol), anhydrous potassium carbonate (1186 g, 8.6 mol) and acetonitrile (5 L). To the resulting mixture was slowly added a solution of 3,3-diphenylpropyl methanesulfonate (1000 g, 3.45 mol) in acetonitrile dropwisely at 85° C. The reaction was conducted for 12 hours. After the completion of reaction monitored by TLC, the reaction solution was evaporated under reduced pressure to remove acetonitrile. A mixed solution of dichloromethane and water was added for extraction. The organic phase was dried over anhydrous sodium sulfate, and evaporated to remove the solvent to produce a crude product, which was purified by column chromatography (silica gel column, eluted with petroleum ether: ethyl acetate=50:1 (volumetric ratio)) to produce 1-(3,3-diphenylpropyl)-3-methylpyrrolidin-3-ol (580 g) in a yield of 57%.

(7) Preparation of (4S)-3-[1-(3,3-diphenylpropyl)-3-methylpyrrolidin-3-yl]5-methyl 2,6-dimethyl-4-(3-nitrophenyl)-1,4-dihydropyridine-3,5-dicarboxylate

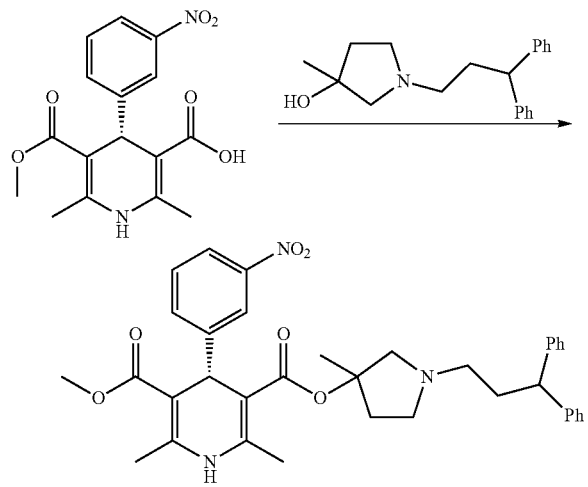

To a solution of (R)-5-methoxycarbonyl-2,6-dimethyl-4-(3-nitrophenyl)-1,4-dihydropyridine-3-carboxylic acid (67.5 g, 0.2 mol) in dichloromethane was added 1.5 mL DMF. To the mixture was slowly added oxalyl chloride (51 g, 0.4 mol) dropwisely in an ice bath. The reaction was conducted at 25° C. After the completion of reaction, the resulting mixture was evaporated under reduced pressure to remove oxalyl chloride. To the reaction flask were slowly added dichloromethane (300 mL), 1-(3,3-diphenylpropyl)-3-methylpyrrolidin-3-ol (29.5 g, 0.1 mol) and DIPEA (25.8 g, 0.2 mol) dropwisely under cooling in an ice bath respectively and successively. The reaction was conducted at 25° C. After the completion of reaction monitored by HPLC, the reaction solution was washed with water thrice. The organic phase was dried over sodium sulfate, and filtered by suction. The filtrate was evaporated to dryness, and purified by column chromatography (silica gel column, eluted with petroleum ether: ethyl acetate=80:1 (volumetric ratio)) to produce S)-3-[1-(3,3-diphenylpropyl)-3-methylpyrrolidin-3-yl]5-methyl 2,6-dimethyl-4-(3-nitrophenyl)-1,4-dihydropyridine-3,5-dicarboxylate (34 g) in a yield of 56%.

Example 16

Preparation of (S)-3-[(S)-1-(3,3-diphenylpropyl)-3-methylpyrrolidin-3-yl]5-methyl 2,6-dimethyl-4-(3-nitrophenyl)-1,4-dihydropyridine-3,5-dicarboxylate (Compound 16)

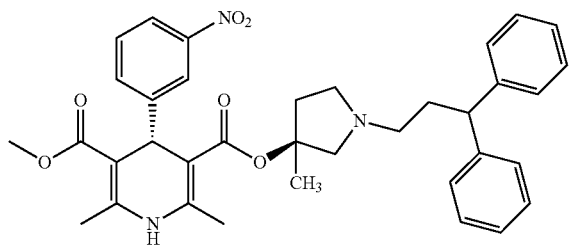 [SMILES: COC(=O)C1=C(C)NC(C)=C(C(=O)O[C@@]2(C)CCN(CCC(c3ccccc3)c3ccccc3)C2)[C@H]1c1cccc([N+](=O)[O-])c1]

(1) Preparation of (S)-1-(3,3-diphenylpropyl)-3-methylpyrrolidin-3-ol

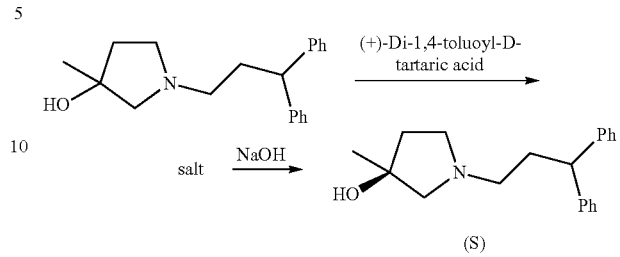

According to Example 15, (R)-5-(methoxycarbonyl)-2,6-dimethyl-4-(3-nitrophenyl)-1,4-dihydropyridine-3-carboxylic acid and 1-(3,3-diphenylpropyl)-3-methylpyrrolidin-3-ol were synthesized. To a solution of D-bis(paramethylbenzoyl) tartaric acid ((+)-Di-1,4-toluoyl-D-tartaric acid) (280 g, 0.7 mol) in isopropanol (300 mL) was added a solution of 1-(3, 3-diphenylpropyl)-3-methylpyrrolidin-3-ol (280 g, 0.95 mol) in isopropanol (300 mL) at 90° C. After the solution became clear, the solution was cooled down to 30° C. slowly, and filtered to produce a white solid, which was treated with sodium hydroxide to produce (S)-1-(3,3-diphenylpropyl)-3-methylpyrrolidin-3-ol (52 g) in a yield of 18.6%.

(2) Preparation of (S)-3-[(S)-1-(3,3-diphenylpropyl)-3-methylpyrrolidin-3-yl]5-methyl 2,6-dimethyl-4-(3-nitrophenyl)-1,4-dihydropyridine-3,5-dicarboxylate

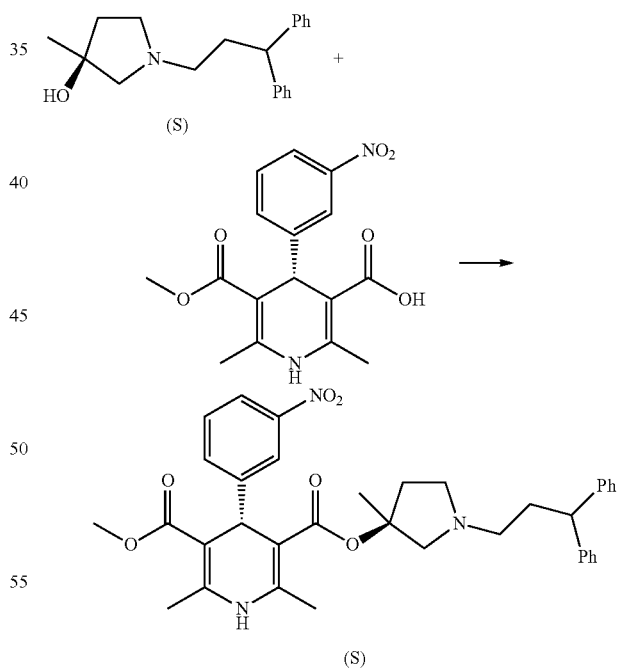

According to Example 15, (R)-5-methoxycarbonyl-2,6-dimethyl-4-(3-nitrophenyl)-1,4-dihydropyridine-3-carboxylic acid was synthesized. To a solution of (R)-5-methoxycarbonyl-2,6-dimethyl-4-(3-nitrophenyl)-1,4-dihydropyridine-3-carboxylic acid (33.75 g, 0.1 mol) in dichloromethane was added 1 mL DMF. To the resulting mixture was slowly added oxalyl chloride (25.5 g, 0.2 mol) dropwisely under cooling in an ice bath. The reaction was conducted at 25° C. After the completion of reaction, the reaction solution was evaporated under reduced pressure to remove oxalyl chloride. To the reaction flask were slowly added dichloromethane (200 mL), (S)-1-(3,3-diphenylpropyl)-3-methylpyrrolidin-3-ol (14.75 g, 0.05 mol) and DIPEA (12.9 g, 0.1 mol) dropwisely under cooling in an ice bath respectively and successively. The reaction was conducted at 25° C. After the completion of reaction monitored by HPLC, the reaction solution was washed with water thrice. The organic phase was dried over anhydrous sodium sulfate, and filtered by suction. The filtrate was evaporated to dryness, and purified by column chromatography (silica gel column, eluted with petroleum ether: ethyl acetate=80:1 (volumetric ratio)) to produce the title product (S)-3-[(S)-1-(3,3-diphenylpropyl)-3-methyl-3-pyrrolidinyl]5-methyl 2,6-dimethyl-4-(3-nitrophenyl)-1,4-dihydropyridine-3,5-dicarboxylate (17 g) in a yield of 56%. Four batches of product samples were measured for the optical activities, which were in a range of from +98° to +118° (temperature: 20° C., concentration: 2 mg/mL, the solvent was MeOH), wherein one batch of samples had an optical activity of +108.34°. The test sample Compound 16 in the following pharmacological activity assay was the sample having an optical activity of +108.34°.

Molecular formula: $C_{36}H_{39}N_3O_6$ Mw: 609.2 MS (M+H): 610.3

$^1$H-NMR (DMSO, 400 MHz) δ: 9.13-9.11 (1H, d), 8.05-7.94 (2H, m), 7.61-7.49 (2H, m), 7.33-7.27 (8H, m), 7.20-7.17 (2H, m), 4.93-4.88 (1H, d), 4.00-3.95 (1H, m), 3.95-3.53 (1H, m), 3.53-3.52 (3H, d), 3.13 (2H, m), 2.84-2.83 (4H, m), 2.42-2.36 (3H, m), 2.27-2.21 (6H, m), 2.23-2.21 (1H, m), 1.49-1.41 (3H, d).

Example 17

Preparation of (S)-3-[(R)-1-(3,3-diphenylpropyl)-3-methylpyrrolidin-3-yl]5-methyl 2,6-dimethyl-4-(3-nitrophenyl)-1,4-dihydropyridine-3,5-dicarboxylate (Compound 17)

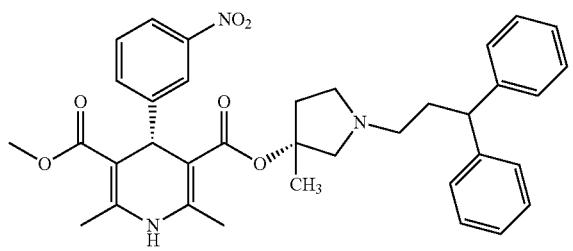 [SMILES: COC(=O)C1=C(C)NC(C)=C(C(=O)O[C@]2(C)CCN(CCC(c3ccccc3)c3ccccc3)C2)[C@H]1c1cccc([N+](=O)[O-])c1]

(1) Preparation of (R)-1-(3,3-diphenylpropyl)-3-methylpyrrolidin-3-ol

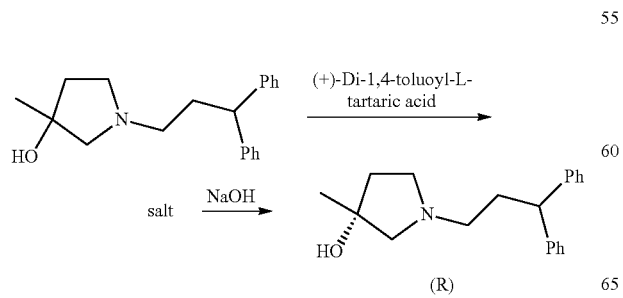

According to Example 15, (R)-5-(methoxycarbonyl)-2,6-dimethyl-4-(3-nitrophenyl)-1,4-dihydropyridine-3-carboxylic acid and 1-(3,3-diphenylpropyl)-3-methylpyrrolidin-3-ol were synthesized.

Said compound was salified with L-bis(paramethylbenzoyl)tartaric acid, and then treated with NaOH to produce the product in R-configuration, i.e. (R)-1-(3,3-diphenylpropyl)-3-methylpyrrolidin-3-ol.

(2) Preparation of (S)-3-[(R)-1-(3,3-diphenylpropyl)-3-methylpyrrolidin-3-yl]5-methyl 2,6-dimethyl-4-(3-nitrophenyl)-1,4-dihydropyridine-3,5-dicarboxylate

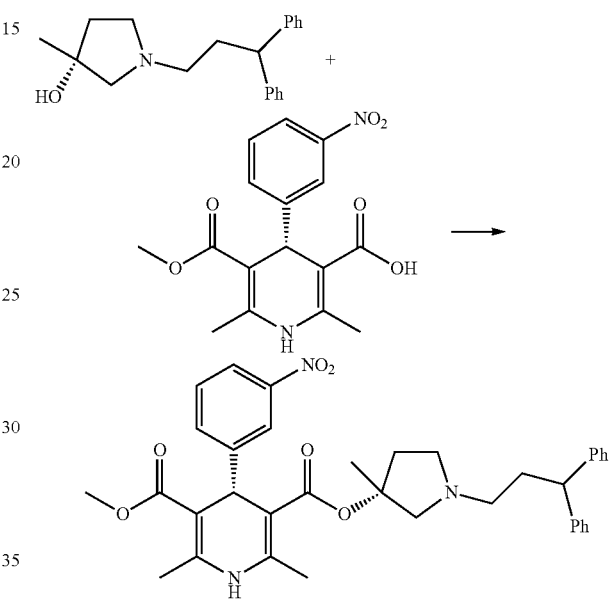

According to Example 16, (S)-3-[(R)-1-(3,3-diphenylpropyl)-3-methylpyrrolidin-3-yl]5-methyl 2,6-dimethyl-4-(3-nitrophenyl)-1,4-dihydropyridine-3,5-dicarboxylate was synthesized, wherein the reactant (S)-1-(3,3-diphenylpropyl)-3-methylpyrrolidin-3-ol was replaced with (R)-1-(3,3-diphenylpropyl)-3-methylpyrrolidin-3-ol in a yield of 45%, having an optical activity of +36.4° (temperature: 20° C., concentration: 2 mg/mL, the solvent was MeOH).

Example 18

Preparation of (4S)-3-[1-(2,2-diphenylethyl)-3-methylpyrrolidin-3-yl]5-methyl 2,6-dimethyl-4-(3-nitrophenyl)-1,4-dihydropyridine-3,5-dicarboxylate (Compound 18)

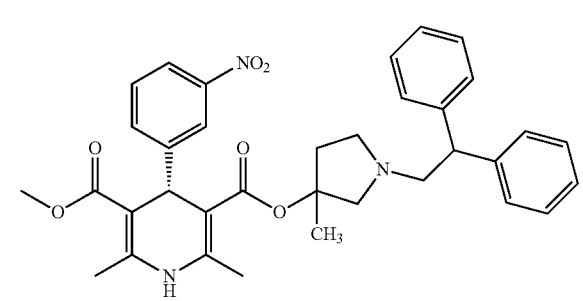

(1) Preparation of methyl 2,2-diphenylacetate

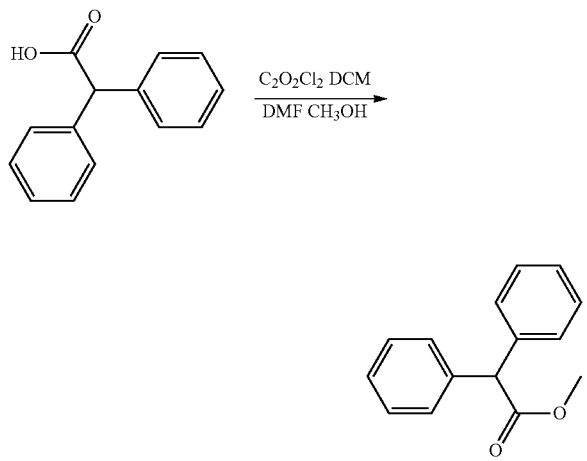

To a 500 mL three-opening flask were added 2,2-diphenylacetic acid (20 g, 94 mmol) and 200 mL dichloromethane. After stirring, 1 mL DMF was added. To the mixture was slowly added oxalyl chloride (13.16 g, 104 mmol) dropwisely in an ice bath. The reaction was conducted at 25° C. After the completion of reaction, the mixture was evaporated under reduced pressure to remove oxalyl chloride. To the reaction flask were slowly added dichloromethane (100 mL) and anhydrous methanol (3.61 g, 113 mmol) dropwisely under cooling in an ice bath respectively. The reaction was conducted at 25° C. After the completion of reaction, the reaction solution was washed with a saturated aqueous NaCl solution. The organic phase was dried over sodium sulfate, and filtered by suction. The filtrate was evaporated to dryness to produce methyl 2,2-diphenylacetate (21 g) in a yield of 98.7%.

(2) Preparation of 2,2-diphenylethanol

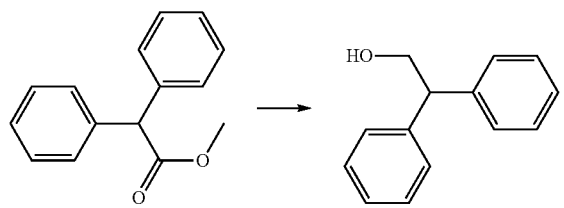 [SMILES: COC(=O)C(c1ccccc1)c1ccccc1 ; OCC(c1ccccc1)c1ccccc1]

To a 500 mL three-opening flask was slowly added a solution of diisobutylaluminum hydride in toluene (282 mL, 1 mol/L) at −30° C. After stirring, to the resulting mixture was slowly added a solution of methyl 2,2-diphenylacetate (21 g, 92.8 mmol) in dichloromethane dropwisely. After the completion of dropwise addition, the reaction was conducted at 25° C. for 12 hours. After the completion of reaction monitored by TLC, to the resulting mixture was slowly added methanol (10 mL), dichloromethane (100 mL) and an aqueous sodium hydroxide solution (100 mL, 1 mol/L) at −20° C. After the completion of reaction, to the reaction solution was added dichloromethane for extraction. The organic phase was washed with water, dried over anhydrous sodium sulfate, and evaporated to remove the solvent to produce 2,2-diphenyl ethanol (17 g) in a yield of 92.4%.

(3) Preparation of 2,2-diphenylethyl methanesulfonate

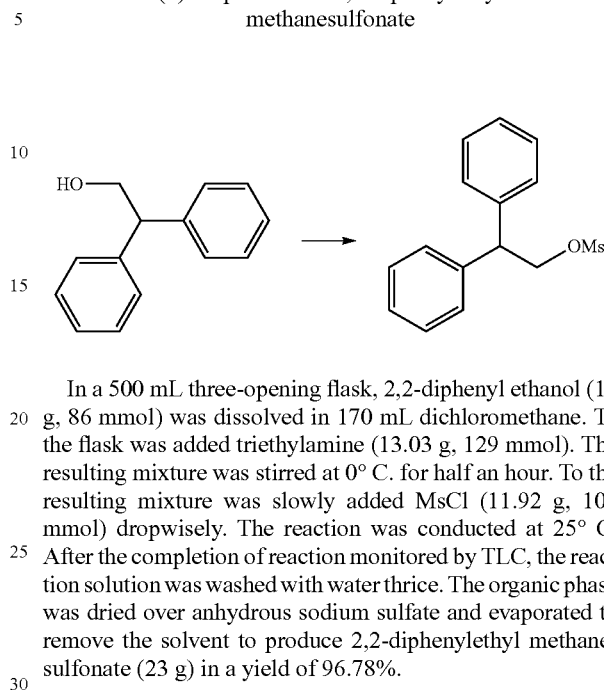

In a 500 mL three-opening flask, 2,2-diphenyl ethanol (17 g, 86 mmol) was dissolved in 170 mL dichloromethane. To the flask was added triethylamine (13.03 g, 129 mmol). The resulting mixture was stirred at 0° C. for half an hour. To the resulting mixture was slowly added MsCl (11.92 g, 104 mmol) dropwisely. The reaction was conducted at 25° C. After the completion of reaction monitored by TLC, the reaction solution was washed with water thrice. The organic phase was dried over anhydrous sodium sulfate and evaporated to remove the solvent to produce 2,2-diphenylethyl methanesulfonate (23 g) in a yield of 96.78%.

(4) Preparation of 1-(2,2-diphenylethyl)-3-methylpyrrolidin-3-ol

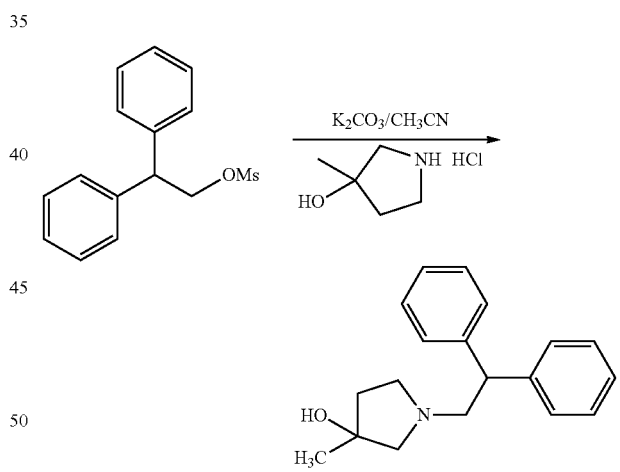

According to Example 15, 3-methylpyrrolidin-3-ol hydrochloride was synthesized. To a 500 mL reaction flask were added 3-methylpyrrolidin-3-ol hydrochloride (11.46 g, 83 mmol), anhydrous potassium carbonate (28.75 g, 208 mmol) and acetonitrile (220 mL). To the resulting mixture was slowly added a solution of 2,2-diphenylethyl methanesulfonate (23 g, 83 mmol) in acetonitrile dropwisely at 85° C. The reaction was conducted for 12 hours. After the completion of reaction monitored by TLC, the resulting mixture was evaporated under reduced pressure to remove acetonitrile. A mixed solution of dichloromethane and water was added for extraction. The organic phase was dried over anhydrous sodium sulfate, and evaporated to remove the solvent to produce a crude product. The crude product was purified by column chromatography (silica gel column, eluted with petroleum ether:ethyl acetate=30:1 (volumetric ratio)) to produce 1-(2,2-diphenylethyl)-3-methylpyrrolidin-3-ol (13.6 g) in a yield of 58.23%.

(5) Preparation of (4S)-3-[1-(2,2-diphenylethyl)-3-methylpyrrolidin-3-yl]5-methyl 2,6-dimethyl-4-(3-nitrophenyl)-1,4-dihydropyridine-3,5-dicarboxylate

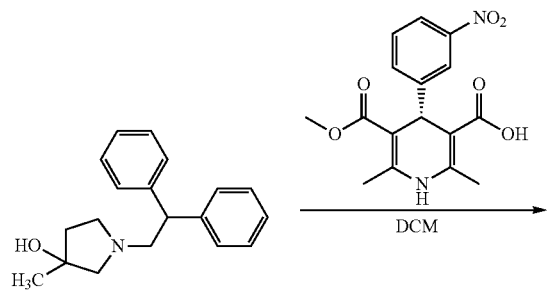

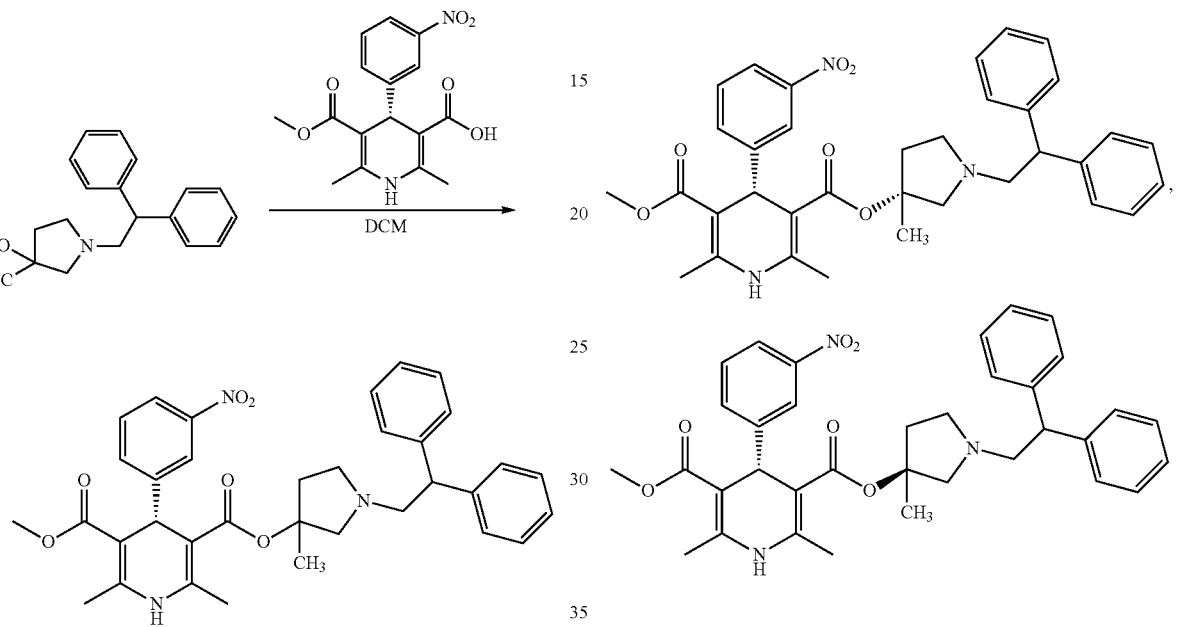

According to Example 15, (R)-5-methoxycarbonyl-2,6-dimethyl-4-(3-nitrophenyl)-1,4-dihydropyridine-3-carboxylic acid was synthesized. To a solution of (R)-5-methoxycarbonyl-2,6-dimethyl-4-(3-nitrophenyl)-1,4-dihydropyridine-3-carboxylic acid (17.67 g, 53 mmol) in dichloromethane was added 1 mL DMF. To the resulting mixture was slowly added oxalyl chloride (8.1 g, 64 mmol) dropwisely under cooling in an ice bath. The reaction was conducted at 25° C. After the completion of reaction, the resulting mixture was evaporated under reduced pressure to remove oxalyl chloride. To the reaction flask were slowly added dichloromethane (120 mL), 1-(2,2-diphenylethyl)-3-methylpyrrolidin-3-ol (13.6 g, 48 mmol) and DIPEA (12.38 g, 96 mmol) dropwisely under cooling in an ice bath respectively and successively. The reaction was conducted at 25° C. After the completion of reaction monitored by HPLC, the reaction solution was washed with water thrice. The organic phase was dried over sodium sulfate, and filtered by suction. The filtrate was evaporated to dryness, and purified by column chromatography (silica gel column, eluted with petroleum ether: ethyl acetate=70:1 (volumetric ratio)) to produce (4S)-3-[1-(2,2-diphenylethyl)-3-methylpyrrolidin-3-yl]5-methyl 2,6-dimethyl-4-(3-nitrophenyl)-1,4-dihydropyridine-3,5-dicarboxylate (14.58 g) in a yield of 51%.

Molecular formula: $C_{35}H_{37}N_3O_6$ Mw: 595.2 MS (M+H): 596.3

$^1$H-NMR (DMSO, 400 MHz) δ: 9.16 (1H, s), 7.99-7.91 (2H, m), 7.57-7.51 (2H, m), 7.49-7.34 (8H, m), 7.32-7.23 (2H, m), 4.89-4.83 (1H, d), 4.52 (1H, s), 3.96-3.53 (2H, m), 3.52-3.33 (5H, m), 3.26-3.23 (2H, m), 2.26-2.23 (7H, m), 1.98-1.91 (1H, m), 1.42-1.26 (3H, m).

Example 19

Preparation of (S)-3-[(R/S)-1-(2,2-diphenylethyl)-3-methylpyrrolidin-3-yl]5-methyl 2,6-dimethyl-4-(3-nitrophenyl)-1,4-dihydropyridine-3,5-dicarboxylate (Compound 19 and Compound 20)

Compound 18 was subjected to a chiral isomer separation with a Daicel chiral column according to the HPLC method, which was assigned to Daicel Chiral Technologies (China) Co., Ltd (Shanghai). The corresponding fractions were collected and rotary evaporated to remove the solvent to produce pure optical isomers: Compound 19 and Compound 20. The separation conditions were as follows:

Compound 19:
Chiral column type: CHIRALCEL OD-H
Chiral column size: 0.46 cm I.D.×15 cm L
Mobile phase: $CO_2$/MeOH/DEA=80/20/0.1 (V/V/V)
Wave length for detection: UV 220 nm
Column temperature: 35° C.
Retention time: 7.333 minutes;
and
Compound 20:
Chiral column type: CHIRALCEL OD-H
Chiral column size: 0.46 cm I.D.×15 cm L
Mobile phase: $CO_2$/MeOH/DEA=80/20/0.1 (V/V/V)
Wave length for detection: UV 220 nm
Column temperature: 35° C.
Retention time: 8.493 minutes.
Optical activity measurement:
Compound 19: dissolved in DMSO, at a concentration of 20 mg/ml, at a temperature of 20° C., the measured optical activity was −3.7°;
Compound 20: dissolved in DMSO, at a concentration of 20 mg/ml, at a temperature of 20° C., the measured optical activity was +35.2°.

Example 20

Preparation of (4S)-3-[3-methyl-1-(3-phenylpropyl)pyrrolidin-3-yl]5-methyl 2,6-dimethyl-4-(3-nitrophenyl)-1,4-dihydropyridine-3,5-dicarboxylate (Compound 21)

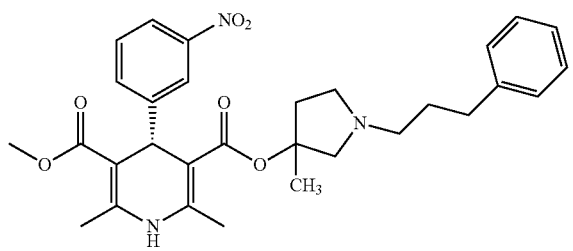 [SMILES: COC(=O)C1=C(C)NC(C)=C(C(=O)OC2(C)CCN(CCCc3ccccc3)C2)[C@H]1c1cccc([N+](=O)[O-])c1]

(1) Preparation of 3-methyl-1-(3-phenylpropyl)pyrrolidin-3-ol

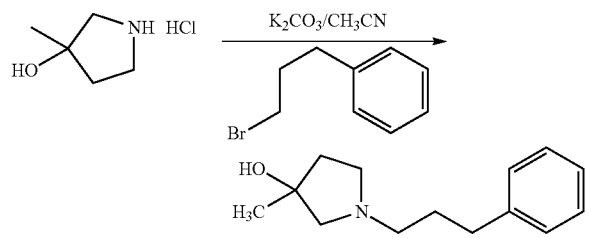

According to Example 15, 3-methylpyrrolidin-3-ol hydrochloride was synthesized. To a 100 mL reaction flask were added 3-methylpyrrolidin-3-ol hydrochloride (1 g, 7.2 mmol), anhydrous potassium carbonate (2.5 g, 18 mmol) and acetonitrile (15 mL). To the resulting mixture was slowly added a solution of 3-bromopropylbenzene (1.29 g, 6.48 mmol) in acetonitrile dropwise at 85° C. The reaction was conducted for 12 hours. After the completion of reaction monitored by TLC, the resulting mixture was evaporated under reduced pressure to remove acetonitrile. To the residue was added a mixed solution of dichloromethane and water for extraction. The organic phase was dried over anhydrous sodium sulfate, and evaporated to remove the solvent to produce a crude product. The crude product was purified by column chromatography (silica gel column, eluted with petroleum ether: ethyl acetate=10:1 (volumetric ratio)) to produce 3-methyl-1-(3-phenylpropyl)pyrrolidin-3-ol (1 g) in a yield of 70.4%.

(2) Preparation of (4S)-3-[3-methyl-1-(3-phenylpropyl)pyrrolidin-3-yl]5-methyl 2,6-dimethyl-4-(3-nitrophenyl)-1,4-dihydropyridine-3,5-dicarboxylate

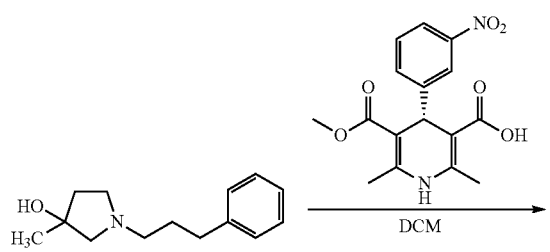

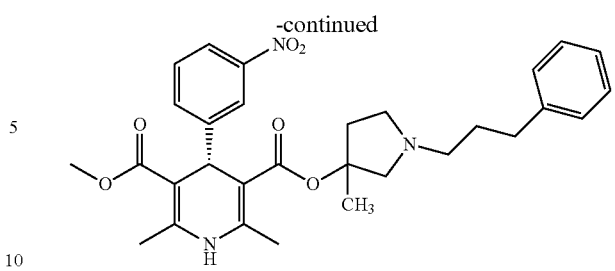

According to Example 15, (R)-5-methoxycarbonyl-2,6-dimethyl-4-(3-nitrophenyl)-1,4-dihydropyridine-3-carboxylic acid was synthesized. To a solution of (R)-5-methoxycarbonyl-2,6-dimethyl-4-(3-nitrophenyl)-1,4-dihydropyridine-3-carboxylic acid (2.72 g, 8.18 mmol) in dichloromethane was added 0.1 mL DMF. To the resulting mixture was slowly added oxalyl chloride (2.08 g, 16.39 mmol) dropwisely under cooling in an ice bath. The reaction was conducted at 25° C. After the completion of reaction, the resulting mixture was evaporated under reduced pressure to remove oxalyl chloride. To the reaction flask were slowly added dichloromethane (20 mL), 3-methyl-1-(3-phenylpropyl)pyrrolidin-3-ol (1 g, 4.56 mmol) and DIPEA (1.46 g, 11.30 mmol) dropwisely under cooling in an ice bath respectively and successively. The reaction was conducted at 25° C. After the completion of reaction monitored by HPLC, the reaction solution was washed with water thrice. The organic phase was dried over sodium sulfate, and filtered by suction. The filtrate was evaporated to dryness, and purified by column chromatography (silica gel column, eluted with petroleum ether:ethyl acetate=87:1 (volumetric ratio)) to produce (4S)-3-[3-methyl-1-(3-phenylpropyl)pyrrolidinyl-3-yl]5-methyl 2,6-dimethyl-4-(3-nitrophenyl)-1,4-dihydropyridine-3,5-dicarboxylate (1.15 g) in a yield of 47.3%.

Molecular formula: $C_{30}H_{35}N_3O_6$ Mw: 533.2 MS (M+H): 534.3

1H-NMR (DMSO, 400 MHz) δ: 9.20-9.17 (1H, d), 9.16-7.97 (2H, m), 7.63-7.53 (2H, m), 7.30-7.19 (5H, m), 4.95-4.91 (1H, m), 3.56-3.55 (1H, m), 3.54-3.41 (4H, m), 3.40-3.15 (1H, m), 3.12-3.07 (4H, m), 2.61-2.49 (2H, m), 2.29 (6H, s), 1.96-1.90 (2H, m), 1.52-1.36 (3H, dd), 1.10-1.03 (2H, m).

Example 21

Preparation of (4S)-3-(3-methyl-1-phenylethylpyrrolidin-3-yl) 5-methyl 2,6-dimethyl-4-(3-nitrophenyl)-1,4-dihydropyridine-3,5-dicarboxylate (Compound 22)

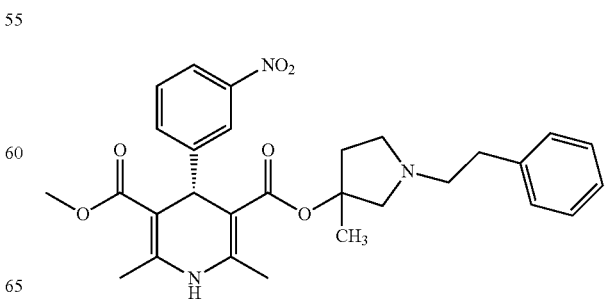

(1) Preparation of 3-methyl-1-phenylethylpyrrolidin-3-ol

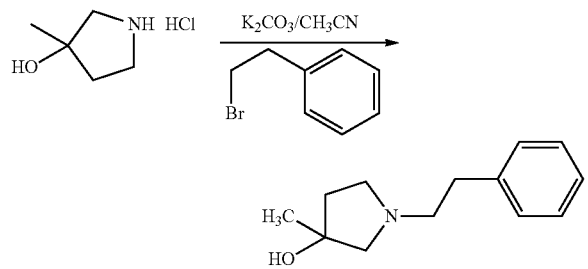

According to Example 15, 3-methylpyrrolidin-3-ol hydrochloride was synthesized. To a 100 mL reaction flask were added 3-methylpyrrolidin-3-ol hydrochloride (1 g, 7.2 mmol), anhydrous potassium carbonate (2.5 g, 18 mmol) and acetonitrile (15 mL). To the resulting mixture was slowly added a solution of 2-bromoethylbenzene (1.2 g, 6.48 mmol) in acetonitrile dropwise at 85° C. The reaction was conducted for 12 hours. After the completion of reaction monitored by TLC, the resulting mixture was evaporated under reduced pressure to remove acetonitrile. To the residue was added a mixed solution of dichloromethane and water for extraction. The organic phase was dried over anhydrous sodium sulfate, and evaporated to remove the solvent to produce a crude product. The crude product was purified by column chromatography (silica gel column, eluted with petroleum ether:ethyl acetate=30:1 (volumetric ratio)) to produce 3-methyl-1-phenylethylpyrrolidin-3-ol (1 g) in a yield of 75.2%.

(2) Preparation of (4S)-3-(3-methyl-1-phenylethylpyrrolidin-3-yl) 5-methyl 2,6-dimethyl-4-(3-nitrophenyl)-1,4-dihydropyridine-3,5-dicarboxylate

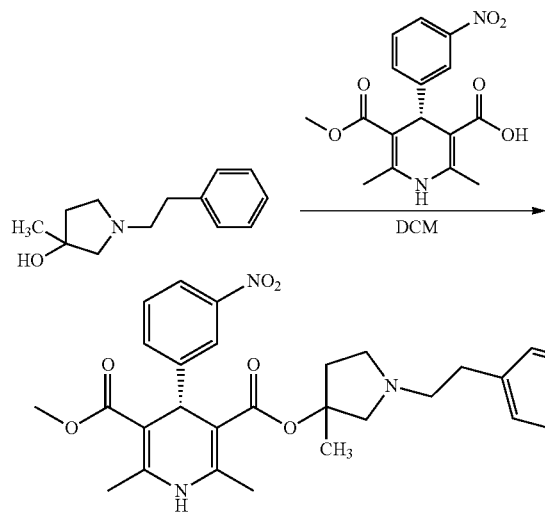

According to Example 15, (R)-5-methoxycarbonyl-2,6-dimethyl-4-(3-nitrophenyl)-1,4-dihydropyridine-3-carboxylic acid was synthesized. To a solution of (R)-5-methoxycarbonyl-2,6-dimethyl-4-(3-nitrophenyl)-1,4-dihydropyridine-3-carboxylic acid (2.9 g, 8.73 mmol) in dichloromethane was added 0.1 mL DMF. To the mixture was slowly added oxalyl chloride (2.2 g, 17.33 mmol) dropwisely in an ice bath. The reaction was conducted at 25° C. until the completion of reaction. The resulting mixture was evaporated under reduced pressure to remove oxalyl chloride. To the reaction flask were slowly added dichloromethane (20 mL), 3-methyl-1-phenylethylpyrrolidin-3-ol (1 g, 4.87 mmol) and DIPEA (1.56 g, 12.1 mmol) dropwisely under cooling in an ice bath respectively and successively. The reaction was conducted at 25° C. After the completion of reaction monitored by HPLC, the reaction solution was washed with water thrice. The organic phase was dried over sodium sulfate, and filtered by suction. The filtrate was evaporated to dryness, and purified by column chromatography (silica gel column, eluted with petroleum ether:ethyl acetate=78:1 (volumetric ratio)) to produce (4S)-3-(3-methyl-1-phenylethylpyrrolidin-3-yl) 5-methyl 2,6-dimethyl-4-(3-nitrophenyl)-1,4-dihydropyridine-3,5-dicarboxylate (1.21 g) in a yield of 48%.

Molecular formula: $C_{29}H_{33}N_3O_6$ Mw: 519.2 MS (M+H): 520.3

$^1$H-NMR (DMSO, 400 MHz) δ: 9.20-9.18 (1H, d), 8.03-7.97 (2H, m), 7.64-7.53 (2H, m), 7.34-7.21 (5H, m), 4.96-4.93 (1H, d), 3.56-3.54 (2H, m), 3.52-3.41 (3H, m), 3.34-3.17 (1H, m), 3.07-2.93 (2H, m), 2.50-2.49 (2H, m), 2.31-2.29 (6H, d), 2.26 (1H, m), 1.54-1.39 (3H, dd), 1.1 (1H, s), 1.05 (1H, t).

Example 22

Preparation of (4S)-3-[1-(3,5-difluorobenzyl)-3-methylpyrrolidin-3-yl]5-methyl 2,6-dimethyl-4-(3-nitrophenyl)-1,4-dihydropyridine-3,5-dicarboxylate (Compound 23)

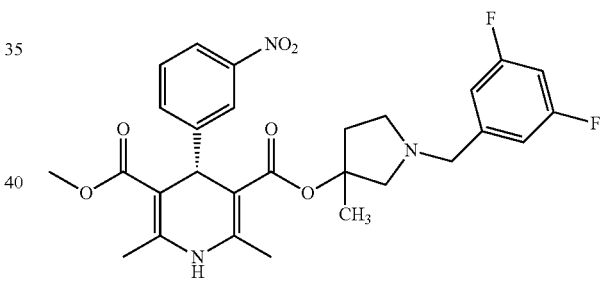

(1) Preparation of 1-(3,5-difluorobenzyl)-3-methylpyrrolidin-3-ol

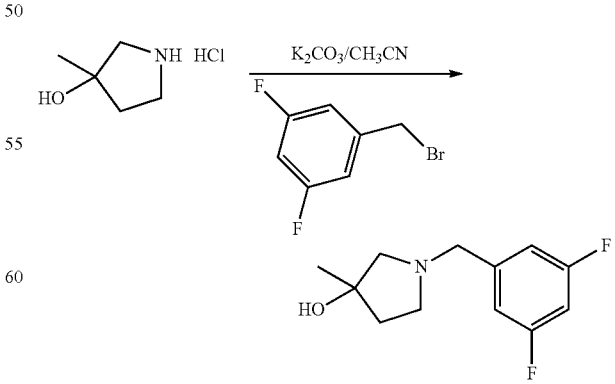

According to Example 15, 3-methylpyrrolidin-3-ol hydrochloride was synthesized. To a 100 mL reaction flask were added 3-methylpyrrolidin-3-ol hydrochloride (1 g, 7.2 mmol), anhydrous potassium carbonate (2.5 g, 18 mmol) and acetonitrile (15 mL). To the resulting mixture was slowly added a solution of 3,5-difluorobenzyl bromide (1.64 g, 7.9 mmol) in acetonitrile dropwisely at 85° C. The reaction was conducted for 12 hours. After the completion of reaction monitored by TLC, the resulting mixture was evaporated under reduced pressure to remove acetonitrile. To the residue was added a mixed solution of dichloromethane and water for extraction. The organic phase was dried over anhydrous sodium sulfate, and evaporated to remove the solvent to produce a crude product of 1-(3,5-difluorobenzyl)-3-methylpyrrolidin-3-ol (1.8 g), which was directly used in the next step.

(2) Preparation of (4S)-3-[1-(3,5-difluorobenzyl)-3-methylpyrrolidin-3-yl]5-methyl 2,6-dimethyl-4-(3-nitrophenyl)-1,4-dihydropyridine-3,5-dicarboxylate

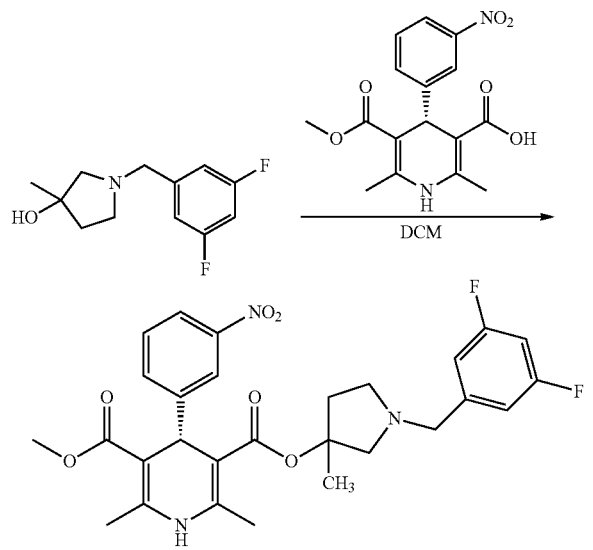

According to Example 15, (R)-5-methoxycarbonyl-2,6-dimethyl-4-(3-nitrophenyl)-1,4-dihydropyridine-3-carboxylic acid was synthesized. To a solution of (R)-5-methoxycarbonyl-2,6-dimethyl-4-(3-nitrophenyl)-1,4-dihydropyridine-3-carboxylic acid (4.86 g, 14.6 mmol) in dichloromethane was added 0.1 mL DMF. To the mixture was slowly added oxalyl chloride (3.68 g, 29.0 mmol) dropwisely in an ice bath. The reaction was conducted at 25° C. until the completion of reaction. The resulting mixture was evaporated under reduced pressure to remove oxalyl chloride. To the reaction flask were slowly added dichloromethane (20 mL), the crude product of 1-(3,5-difluorobenzyl)-3-methylpyrrolidin-3-ol (1.8 g) and DIPEA (1.86 g, 14.4 mmol) dropwisely under cooling in an ice bath respectively and successively. The reaction was conducted at 25° C. After the completion of reaction monitored by HPLC, the reaction solution was washed with water thrice. The organic phase was dried over sodium sulfate, and filtered by suction. The filtrate was evaporated to dryness, and purified by column chromatography (silica gel column, eluted with petroleum ether:ethyl acetate=85:1 (volumetric ratio)) to produce (4S)-3-[1-(3,5-difluorobenzyl)-3-methyl-3-pyrrolidin-3-yl]5-methyl 2,6-dimethyl-4-(3-nitrophenyl)-1,4-dihydropyridine-3,5-dicarboxylate (1.78 g) in a yield of 45.6% (two steps together).

Molecular formula: $C_{28}H_{29}F_2N_3O_6$ Mw: 541.2 MS (M+H): 543.3

$^1$H-NMR (DMSO, 400 MHz) δ: 9.14 (1H, t), 8.02-7.97 (2H, m), 7.60-7.55 (2H, m), 7.39-7.33 (2H, m), 4.93-4.90 (1H, d), 4.41-4.40 (2H, m), 3.56-3.53 (6H, m), 3.35 (1H, s), 3.07 (1H, s), 2.30-2.26 (6H, m), 1.50-1.24 (3H, dd), 1.10 (3H, s).

Example 23

Preparation of (4S)-3-[1-diphenylmethyl-3-methylpyrrolidin-3-yl]5-methyl 2,6-dimethyl-4-(3-nitrophenyl)-1,4-dihydropyridine-3,5-dicarboxylate (Compound 26)

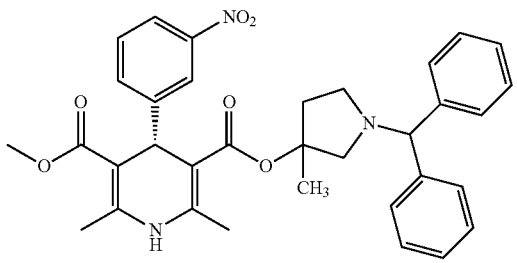 [SMILES: COC(=O)C1=C(C)NC(C)=C(C(=O)OC2(C)CCN(C(c3ccccc3)c3ccccc3)C2)[C@H]1c1cccc([N+](=O)[O-])c1]

(1) Preparation of (R)-5-(methoxycarbonyl)-2,6-dimethyl-4-(3-nitrophenyl)-1,4-dihydropyridine-3-carboxylic acid

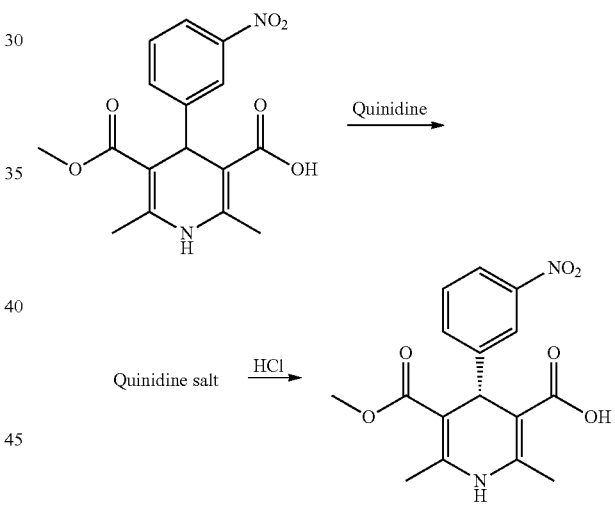

To a solution of 5-(methoxycarbonyl)-2,6-dimethyl-4-(3-nitrophenyl)-1,4-dihydropyridine-3-carboxylic acid (700 g, 2.1 mol) in methanol (14 L) was added Quinidine (617 g, 1.90 mol). The mixture was stirred at 90° C. under reflux until Quinidine was completely dissolved. The stirring was continued for 3 hours. 4.5 L water was added. The stirring was continued for half an hour. The mixture was cooled down slowly. A solid was precipitated out and was filtered. The filter cake was treated with hydrochloric acid to produce (R)-5-(methoxycarbonyl)-2,6-dimethyl-4-(3-nitrophenyl)-1,4-dihydropyridine-3-carboxylic acid (130 g) in a yield of 18.6%.

(2) Preparation of tert-butyl 3-hydroxy-3-methylpyrrolidine-1-carboxylate

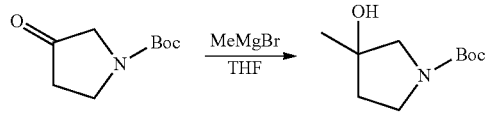

To a 30 L reaction kettle was added 4 L dry THF at −10° C. After stirring, to the mixture were added ZnCl₂ (118 g, 0.86 mol) and LiCl (402 g, 9.5 mol). After half an hour, to the resulting mixture was slowly added dropwisely a solution of MeMgBr (3 mol/L) in diethyl ether (6.4 L, 19.2 mol). The stirring was continued for half an hour. To the resulting mixture was slowly added a solution of tert-butyl 3-oxopyrrolidine-1-carboxylate (1600 g, 8.6 mol) in THF dropwisely. After the completion of reaction by HPLC detection, to the system was dropwisely added a saturated NH₄Cl solution to quench off the reaction. The reaction was extracted with ethyl acetate. The organic phase was washed with a saturated aqueous NaCl solution, dried over anhydrous sodium sulfate, and evaporated to remove the solvent to produce tert-butyl 3-hydroxy-3-methylpyrrolidine-1-carboxylate as a pale-yellow solid (1450 g) in a yield of 83.8%.

(3) Preparation of 3-methylpyrrolidin-3-ol hydrochloride

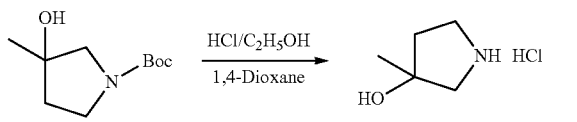

To a 10 L three-opening flask were added 1,4-dioxane (5 L) and tert-butyl 3-hydroxy-3-methylpyrrolidine-1-carboxylate (1450 g, 7.2 mol) in an ice bath. After stirring, to the resulting mixture was slowly added an HCl/ethanol solution (30%, 2.2 L) dropwisely. After the completion of addition, the reaction was conducted at 25° C. for 12 hours. After the completion of reaction monitored by TLC, the resulting mixture was filtered by suction to produce 3-methylpyrrolidin-3-ol hydrochloride as a red-brown solid (750 g) in a yield of 75.6%.

(4) Preparation of 1-(diphenylmethyl)-3-methylpyrrolidin-3-ol

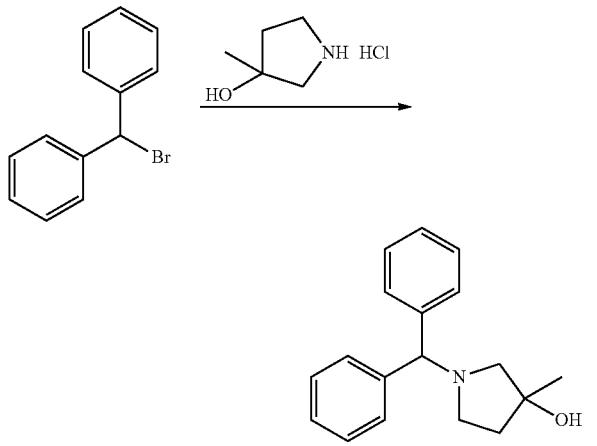

To a reaction flask were added 3-methylpyrrolidin-3-ol hydrochloride (1 g, 7.2 mmol), anhydrous potassium carbonate (2.5 g, 18 mmol) and acetonitrile (50 L). To the resulting mixture was slowly added a solution of diphenylbromomethane (1.78 g, 7.2 mmol) in acetonitrile dropwisely at 85° C. The reaction was conducted for 12 hours. After the completion of reaction monitored by TLC, the resulting mixture was evaporated under reduced pressure to remove acetonitrile. To the residue was added a mixed solution of dichloromethane and water for extraction. The organic phase was dried over anhydrous sodium sulfate and evaporated to remove the solvent to produce a crude product. The crude product was purified by column chromatography (silica gel column, eluted with petroleum ether:ethyl acetate=30:1 (volumetric ratio)) to produce 1-(diphenylmethyl)-3-methylpyrrolidin-3-ol (1 g) in a yield of 52.0%.

(5) Preparation of (4S)-3-[1-diphenylmethyl-3-methylpyrrolidin-3-yl]5-methyl 2,6-dimethyl-4-(3-nitrophenyl)-1,4-dihydropyridine-3,5-dicarboxylate

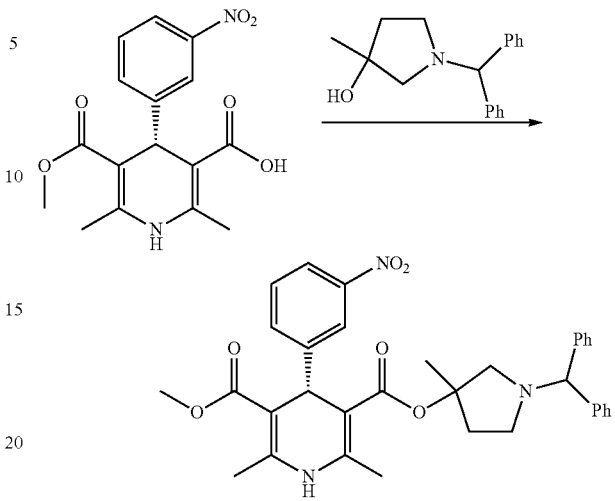

To a solution of (R)-5-methoxycarbonyl-2,6-dimethyl-4-(3-nitrophenyl)-1,4-dihydropyridine-3-carboxylic acid (3.58 g, 10.8 mmol) in dichloromethane was added 1 mL DMF. To the mixture was slowly added oxalyl chloride (2.74 g, 21.6 mmol) dropwisely in an ice bath. The reaction was conducted at 25° C. until the completion of reaction. The resulting mixture was evaporated under reduced pressure to remove oxalyl chloride. To the reaction flask were slowly added 1-(3,3-diphenylpropyl)-3-methylpyrrolidin-3-ol (1 g, 3.7 mmol) and DIPEA (1.4 g, 10.8 mmol) dropwisely under cooling in an ice bath respectively and successively. The reaction was conducted at 25° C. After the completion of reaction monitored by HPLC, the reaction solution was washed with water thrice. The organic phase was dried over anhydrous sodium sulfate, and filtered by suction. The filtrate was evaporated to dryness, and purified by column chromatography (silica gel column, eluted with petroleum ether:ethyl acetate=15:1 (volumetric ratio)) to produce (4S)-3-[1-diphenylmethyl-3-methylpyrrolidin-3-yl]5-methyl 2,6-dimethyl-4-(3-nitrophenyl)-1,4-dihydropyridine-3,5-dicarboxylate (1.2 g) in a yield of 56%.

Molecular formula: C₃₄H₃₅N₃O₆ Mw: 581.2

¹H-NMR (DMSO, 400 MHz) δ: 9.19-9.13 (1H, m), 8.01-7.89 (2H, m), 7.73-7.68 (4H, m), 7.58-7.53 (2H, m), 7.41-7.34 (6H, m), 4.93-4.89 (1H, s), 3.77-3.69 (2H, m), 3.62-3.42 (3H, m), 3.37-3.22 (3H, m), 2.49-2.48 (1H, s), 2.28-1.99 (6H, d), 1.50-1.35 (3H, dd).

Example 24

Preparation of (4S)-3-[1-(3,3-bis(4-fluorophenyl)propyl)-3-methylpyrrolidin-3-yl]5-methyl 2,6-dimethyl-4-(3-nitrophenyl)-1,4-dihydropyridine-3,5-dicarboxylate (Compound 27)

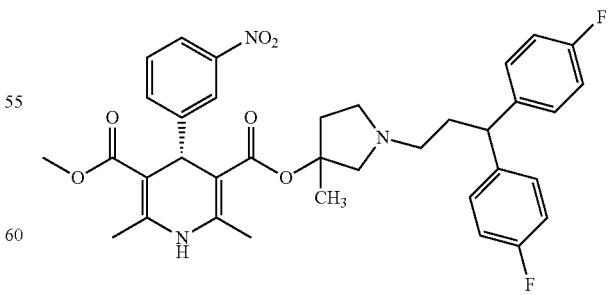

The steps in Example 15 were repeated, except that the reactant in step (4) ethyl 3,3-diphenyl-1-propanate was replaced with ethyl 3,3-bis(4-fluoro)phenyl-1-propanate to obtain Compound 27.

MS (M+H): 646.3.

With reference to the above processes, the following compounds can also be prepared:

| No. | Structure |
|---|---|
| 24 | 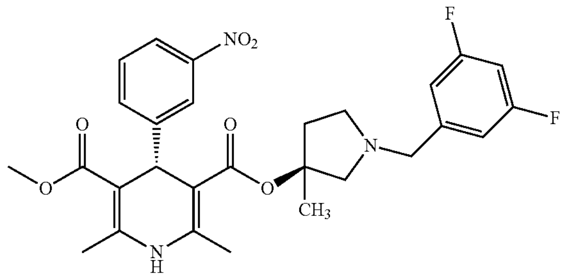 [SMILES: COC(=O)C1=C(C)NC(C)=C(C(=O)O[C@@]2(C)CCN(Cc3cc(F)cc(F)c3)C2)[C@H]1c1cccc([N+](=O)[O-])c1] |
| 25 | 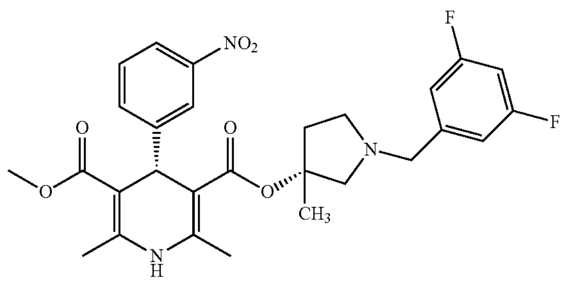 |
| 28 | 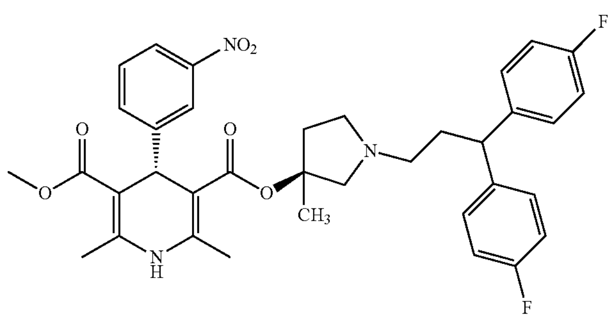 [SMILES: COC(=O)C1=C(C)NC(C)=C(C(=O)O[C@@]2(C)CCN(CCC(c3ccc(F)cc3)c3ccc(F)cc3)C2)[C@H]1c1cccc([N+](=O)[O-])c1] |
| 29 | 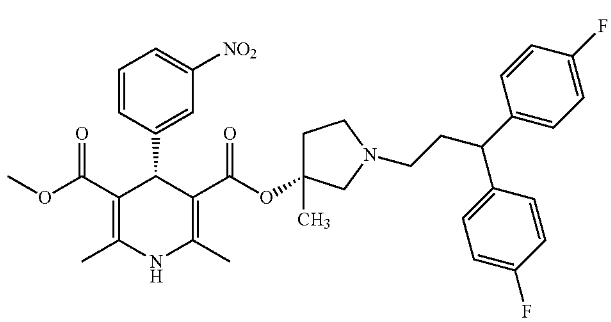 [SMILES: COC(=O)C1=C(C)NC(C)=C(C(=O)O[C@]2(C)CCN(CCC(c3ccc(F)cc3)c3ccc(F)cc3)C2)[C@H]1c1cccc([N+](=O)[O-])c1] |
| 30 | 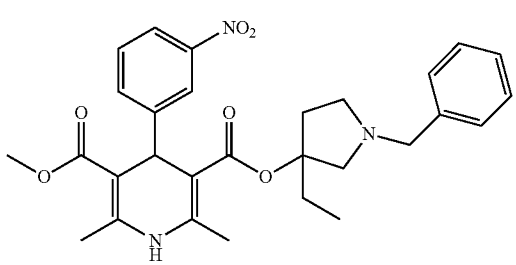 [SMILES: CCC1(OC(=O)C2=C(C)NC(C)=C(C(=O)OC)C2c2cccc([N+](=O)[O-])c2)CCN(Cc2ccccc2)C1] |

-continued
| No. | Structure |
|---|---|
| 31 | 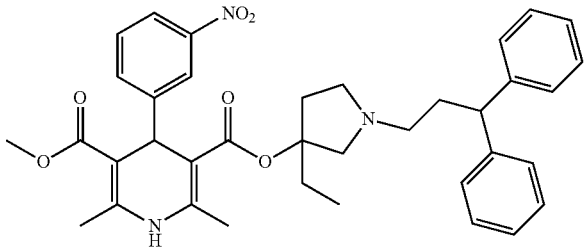 |
| 32 | 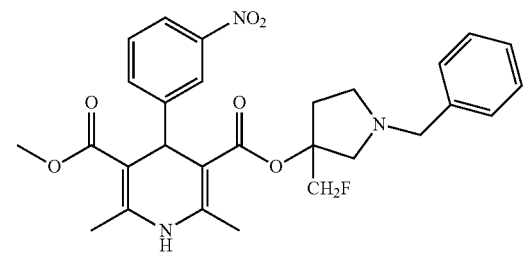 |
| 33 | 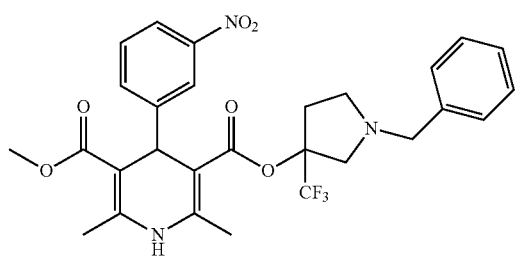 |
| 34 | 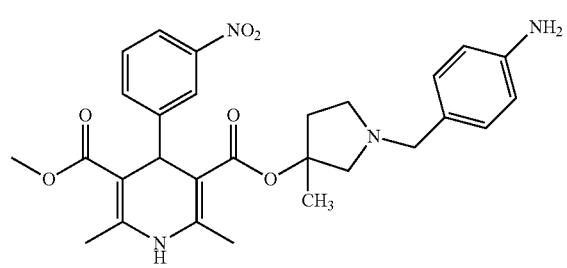 [SMILES: COC(=O)C1=C(C)NC(C)=C(C(=O)OC2(C)CCN(Cc3ccc(N)cc3)C2)C1c1cccc([N+](=O)[O-])c1] |
| 35 | 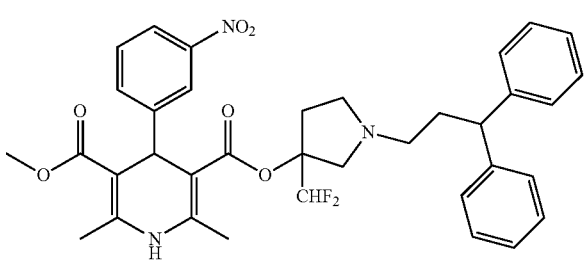 |
| 36 | 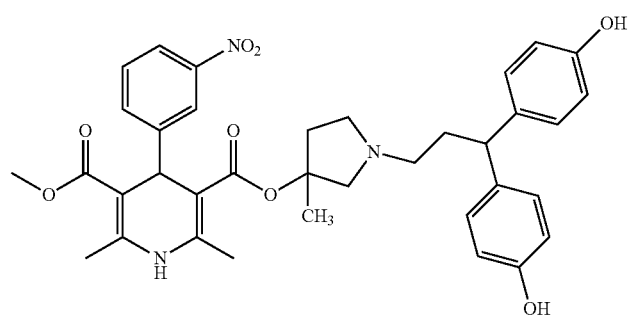 [SMILES: COC(=O)C1=C(C)NC(C)=C(C(=O)OC2(C)CCN(CCC(c3ccc(O)cc3)c3ccc(O)cc3)C2)C1c1cccc([N+](=O)[O-])c1] |

-continued
| No. | Structure |
|---|---|
| 37 | 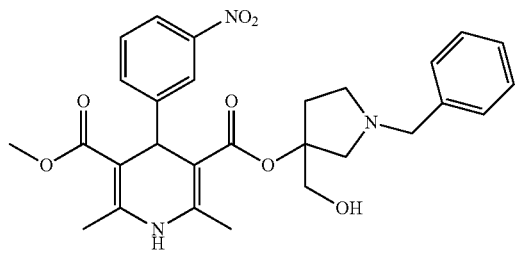 [SMILES: COC(=O)C1=C(C)NC(C)=C(C(=O)OC2(CO)CCN(Cc3ccccc3)C2)C1c1cccc([N+](=O)[O-])c1] |
| 38 | 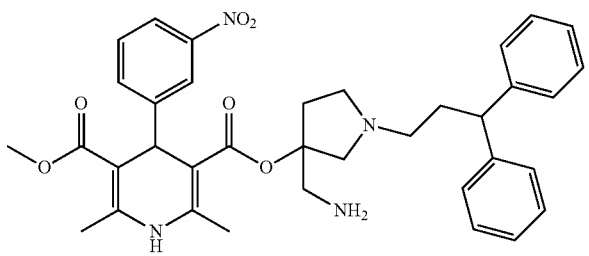 |
| 39 | 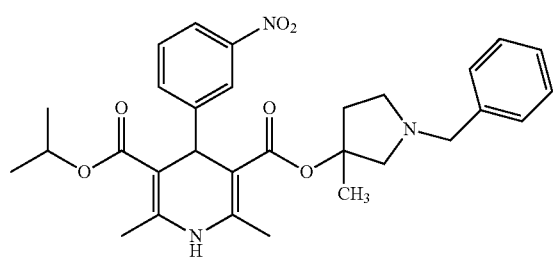 [SMILES: CC1=C(C(=O)OC(C)C)C(c2cccc([N+](=O)[O-])c2)C(C(=O)OC2(C)CCN(Cc3ccccc3)C2)=C(C)N1] |
| 40 | 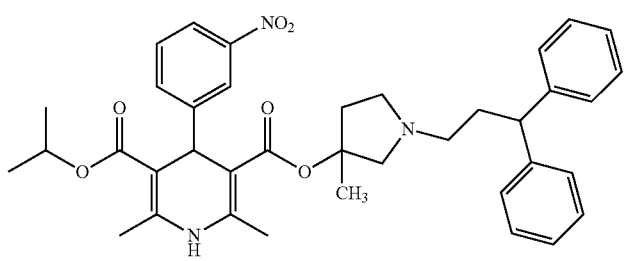 [SMILES: CC1=C(C(=O)OC(C)C)C(c2cccc([N+](=O)[O-])c2)C(C(=O)OC2(C)CCN(CCC(c3ccccc3)c3ccccc3)C2)=C(C)N1] |
| 41 | 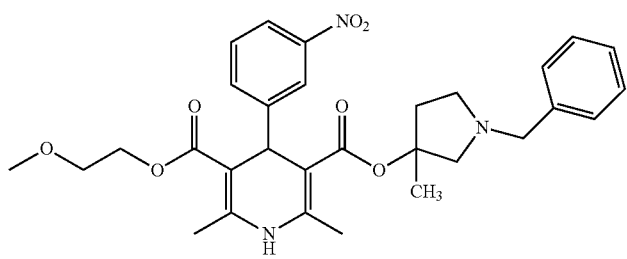 [SMILES: COCCOC(=O)C1=C(C)NC(C)=C(C(=O)OC2(C)CCN(Cc3ccccc3)C2)C1c1cccc([N+](=O)[O-])c1] |
| 42 | 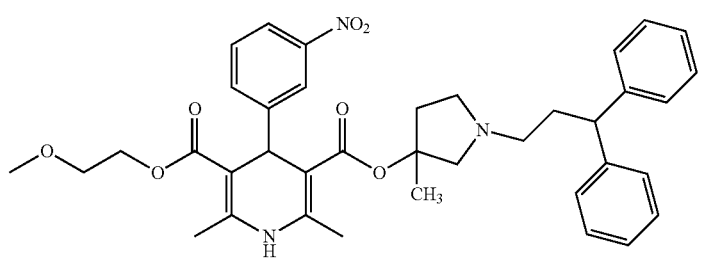 [SMILES: COCCOC(=O)C1=C(C)NC(C)=C(C(=O)OC2(C)CCN(CCC(c3ccccc3)c3ccccc3)C2)C1c1cccc([N+](=O)[O-])c1] |

-continued
| No. | Structure |
|---|---|
| 43 | 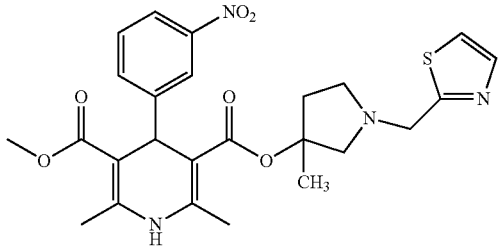 [SMILES: COC(=O)C1=C(C)NC(C)=C(C(=O)OC2(C)CCN(Cc3nccs3)C2)C1c1cccc([N+](=O)[O-])c1] |
| 44 | 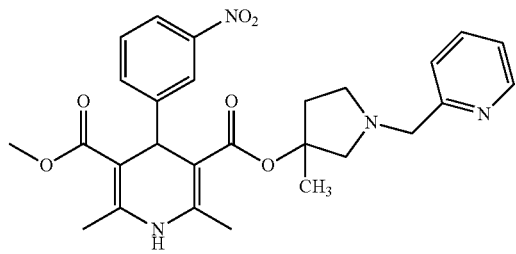 |
| 45 | 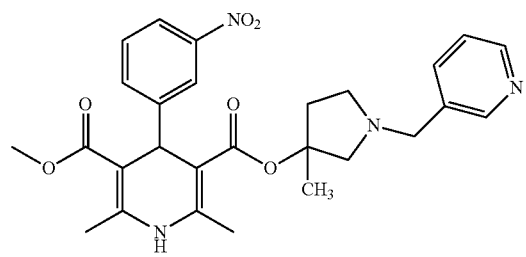 [SMILES: COC(=O)C1=C(C)NC(C)=C(C(=O)OC2(C)CCN(Cc3cccnc3)C2)C1c1cccc([N+](=O)[O-])c1] |
| 46 | 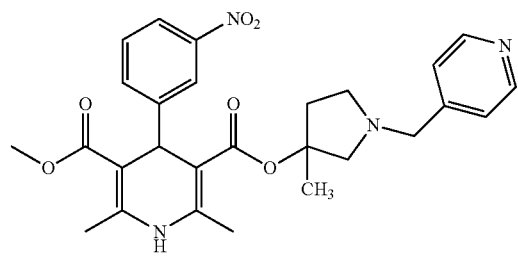 [SMILES: COC(=O)C1=C(C)NC(C)=C(C(=O)OC2(C)CCN(Cc3ccncc3)C2)C1c1cccc([N+](=O)[O-])c1] |
| 47 | 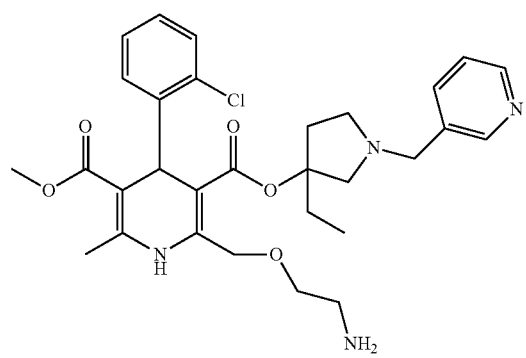 |

-continued
| No. | Structure |
|---|---|
| 48 | 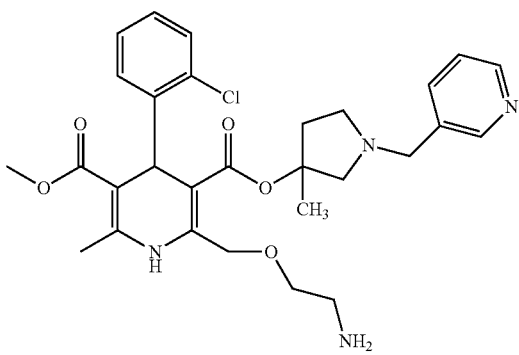 [SMILES: COC(=O)C1=C(C)NC(COCCN)=C(C(=O)OC2(C)CCN(Cc3cccnc3)C2)C1c1ccccc1Cl] |
| 49 | 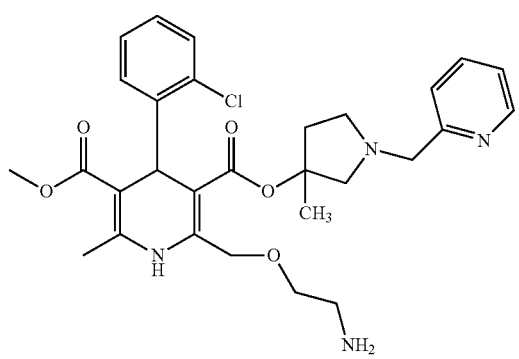 [SMILES: COC(=O)C1=C(C)NC(COCCN)=C(C(=O)OC2(C)CCN(Cc3ccccn3)C2)C1c1ccccc1Cl] |
| 50 | 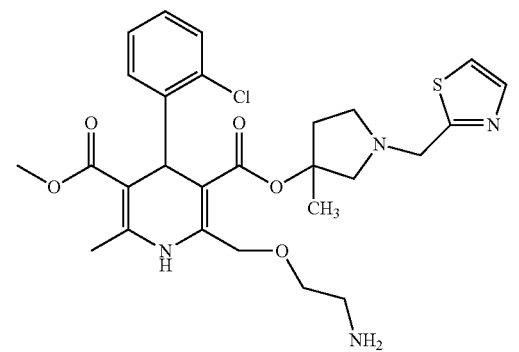 [SMILES: COC(=O)C1=C(C)NC(COCCN)=C(C(=O)OC2(C)CCN(Cc3nccs3)C2)C1c1ccccc1Cl] |
| 51 | 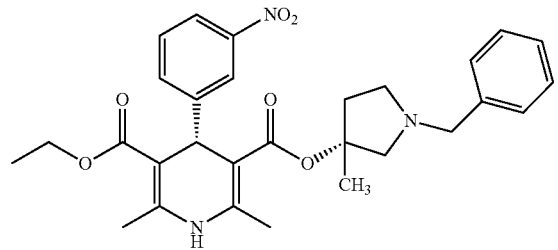 |
| 52 | 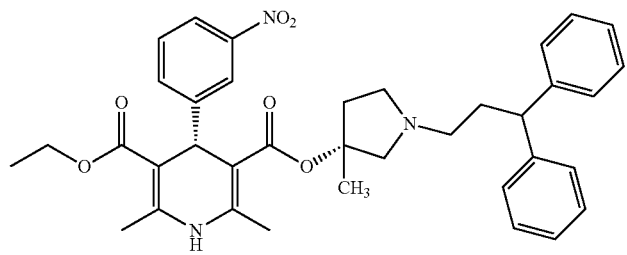 [SMILES: CCOC(=O)C1=C(C)NC(C)=C(C(=O)O[C@]2(C)CCN(CCC(c3ccccc3)c3ccccc3)C2)[C@H]1c1cccc([N+](=O)[O-])c1] |

-continued
| No. | Structure |
|---|---|
| 53 | 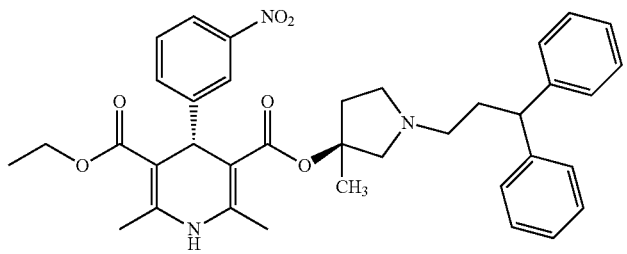 [SMILES: CCOC(=O)C1=C(C)NC(C)=C(C(=O)O[C@@]2(C)CCN(CCC(c3ccccc3)c3ccccc3)C2)[C@H]1c1cccc([N+](=O)[O-])c1] |
| 54 | 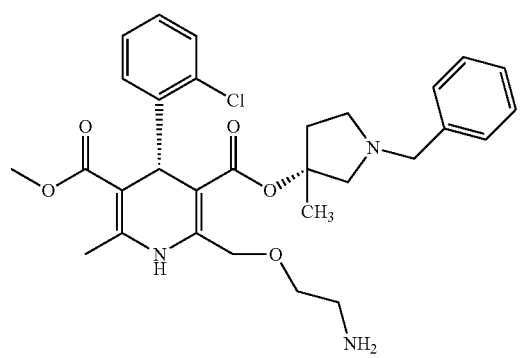 [SMILES: COC(=O)C1=C(C)NC(COCCN)=C(C(=O)O[C@]2(C)CCN(Cc3ccccc3)C2)[C@H]1c1ccccc1Cl] |
| 55 | 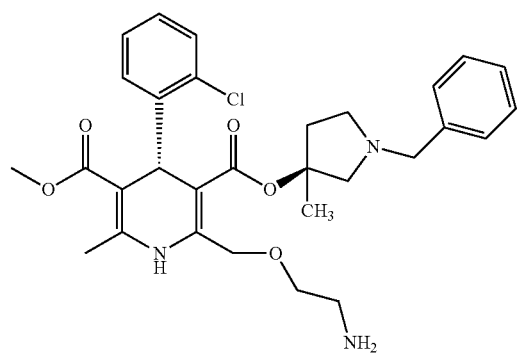 [SMILES: COC(=O)C1=C(C)NC(COCCN)=C(C(=O)O[C@@]2(C)CCN(Cc3ccccc3)C2)[C@H]1c1ccccc1Cl] |
| 56 | 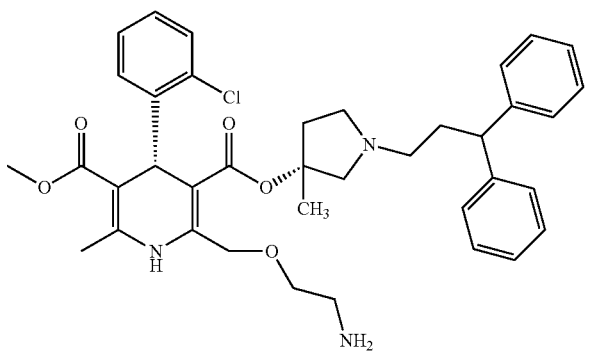 [SMILES: COC(=O)C1=C(C)NC(COCCN)=C(C(=O)O[C@]2(C)CCN(CCC(c3ccccc3)c3ccccc3)C2)[C@H]1c1ccccc1Cl] |

-continued
| No. | Structure |
|---|---|
| 57 | 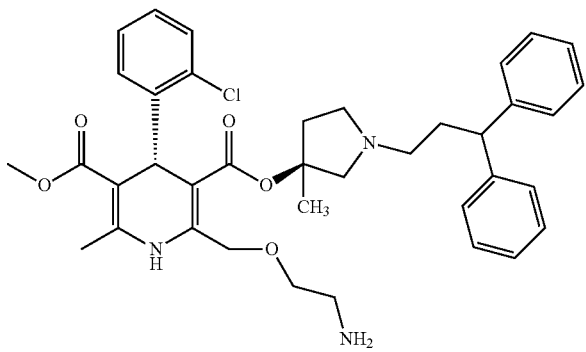 |
| 58 | 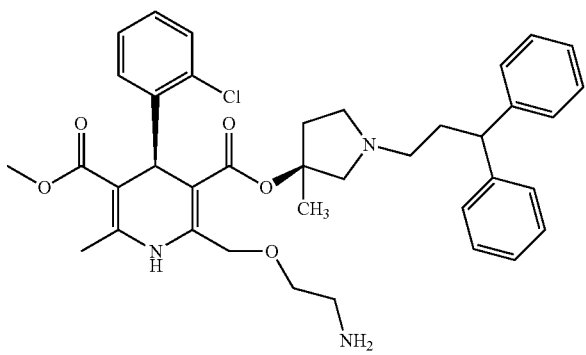 [SMILES: COC(=O)C1=C(C)NC(COCCN)=C(C(=O)O[C@@]2(C)CCN(CCC(c3ccccc3)c3ccccc3)C2)[C@@H]1c1ccccc1Cl] |
| 59 | 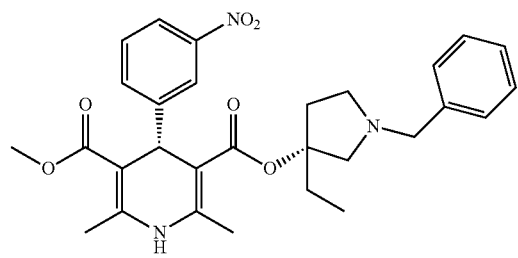 [SMILES: CC[C@@]1(OC(=O)C2=C(C)NC(C)=C(C(=O)OC)[C@@H]2c2cccc([N+](=O)[O-])c2)CCN(Cc2ccccc2)C1] |
| 60 | 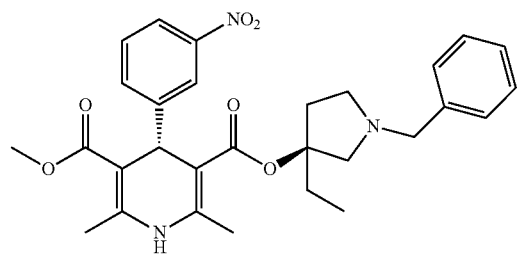 [SMILES: CC[C@]1(OC(=O)C2=C(C)NC(C)=C(C(=O)OC)[C@@H]2c2cccc([N+](=O)[O-])c2)CCN(Cc2ccccc2)C1] |
| 61 | 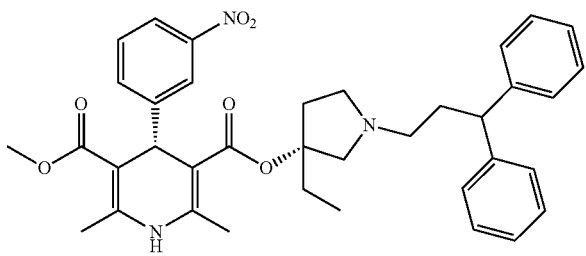 |

-continued

| No. | Structure |
|---|---|
| 62 | 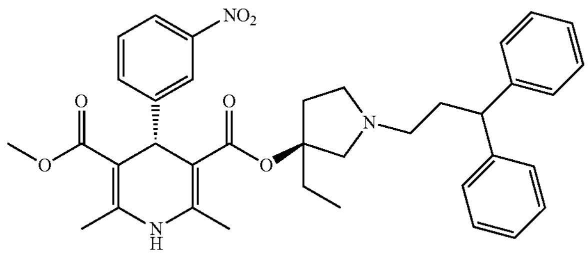 [SMILES: CC[C@]1(OC(=O)C2=C(C)NC(C)=C(C(=O)OC)[C@@H]2c2cccc([N+](=O)[O-])c2)CCN(CCC(c2ccccc2)c2ccccc2)C1] |
| 63 | 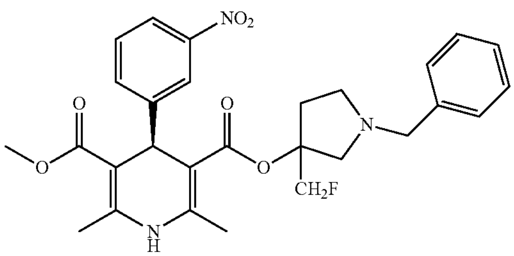 |
| 64 | 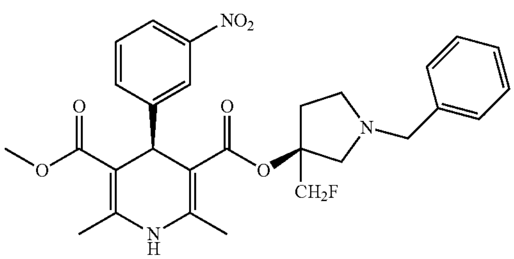 |
| 65 | 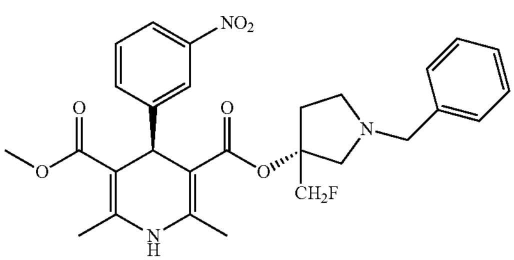 |
| 66 | 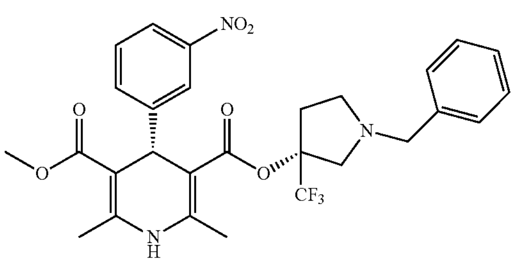 |
| 67 | 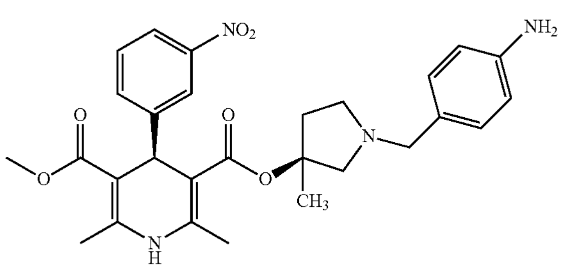 [SMILES: COC(=O)C1=C(C)NC(C)=C(C(=O)O[C@@]2(C)CCN(Cc3ccc(N)cc3)C2)[C@@H]1c1cccc([N+](=O)[O-])c1] |

-continued

| No. | Structure |
|---|---|
| 68 | 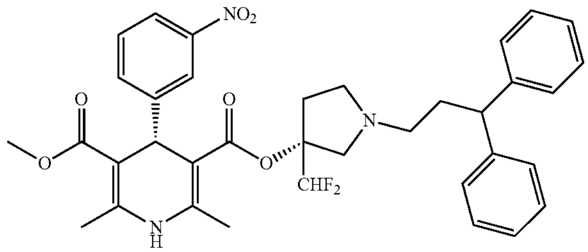 |
| 69 | 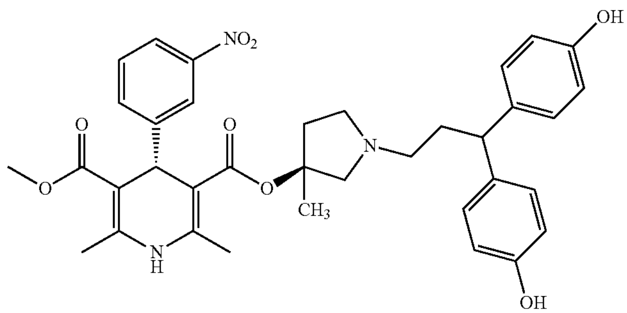 [SMILES: COC(=O)C1=C(C)NC(C)=C(C(=O)O[C@@]2(C)CCN(CCC(c3ccc(O)cc3)c3ccc(O)cc3)C2)[C@H]1c1cccc([N+](=O)[O-])c1] |
| 70 | 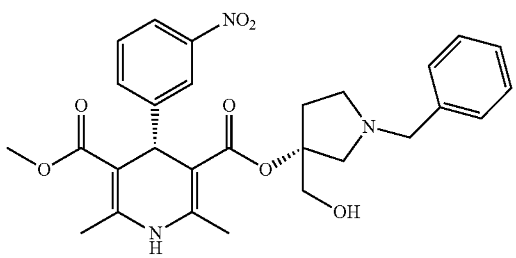 [SMILES: COC(=O)C1=C(C)NC(C)=C(C(=O)O[C@]2(CO)CCN(Cc3ccccc3)C2)[C@H]1c1cccc([N+](=O)[O-])c1] |
| 71 | 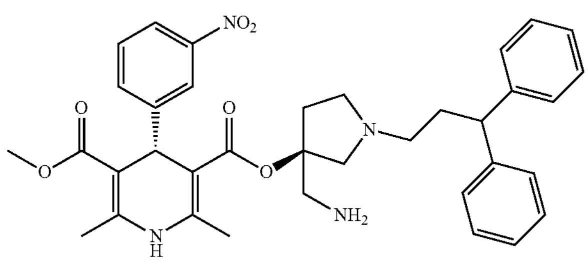 |
| 72 | 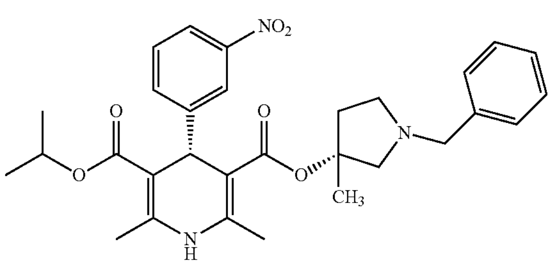 |
| 73 | 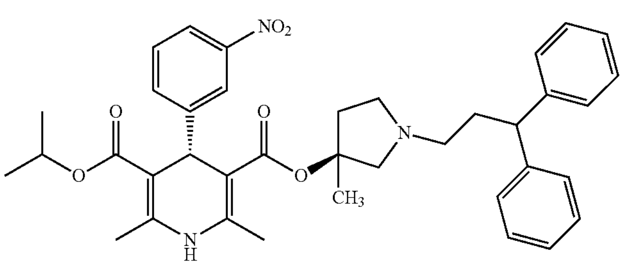 [SMILES: CC1=C(C(=O)OC(C)C)[C@H](c2cccc([N+](=O)[O-])c2)C(C(=O)O[C@@]2(C)CCN(CCC(c3ccccc3)c3ccccc3)C2)=C(C)N1] |

| No. | Structure |
|---|---|
| 74 | 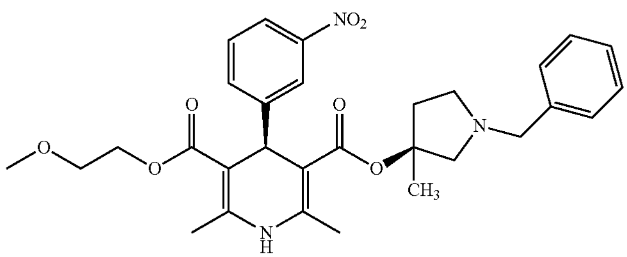 [SMILES: COCCOC(=O)C1=C(C)NC(C)=C(C(=O)O[C@@]2(C)CCN(Cc3ccccc3)C2)[C@@H]1c1cccc([N+](=O)[O-])c1] |
| 75 | 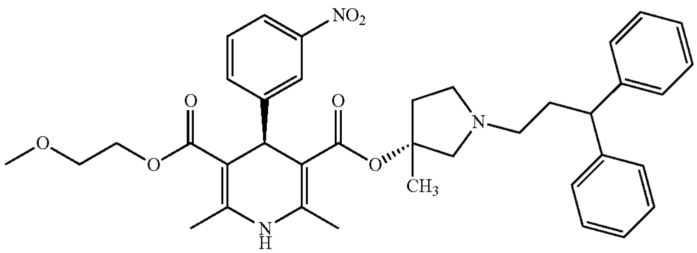 [SMILES: COCCOC(=O)C1=C(C)NC(C)=C(C(=O)O[C@]2(C)CCN(CCC(c3ccccc3)c3ccccc3)C2)[C@@H]1c1cccc([N+](=O)[O-])c1] |
| 76 | 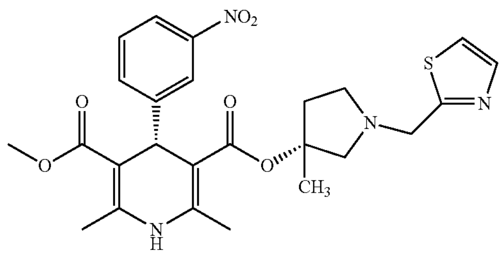 [SMILES: COC(=O)C1=C(C)NC(C)=C(C(=O)O[C@]2(C)CCN(Cc3nccs3)C2)[C@H]1c1cccc([N+](=O)[O-])c1] |
| 77 | 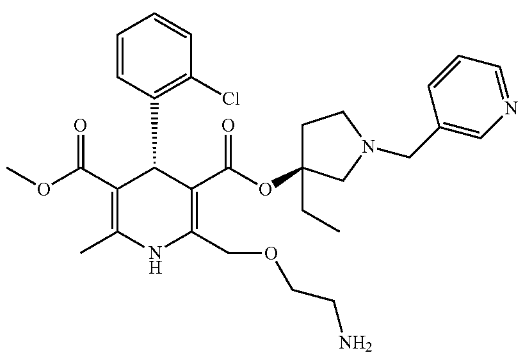 [SMILES: CC[C@]1(OC(=O)C2=C(COCCN)NC(C)=C(C(=O)OC)[C@@H]2c2ccccc2Cl)CCN(Cc2cccnc2)C1] |

II. Pharmacological Activity Assay of the Compound of the Present Invention

The beneficial effects of the compound of the present invention will be further illustrated by the following pharmacological assays. But it should be understood that the beneficial effects of the compound of the present invention are not merely limited thereto.

Assay 1: Determination of the blocking activity of the compound of the present invention on L-type and T-type calcium ion channels 1. Test sample: Compound 1 hydrochloride, Compound 2 hydrochloride, Compound 14, Compound 15, Compound 16, Compound 17, Compound 19 and Compound 20, made in-house, the chemical names and structural formulae thereof are as mentioned above; Positive control: lercanidipine, barnidipine, amlodipine and azelnidipine, commercially purchased.

2. Test for L- and T-Type Calcium Ion Channel Inhibitors

This experiment was assigned to HD Biosciences Corporation (Shanghai) and conducted with an electrophysiological method. The results are shown in Table 1 and Table 2.

Experimental Procedure:

It was done with reference to the method as disclosed by Jung-Ha Lee, et. al., "Identification of T-Type α1H $Ca^{2+}$ Channels ($Ca_v3.2$) in Major Pelvic Ganglion Neurons". *J Neurophysiol* 87:2844-2850, 2002.

Test samples were weighed accurately and diluted in a 3-fold stepwise dilution so that the final concentrations were as follows:

10 μM, 3 μM, 1 μM, 0.3 μM, 0.1 μM, 0.03 μM.

T-type test: Cerebral cortex nerve cells were separated from suckling mice, and used in the experiment after 7 days of cultivation. The ionic current of a single cell was recorded by applying the whole cell patch-clamp technique at room temperature, wherein the clamp current was −90 mV, and the pulse interval was 10 s. The inward current (the activation was started from −20 mV) is the T-type calcium current ($I_{Ca,T}$).

L-type test: Left ventricle muscle cells were separated from guinea pigs. The cells were used in the experiment in eight hours. The ionic current of a single cell was recorded by applying the whole cell patch-clamp technique at room temperature, wherein the clamp current was −80 mV, and the pulse interval was 10 s. The inward current (the activation was started from 0 mV) is the L-type calcium current ($I_{Ca,L}$).

The electrode inner liquid (mM): CsCl 120, TEA-Cl 20, $CaCl_2$ 1, EGTA-CsOH 11, Hepes 10, Mg-ATP 5, pH7.3;

TEA-Cl: 165.70 mg, cesium chloride: 1010.16 mg, calcium chloride: 7.35 mg, magnesium adenosine triphosphate: 126.80 mg, HEPES: 119.15 mg, EGTA: 209.22 mg, $ddH_2O$: 35 mL.

The above components were thoroughly dissolved in deionized water. The pH value was adjusted to 7.25 with 1M cesium hydroxide. A suitable amount of deionized water was added to adjust the final volume to 50 mL; the osmotic pressure was adjusted to 280 mOsm; the solution was filtered with a 0.20 μm filter, split charged into 1 mL EP tubes, and preserved at −20° C. for use.

The electrode outer liquid (mM): NaCl 135, CsCl 5.4, $CaCl_2$ 1.8, $MgCl_2$ 1, Hepes 5, glucose 10, pH7.4.

Sodium chloride: 7890.00 mg, cesium chloride: 909.14 mg, calcium chloride: 264.64 mg, magnesium chloride: 203.30 mg, HEPES: 1191.50 mg, glucose: 1981.70 mg, $ddH_2O$: 980 mL.

The above components were weighed and mixed into 850 mL dd $H_2O$. The mixture was thoroughly dissolved by using a magnetic stirrer. The pH value was adjusted to 7.40 with 1M sodium hydroxide and the final volume was adjusted to 1000 mL. After the osmotic pressure was adjusted to 290 mOsm (milliosmole), the solution was placed in a clean bottle, and preserved in the refrigerator at 4° C. for use.

T-type tests for Compound 19 and Compound 20 were assigned to Chan Test Corporation, and conducted according to the FLIPR experimental procedure as follows.

Experimental Procedure:
It was done with reference to the method disclosed on page 48 of WO 2009/056934 A1.

Samples were weighed accurately and diluted in a 3-fold stepwise dilution so that the final concentrations were as follows: 100 μM, 30 μM, 10 μM, 3 μM, 1 μM, 0.3 μM, 0.1 μM, 0.03 μM, 0.01 μM, 0.003 μM.

T-type test: Human Cav3.2 was cloned in stable HEK-293 cells, and then the operation was conducted with FLIPR Calcium 4 No-Wash kit. The cell medium was removed. To an HEPES solution free of calcium ion was added 20 μL dye to dye for 30 minutes at a temperature of 37° C. This buffer free of calcium ion included NaCl, 137 mM; KCl, 0.5 mM; $MgCl_2$ mM, 1 mM; HEPES, 10 mM; glucose, 10 mM. The pH value was adjusted to 7.4 with NaOH. After 30 minutes, the buffer was placed at room temperature for 30 minutes. Then 5 μL of compound to be tested, solvent or blank control were added. The compound was formulated with a buffer containing calcium ion, said buffer including KCl, 135 mM; $CaCl_2$, 10.8 mM; $MgCl_2$, 1 mM; HEPES, 10 mM; glucose, 10 mM. The collected fluorescence values were analyzed and the inhibition ratios were calculated. The results were shown in Table 3.

3. Experiment Result and Conclusion

TABLE 1

The inhibition activities of the compounds of the present invention on L-type calcium ion channels (electrophysiological method)

| Test sample | $IC_{50}$(μM) L-type |
|---|---|
| lercanidipine | 0.84 |
| barnidipine | 0.58 |
| amlodipine | 1.11 |
| azelnidipine | 1.39 |
| nifedipine | 0.3 |
| Compound 14 | 0.59 |
| Compound 15 | 1.28 |
| Compound 16 | 0.59 |
| Compound 17 | 0.93 |

It could be seen from Table 1 that the compounds of the present invention have strong inhibition activities on L-type calcium ion channels, which were comparable with the inhibition effects of the control samples.

TABLE 2

The inhibition activities of the compounds of the present invention on T-type calcium ion channels

| Test sample | $IC_{50}$(μM) |
|---|---|
| lercanidipine | >10 |
| barnidipine | 8.15 |
| amlodipine | 15.63 |
| azelnidipine | 378.3 |
| nifedipine | 1140 |
| Compound 1 hydrochloride | 4.47 |
| Compound 2 hydrochloride | 3.20 |
| Compound 16 | 2.28 |

TABLE 3

The inhibition activities of the compounds of the present invention on T-type calcium ion channels (FLIPR method)

| Test sample | $IC_{50}$(μM) T-type |
|---|---|
| barnidipine | 30.80 |
| amlodipine | >100 |
| Compound 16 | 1.95 |
| Compound 17 | 9.41 |
| Compound 19 | 75.44 |
| Compound 20 | 66.86 |

It could be seen from Table 2 and Table 3 that the compounds of the present invention have inhibition activities on T-type calcium ion channels that are significantly superior over the inhibition activities of the positive control samples on T-type calcium ion channels, and therefore have a better hypotensive effect, a protective effect on kidney and heart, as well as a lower side effect.

Assay 2: The in vivo hypotensive activity assay of the compounds of the present invention 1. Test sample: Compound 18, Compound 21, Compound 22, Compound 23, Compound 26, Compound 19 and Compound 20, made in-house, the chemical names and structural formulae thereof are as mentioned above;

Positive control: lercanidipine, barnidipine, amlodipine, azelnidipine, efonidipine and manidipine, commercially purchased.

2. Experimental Procedure:
The in vivo hypotensive activity assay was conducted according to the tail-pinch method with reference to Folia pharmacol. Japon. 97, 115-126 (1991).

The agents to be tested, lercanidipine, barnidipine, amlodipine, azelnidipine, efonidipine and manidipine, were accurately weighed respectively. Each agent was dissolved in DMSO. To the resulting solution was added 50% of the corresponding volume of PEG400 so that the final concentration of each agent was 1 mg/ml, and the final concentration of DMSO was 3%.

The compounds to be tested, Compound 18, Compound 21, Compound 22, Compound 23, and Compound 26, were accurately weighed respectively. Each compound was dissolved in DMSO. To the resulting solution was added 50% of the corresponding volume of PEG400 so that the final concentration of each compound was 1 mg/ml, and the final concentration of DMSO was 3%.

The compounds to be tested, Compound 19 and Compound 20, were accurately weighed respectively. Each compound was suspended in 0.5% MC so that the final concentration of each compound was 1 mg/ml.

The test for hypotensive effect: Male SHRs (spontaneous hypertensive rats) were randomly allocated into a control group and an administration group. The administration was an intragastric administration. One hour before the administration, the measured blood pressure was used as the pre-administration basic blood pressure value. After the administration, the contractive pressure, the heart rate and the mean arterial pressure of SHRs at six time points, i.e. 1, 2, 4, 6, 8 and 24 hours after the administration, were measured with a Softron BP-98A non-invasive blood pressure instrument respectively. The test results were shown in Table 4.

3. Experiment Result and Conclusion:

TABLE 4

The hypotensive activities of the compounds of the present invention on SHRs

| Test sample | Administration dosage (mg/kg, po) | Animal number | Max ΔMAP (mmHg ± SEM) | ΔMAP > 20 (mmHg) Duration time of action (h) |
|---|---|---|---|---|
| lercanidipine | 10 | 4 | 77 ± 15 | 23 |
| barnidipine | 10 | 4 | 81 ± 10 | 14 |
| amlodipine | 10 | 4 | 74 ± 8 | 24 |
| azelnidipine | 10 | 4 | 79 ± 13 | 24 |
| efonidipine | 10 | 4 | 69 ± 5 | 10 |
| manidipine | 10 | 4 | 74 ± 5 | 23 |
| Compound 18 | 10 | 4 | 69 ± 4 | 24 |
| Compound 19 | 10 | 3 | 72 ± 8 | 24 |
| Compound 20 | 10 | 4 | 80 ± 14 | 24 |
| Compound 21 | 10 | 3 | 28 ± 12 | 24 |
| Compound 22 | 10 | 3 | 43 ± 7 | 24 |
| Compound 23 | 10 | 3 | 60 ± 12 | 24 |
| Compound 26 | 10 | 4 | 55 ± 13 | 24 |

Note:
ΔMAP is the difference between the average arterial pressure value after the administration and the average arterial pressure value before the administration.

It could be seen from Table 4 that the compounds of the present invention have good hypotensive effect in SHRs, and maintained the hypotensive effect above 20 mmHg for a longer duration time than control samples.

Assay 3: The in vivo hypotensive activity assay of the compounds of the present invention 1. Test sample: Compound 1, Compound 2, Compound 15, Compound 16 and Compound 17, made in-house, the chemical names and structural formulae thereof are as mentioned above;

Positive control: lercanidipine, barnidipine, amlodipine and azelnidipine, commercially purchased.

2. Experimental Procedure:

The in vivo hypotensive activity assay was conducted according to DSI experimental procedure with reference to page 56 of WO 2009/056934 A1.

The agents to be tested, lercanidipine, barnidipine, amlodipine, azelnidipine, efonidipine and manidipine, were accurately weighed. Each agent was dissolved in DMSO. To the resulting solution was added 50% of the corresponding volume of PEG400 so that the final concentration of each agent was 1 mg/ml, and the final concentration of DMSO was 3%.

The compounds to be tested, Compound 1 and Compound 2, were accurately weighed. Each compound was dissolved in DMSO. To the resulting solution was added 50% of the corresponding volume of PEG400 so that the final concentration of each compound was 1 mg/ml, and the final concentration of DMSO was 2%.

The compound to be tested, Compound 15, was accurately weighed. This compound was dissolved in DMSO. To the resulting solution was added 50% of the corresponding volume of PEG400 so that the final concentration of this compound was 1 mg/ml, and the final concentration of DMSO was 3%.

The compound to be tested, Compound 16 (optical activity)+108.34° and Compound 17 (optical activity optical activity)+36.4°, were accurately weighed. Each compound was suspended in 0.5% MC so that the final concentration of each compound was 1 mg/ml.

The test for hypotensive effect: Male SHRs were subjected to an abdominal aorta implantation using an implant, and used in the test after 7-10 days of recovery. The administration was an intragastric administration. One hour before the administration, the measured blood pressure was used as the pre-administration basic blood pressure value. After the administration, SHRs, allowed free access to the diet, were continuously monitored with a DSI implant-type blood pressure remote measurement system for 24 hours. The test results were shown in Table 5.

3. Experiment Result and Conclusion:

TABLE 5

The hypotensive activities of the compounds of the present invention on SHRs

| Test sample | Administration dosage (mg/kg, po) | Animal number | Max ΔMAP (mmHg ± SEM) | ΔMAP > 20 (mmHg) Duration time of action (h) |
|---|---|---|---|---|
| lercanidipine | 10 | 4 | 54 ± 7 | 14 |
| barnidipine | 10 | 4 | 60 ± 6 | 9 |
| amlodipine | 10 | 4 | 48 ± 13 | 16 |
| azelnidipine | 10 | 4 | 40 ± 5 | 11 |
| Compound 1 | 10 | 3 | 47 ± 7 | 6 |
| Compound 2 | 10 | 3 | 53 ± 7 | 16 |
| Compound 15 | 10 | 3 | 56 ± 1 | 14 |
| Compound 16 | 10 | 4 | 57 ± 5 | 11 |
| Compound 17 | 10 | 4 | 57 ± 5 | 16 |

Note:
ΔMAP is the difference between the average arterial pressure value after the administration and the average arterial pressure value before the administration.

It could be seen from Table 5 that the compounds of the present invention have good hypotensive effect in SHRs, and maintained the hypotensive effect above 20 mmHg for a longer duration time than control samples.

What is claimed is:

1. A compound of general formula (I), a pharmaceutically acceptable salt or a stereoisomer thereof:

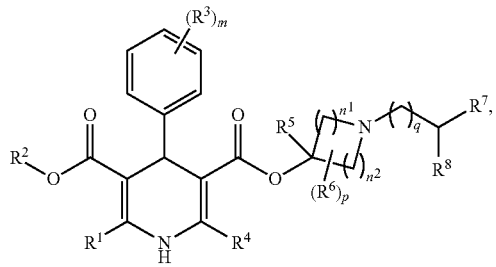

wherein:
- $R^1$ and $R^4$ are each independently selected from methyl, ethyl and ethoxymethyl that are unsubstituted or substituted by 1-3 $Q^1$ substituents, and the carbon atom(s) therein can be optionally replaced with 1-3 groups from O, $N(H)_x$ or $C(O)$, wherein x is selected from 1 or 2; $Q^1$ is selected from halogen, hydroxy, amino, methoxy and ethoxy;
- $R^2$ is selected from methyl, ethyl, isopropyl, cyclopropyl, cyclopropylmethyl, azetidinyl, pyrrolidinyl, piperidyl, morpholinyl, pyrrolidinylmethyl and morpholinylmethyl that are unsubstituted or substituted by 1-3 $Q^2$ substituents, $Q^2$ is selected from fluoro, chloro, hydroxy, amino, $C_{1-4}$alkyl, $C_{1-4}$alkoxy, and $C_{1-4}$alkyl and $C_{1-4}$alkoxy that are substituted by 1-3 fluoro and/or chloro atoms;
- $R^3$ is selected from hydrogen, fluoro, chloro and nitro;
- $R^5$ and $R^6$ are each independently selected from methyl or ethyl that is unsubstituted or substituted by 1-3 $Q^3$ substituents, $Q^3$ is selected from fluoro, chloro, hydroxy, amino, methoxy and ethoxy;
- $R^7$ and $R^8$ are each independently selected from hydrogen, methyl, ethyl, and phenyl$C_{0-2}$alkyl, pyridyl$C_{0-2}$alkyl, furyl$C_{0-2}$alkyl, thienyl$C_{0-2}$alkyl, pyrrolyl$C_{0-2}$alkyl, thiazolyl$C_{0-2}$alkyl and thiadiazolyl$C_{0-2}$alkyl that are unsubstituted or substituted by 1-3 $Q^4$ substituents, and $R^7$ and $R^8$ are not both hydrogen at the same time, $Q^4$ is selected from fluoro, chloro, hydroxy, amino, methyl, ethyl, fluoromethyl, difluoromethyl, trifluoromethyl, methoxy and ethoxy;
- m is selected from 1, 2 or 3, when m is 2 or 3, $R^3$ can be identical or different;
- $n^1$ is 2, $n^2$ is 1;
- p and q are each independently selected from 0, 1, 2 or 3, wherein when q is 0, neither $R^7$ nor $R^8$ is phenyl$C_{0-2}$alkyl.

2. The compound of claim 1, a pharmaceutically acceptable salt or a stereoisomer thereof:
wherein, $R^1$ and $R^4$ are each independently selected from methyl, ethyl or ethoxymethyl that are unsubstituted or substituted by 1-3 $Q^1$ substituents, wherein $Q^1$ is selected from fluoro, chloro, amino, methoxy or ethoxy;
$R^2$ is selected from methyl or ethyl that is unsubstituted or substituted by 1-3 $Q^2$ substituents, $Q^2$ is selected from fluoro, chloro, methyl, methoxy, or methoxy and ethoxy that are substituted by 1-3 fluoro, chloro atoms;
$R^3$ is selected from hydrogen, chloro or nitro;
$R^5$ is selected from methyl or ethyl that is unsubstituted or substituted by 1-3 $Q^3$ substituents, $Q^3$ is selected from fluoro, chloro, hydroxy or amino;
$R^6$ is selected from methyl that is unsubstituted or substituted by 1-3 $Q^3$ substituents, $Q^3$ is selected from fluoro, chloro, hydroxy or amino;
$R^7$ and $R^8$ are each independently selected from hydrogen, and phenyl, benzyl, pyridyl, furyl, thienyl, thiazolyl or pyrrolyl that is unsubstituted or substituted by 1-3 $Q^4$ substituents, and $R^7$ and $R^8$ are not both hydrogen at the same time,
$Q^4$ is selected from fluoro, chloro, hydroxy, amino, methyl, trifluoromethyl or methoxy;
m is 1;
$n^1$ is 2, $n^2$ is 1;
p and q are each independently selected from 0, 1 or 2, wherein when q is 0, neither $R^7$ nor $R^8$ is phenyl or benzyl.

3. The compound of claim 1, a pharmaceutically acceptable salt or a stereoisomer thereof, wherein said compound is selected from:

| Compound | Structure | Chemical Name |
|---|---|---|
| 2 | 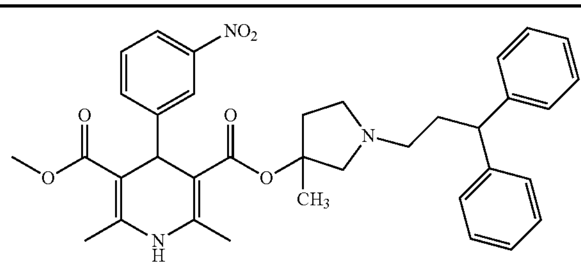 | 3-[1-(3,3-diphenylpropyl)-3-methylpyrrolidin-3-yl] 5-methyl 2,6-dimethyl-4-(3-nitrophenyl)-1,4-dihydropyridine-3,5-dicarboxylate |
| 4 | 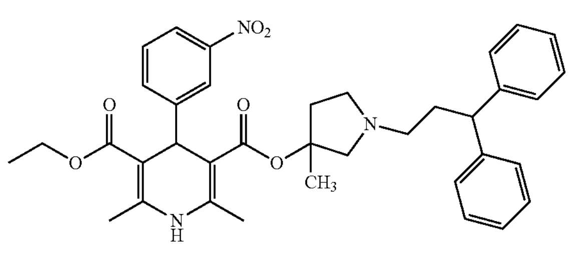 [SMILES: CCOC(=O)C1=C(C)NC(C)=C(C(=O)OC2(C)CCN(CCC(c3ccccc3)c3ccccc3)C2)C1c1cccc([N+](=O)[O-])c1] | 3-[1-(3,3-diphenylpropyl)-3-methylpyrrolidin-3-yl] 5-ethyl 2,6-dimethyl-4-(3-nitrophenyl)-1,4-dihydropyridine-3,5-dicarboxylate |

-continued

| Compound | Structure | Chemical Name |
|---|---|---|
| 6 | 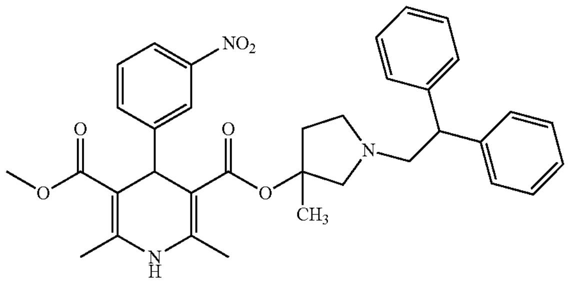 | 3-[1-(2,2-diphenylethyl)-3-methylpyrrolidin-3-yl] 5-methyl 2,6-dimethyl-4-(3-nitrophenyl)-1,4-dihydropyridine-3,5-dicarboxylate |
| 8 | 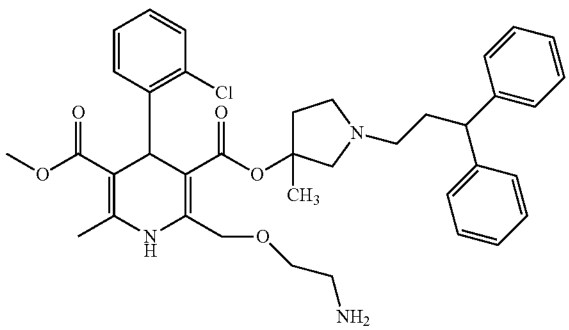 [SMILES: COC(=O)C1=C(C)NC(COCCN)=C(C(=O)OC2(C)CCN(CCC(c3ccccc3)c3ccccc3)C2)C1c1ccccc1Cl] | 3-[1-(3,3-diphenylpropyl)-3-methylpyrrolidin-3-yl] 5-methyl 2-[(2-aminoethoxy)methyl]-4-(2-chlorophenyl)-6-methyl-1,4-dihydropyridine-3,5-dicarboxylate |
| 11 | 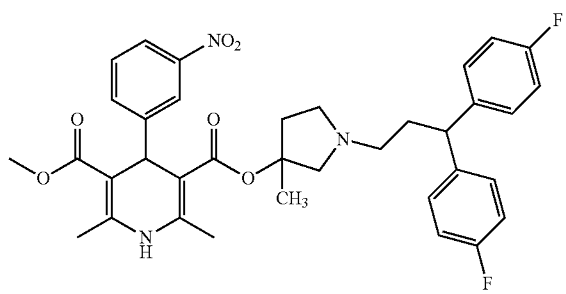 | 3-[1-(3,3-bis(4-fluorophenyl)propyl)-3-methylpyrrolidin-3-yl] 5-methyl 2,6-dimethyl-4-(3-nitrophenyl)-1,4-dihydropyridine-3,5-dicarboxylate |
| 14 | 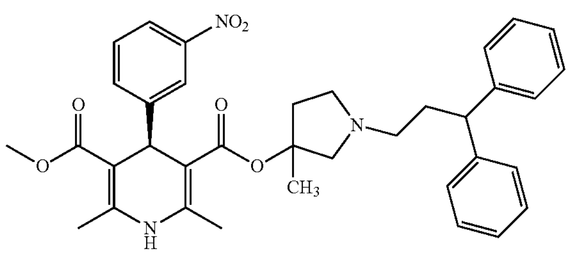 | (4R)-3-[1-(3,3-diphenylpropyl)-3-methylpyrrolidin-3-yl] 5-methyl 2,6-dimethyl-4-(3-nitrophenyl)-1,4-dihydropyridine-3,5-dicarboxylate |
| 15 | 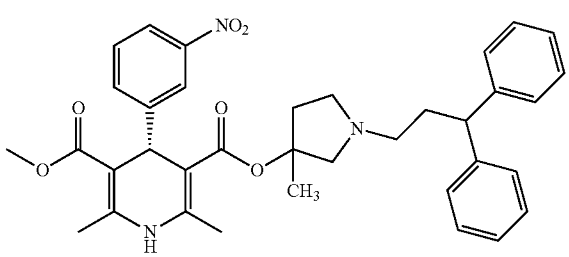 | (4S)-3-[1-(3,3-diphenylpropyl)-3-methylpyrrolidin-3-yl] 5-methyl 2,6-dimethyl-4-(3-nitrophenyl)-1,4-dihydropyridine-3,5-dicarboxylate |

-continued

| Compound | Structure | Chemical Name |
| --- | --- | --- |
| 16 | 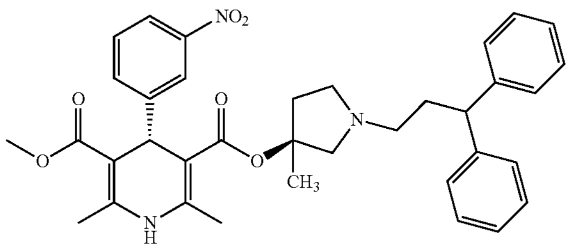 [SMILES: COC(=O)C1=C(C)NC(C)=C(C(=O)O[C@@]2(C)CCN(CCC(c3ccccc3)c3ccccc3)C2)[C@H]1c1cccc([N+](=O)[O-])c1] | (S)-3-[(S)-1-(3,3-diphenylpropyl)-3-methylpyrrolidin-3-yl] 5-methyl 2,6-dimethyl-4-(3-nitrophenyl)-1,4-dihydropyridine-3,5-dicarboxylate |
| 17 | 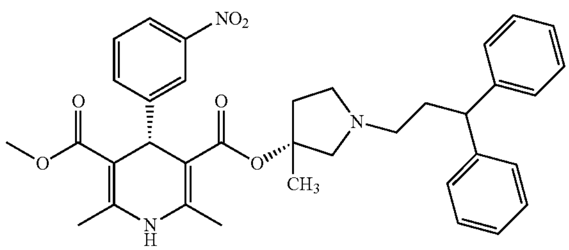 [SMILES: COC(=O)C1=C(C)NC(C)=C(C(=O)O[C@]2(C)CCN(CCC(c3ccccc3)c3ccccc3)C2)[C@H]1c1cccc([N+](=O)[O-])c1] | (S)-3-[(R)-1-(3,3-diphenylpropyl)-3-methylpyrrolidin-3-yl] 5-methyl 2,6-dimethyl-4-(3-nitrophenyl)-1,4-dihydropyridine-3,5-dicarboxylate |
| 18 | 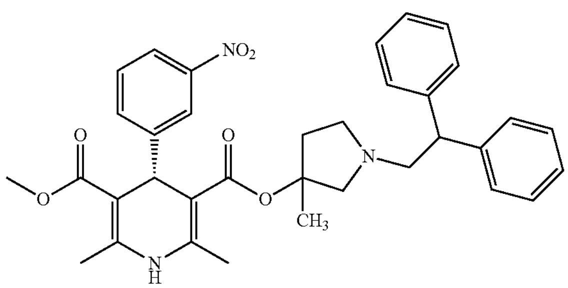 | (4S)-3-[1-(2,2-diphenylethyl)-3-methylpyrrolidin-3-yl] 5-methyl 2,6-dimethyl-4-(3-nitrophenyl)-1,4-dihydropyridine-3,5-dicarboxylate |
| 19 | 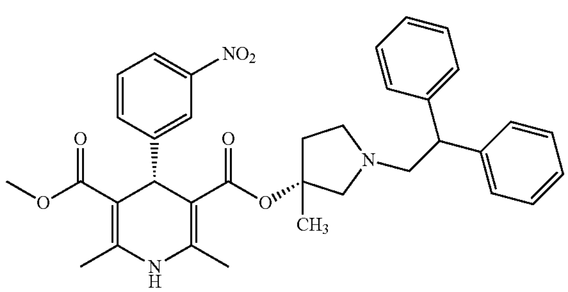 | (S)-3-[(R)-1-(2,2-diphenylethyl)-3-methylpyrrolidin-3-yl] 5-methyl 2,6-dimethyl-4-(3-nitrophenyl)-1,4-dihydropyridine-3,5-dicarboxylate |
| 20 | 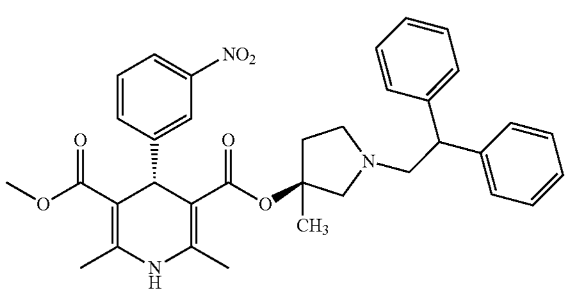 [SMILES: COC(=O)C1=C(C)NC(C)=C(C(=O)O[C@@]2(C)CCN(CC(c3ccccc3)c3ccccc3)C2)[C@H]1c1cccc([N+](=O)[O-])c1] | (S)-3-[(S)-1-(2,2-diphenylethyl)-3-methylpyrrolidin-3-yl] 5-methyl 2,6-dimethyl-4-(3-nitrophenyl)-1,4-dihydropyridine-3,5-dicarboxylate |

| Compound | Structure | Chemical Name |
| --- | --- | --- |
| 27 | 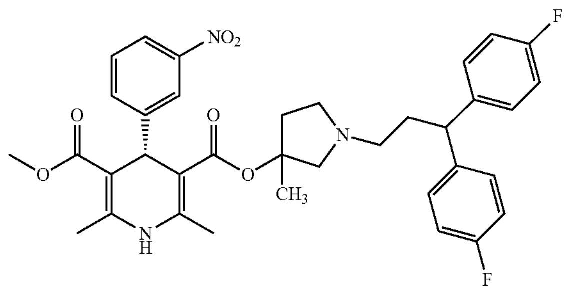 | (4S)-3-[1-(3,3-bis(4-fluorophenyl)propyl)-3-methylpyrrolidin-3-yl] 5-methyl 2,6-dimethyl-4-(3-nitrophenyl)-1,4-dihydropyridine-3,5-dicarboxylate |
| 28 | 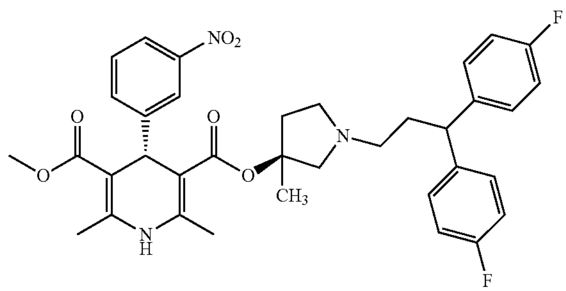 [SMILES: COC(=O)C1=C(C)NC(C)=C(C(=O)O[C@@]2(C)CCN(CCC(c3ccc(F)cc3)c3ccc(F)cc3)C2)[C@H]1c1cccc([N+](=O)[O-])c1] | (S)-3-[(S)-1-(3,3-bis(4-fluorophenyl)propyl)-3-methylpyrrolidin-3-yl] 5-methyl 2,6-dimethyl-4-(3-nitrophenyl)-1,4-dihydropyridine-3,5-dicarboxylate |
| 29 | 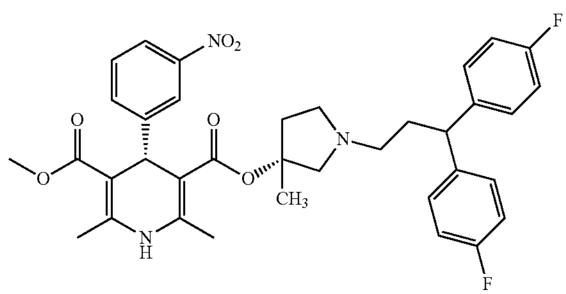 | (S)-3-[(R)-1-(3,3-bis(4-fluorophenyl)propyl)-3-methylpyrrolidin-3-yl] 5-methyl 2,6-dimethyl-4-(3-nitrophenyl)-1,4-dihydropyridine-3,5-dicarboxylate |
| 31 | 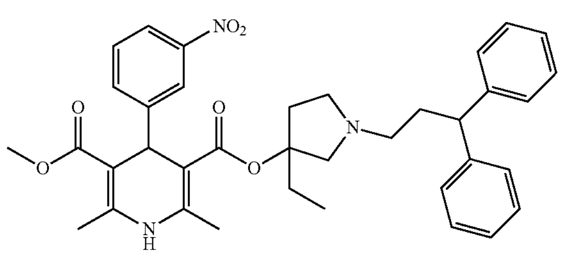 | 3-[1-(3,3-diphenylpropyl)-3-ethylpyrrolidin-3-yl] 5-methyl 2,6-dimethyl-4-(3-nitrophenyl)-1,4-dihydropyridine-3,5-dicarboxylate |
| 35 | 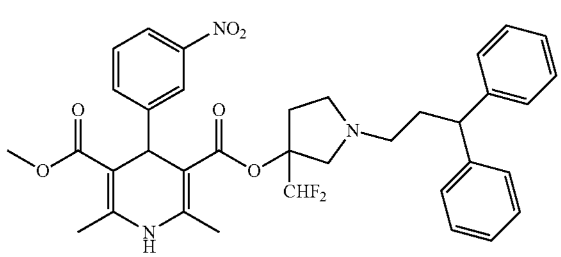 | 3-[3-difluoromethyl-1-(3,3-diphenylpropyl)pyrrolidin-3-yl] 5-methyl 2,6-dimethyl-4-(3-nitrophenyl)-1,4-dihydropyridine-3,5-dicarboxylate |

| Compound | Structure | Chemical Name |
|---|---|---|
| 36 | 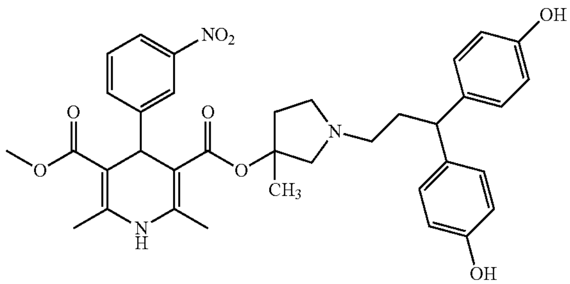 [SMILES: COC(=O)C1=C(C)NC(C)=C(C(=O)OC2(C)CCN(CCC(c3ccc(O)cc3)c3ccc(O)cc3)C2)C1c1cccc([N+](=O)[O-])c1] | 3-[1-(3,3-bis(4-hydroxyphenyl) propyl-3-methylpyrrolidin-3-yl] 5-methyl 2,6-dimethyl-4-(3-nitrophenyl)-1,4-dihydropyridine-3,5-dicarboxylate |
| 38 | 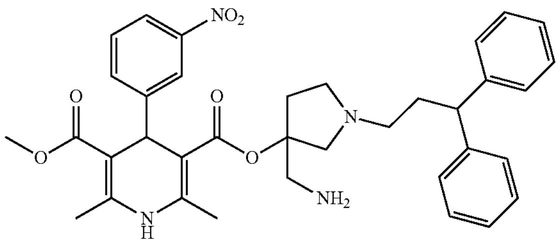 [SMILES: COC(=O)C1=C(C)NC(C)=C(C(=O)OC2(CN)CCN(CCC(c3ccccc3)c3ccccc3)C2)C1c1cccc([N+](=O)[O-])c1] | 3-[3-aminomethyl-1-(3,3-diphenylpropyl) pyrrolidin-3-yl) 5-methyl 2,6-dimethyl-4-(3-nitrophenyl)-1,4-dihydropyridine-3,5-dicarboxylate |
| 40 | 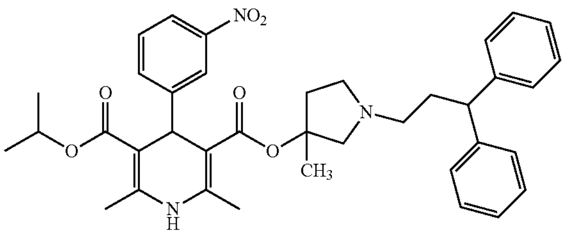 [SMILES: CC1=C(C(=O)OC(C)C)C(c2cccc([N+](=O)[O-])c2)C(C(=O)OC2(C)CCN(CCC(c3ccccc3)c3ccccc3)C2)=C(C)N1] | 3-[1-(3,3-diphenylpropyl)-3-methyl-pyrrolidin-3-yl] 5-isopropyl 2,6-dimethyl-4-(3-nitrophenyl)-1,4-dihydropyridine-3,5-dicarboxylate |
| 42 | 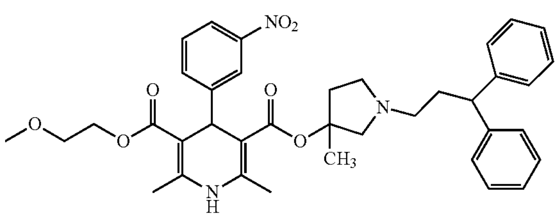 [SMILES: COCCOC(=O)C1=C(C)NC(C)=C(C(=O)OC2(C)CCN(CCC(c3ccccc3)c3ccccc3)C2)C1c1cccc([N+](=O)[O-])c1] | 3-[1-(3,3-diphenylpropyl)-3-methyl-pyrrolidin-3-yl] 5-(2-methoxyethyl) 2,6-dimethyl-4-(3-nitrophenyl)-1,4-dihydropyridine-3,5-dicarboxylate |
| 43 | 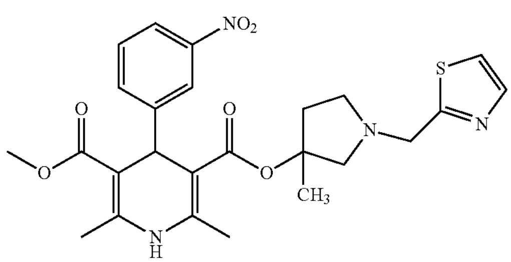 [SMILES: COC(=O)C1=C(C)NC(C)=C(C(=O)OC2(C)CCN(Cc3nccs3)C2)C1c1cccc([N+](=O)[O-])c1] | 3-[3-methyl-1-(thiazol-2-ylmethyl) pyrrolidin-3-yl] 5-methyl 2,6-dimethyl-4-(3-nitrophenyl)-1,4-dihydropyridine-3,5-dicarboxylate |
| 44 | 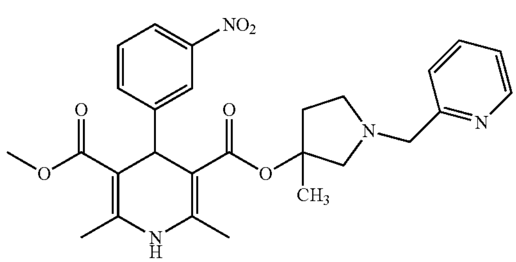 [SMILES: COC(=O)C1=C(C)NC(C)=C(C(=O)OC2(C)CCN(Cc3ccccn3)C2)C1c1cccc([N+](=O)[O-])c1] | 3-[3-methyl-1-(pyrid-2-ylmethyl) pyrrolidin-3-yl] 5-methyl 2,6-dimethyl-4-(3-nitrophenyl)-1,4-dihydropyridine-3,5-dicarboxylate |

| Compound | Structure | Chemical Name |
|---|---|---|
| 45 | 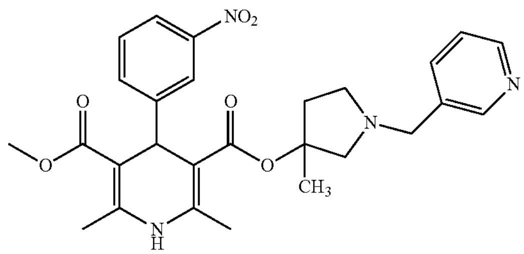 [SMILES: COC(=O)C1=C(C)NC(C)=C(C(=O)OC2(C)CCN(Cc3cccnc3)C2)C1c1cccc([N+](=O)[O-])c1] | 3-[3-methyl-1-(pyrid-3-ylmethyl)pyrrolidin-3-yl] 5-methyl 2,6-dimethyl-4-(3-nitrophenyl)-1,4-dihydropyridine-3,5-dicarboxylate |
| 46 | 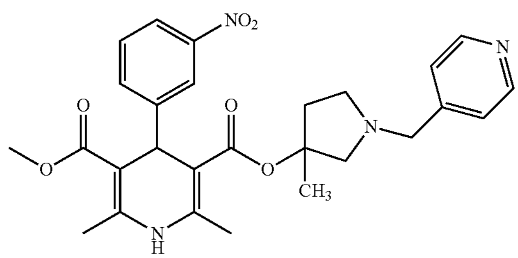 | 3-[3-methyl-1-(pyrid-4-ylmethyl)pyrrolidin-3-yl]) 5-methyl 2,6-dimethyl-4-(3-nitrophenyl)-1,4-dihydropyridine-3,5-dicarboxylate |
| 47 | 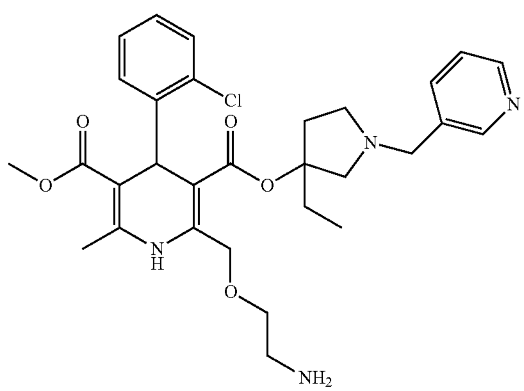 [SMILES: CCC1(OC(=O)C2=C(COCCN)NC(C)=C(C(=O)OC)C2c2ccccc2Cl)CCN(Cc2cccnc2)C1] | 3-[3-ethyl-1-(pyridine-3-ylmethyl)pyrrolidin-3-yl] 5-methyl 2-(2-aminoethoxy)methyl-4-(2-chlorophenyl)-6-methyl-1,4-dihydropyridine-3,5-dicarboxylate |
| 48 | 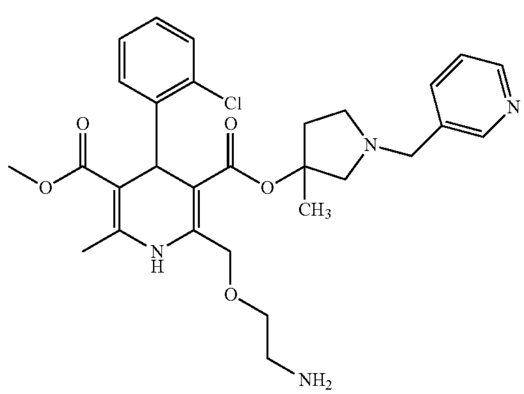 [SMILES: COC(=O)C1=C(C)NC(COCCN)=C(C(=O)OC2(C)CCN(Cc3cccnc3)C2)C1c1ccccc1Cl] | 3-[3-methyl-1-(pyridine-3-ylmethyl)pyrrolidin-3-yl] 5-methyl 2-(2-aminoethoxy)methyl-4-(2-chlorophenyl)-6-methyl-1,4-dihydropyridine-3,5-dicarboxylate |

| Compound | Structure | Chemical Name |
|---|---|---|
| 49 | 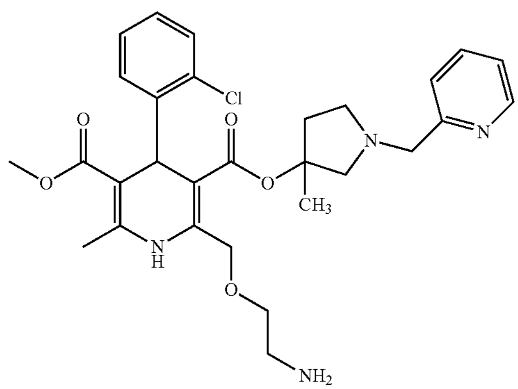 [SMILES: COC(=O)C1=C(C)NC(COCCN)=C(C(=O)OC2(C)CCN(Cc3ccccn3)C2)C1c1ccccc1Cl] | 3-[3-methyl-1-(pyridine-2-ylmethyl)pyrrolidin-3-yl] 5-methyl 2-(2-aminoethoxy)methyl-4-(2-chlorophenyl)-6-methyl-1,4-dihydropyridine-3,5-dicarboxylate |
| 50 | 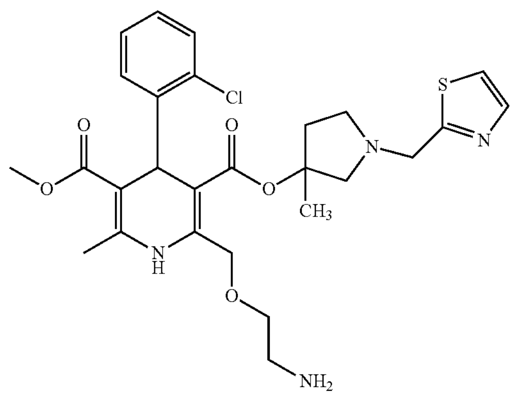 [SMILES: COC(=O)C1=C(C)NC(COCCN)=C(C(=O)OC2(C)CCN(Cc3nccs3)C2)C1c1ccccc1Cl] | 3-[3-methyl-1-(thiazol-2-ylmethyl)pyrrolidin-3-yl] 5-methyl 2-(2-aminoethoxy)methyl-4-(2-chlorophenyl)-6-methyl-1,4-dihydropyridine-3,5-dicarboxylate |
| 52 | 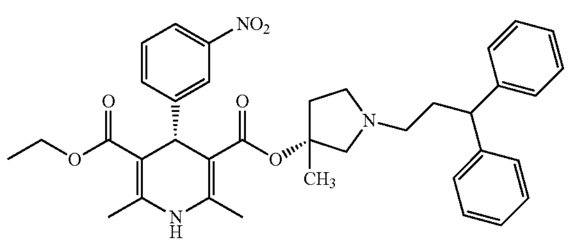 [SMILES: CCOC(=O)C1=C(C)NC(C)=C(C(=O)O[C@]2(C)CCN(CCC(c3ccccc3)c3ccccc3)C2)[C@H]1c1cccc([N+](=O)[O-])c1] | (S)-3-[(R)-1-(3,3-diphenylpropyl)-3-methylpyrrolidin-3-yl] 5-ethyl 2,6-dimethyl-4-(3-nitrophenyl)-1,4-dihydropyridine-3,5-dicarboxylate |
| 53 | 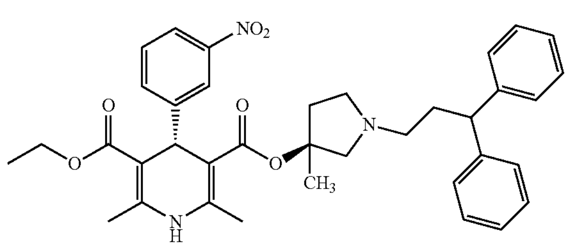 [SMILES: CCOC(=O)C1=C(C)NC(C)=C(C(=O)O[C@@]2(C)CCN(CCC(c3ccccc3)c3ccccc3)C2)[C@H]1c1cccc([N+](=O)[O-])c1] | (S)-3-[(S)-1-(3,3-diphenylpropyl)-3-methylpyrrolidin-3-yl] 5-ethyl 2,6-dimethyl-4-(3-nitrophenyl)-1,4-dihydropyridine-3,5-dicarboxylate |

-continued

| Compound | Structure | Chemical Name |
|---|---|---|
| 56 | 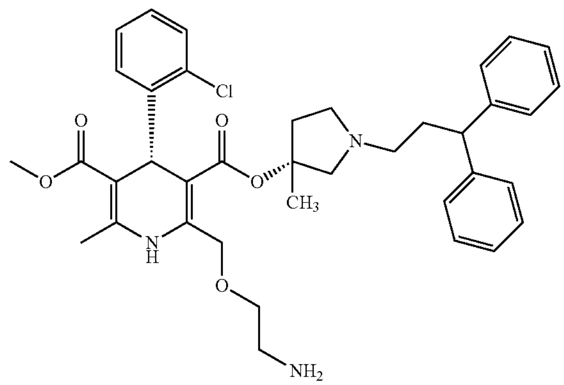 [SMILES: COC(=O)C1=C(C)NC(COCCN)=C(C(=O)O[C@]2(C)CCN(CCC(c3ccccc3)c3ccccc3)C2)[C@H]1c1ccccc1Cl] | (S)-3-[(R)-1-(3,3-diphenylpropyl)-3-methylpyrrolidin-3-yl] 5-methyl 2-(2-aminoethoxy)methyl-4-(2-chlorophenyl)-6-methyl-1,4-dihydropyridine-3,5-dicarboxylate |
| 57 | 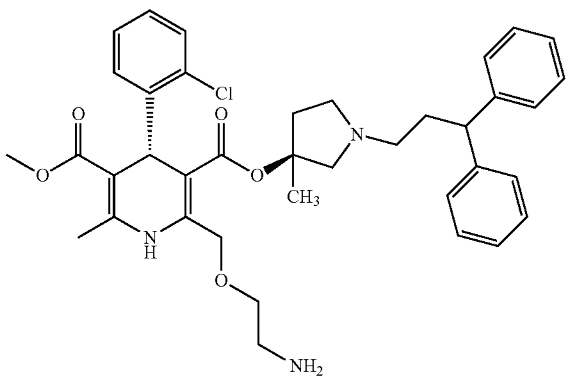 [SMILES: COC(=O)C1=C(C)NC(COCCN)=C(C(=O)O[C@@]2(C)CCN(CCC(c3ccccc3)c3ccccc3)C2)[C@H]1c1ccccc1Cl] | (S)-3-[(S)-1-(3,3-diphenylpropyl)-3-methylpyrrolidin-3-yl] 5-methyl 2-(2-aminoethoxy)methyl-4-(2-chlorophenyl)-6-methyl-1,4-dihydropyridine-3,5-dicarboxylate |
| 58 | 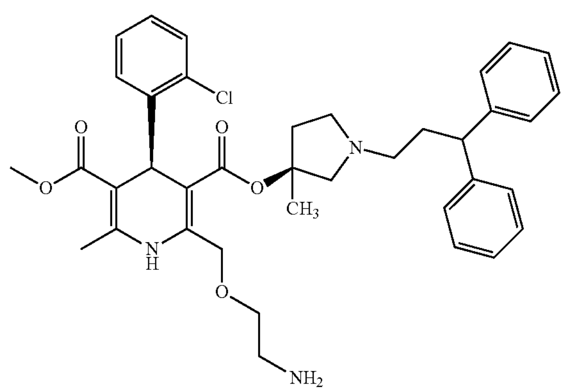 [SMILES: COC(=O)C1=C(C)NC(COCCN)=C(C(=O)O[C@@]2(C)CCN(CCC(c3ccccc3)c3ccccc3)C2)[C@@H]1c1ccccc1Cl] | (R)-3-[(S)-1-(3,3-diphenylpropyl)-3-methylpyrrolidin-3-yl] 5-methyl 2-(2-aminoethoxy)methyl-4-(2-chlorophenyl)-6-methyl-1,4-dihydropyridine-3,5-dicarboxylate |
| 61 | 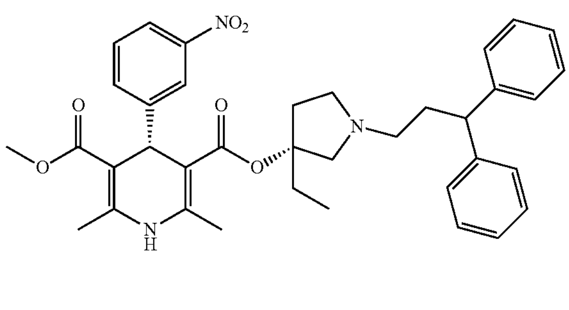 [SMILES: CC[C@@]1(OC(=O)C2=C(C)NC(C)=C(C(=O)OC)[C@@H]2c2cccc([N+](=O)[O-])c2)CCN(CCC(c2ccccc2)c2ccccc2)C1] | (S)-3-[(R)-1-(3,3-diphenylpropyl)-3-ethylpyrrolidin-3-yl] 5-methyl 2,6-dimethyl-4-(3-nitrophenyl)-1,4-dihydropyridine-3,5-dicarboxylate |

| Compound | Structure | Chemical Name |
|---|---|---|
| 62 | 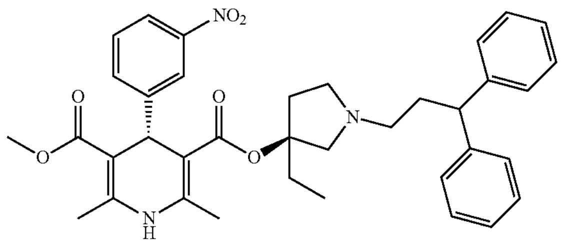 [SMILES: CC[C@]1(OC(=O)C2=C(C)NC(C)=C(C(=O)OC)[C@@H]2c2cccc([N+](=O)[O-])c2)CCN(CCC(c2ccccc2)c2ccccc2)C1] | (S)-3-[(S)-1-(3,3-diphenylpropyl)-3-ethylpyrrolidin-3-yl] 5-methyl 2,6-dimethyl-4-(3-nitrophenyl)-1,4-dihydropyridine-3,5-dicarboxylate |
| 68 | 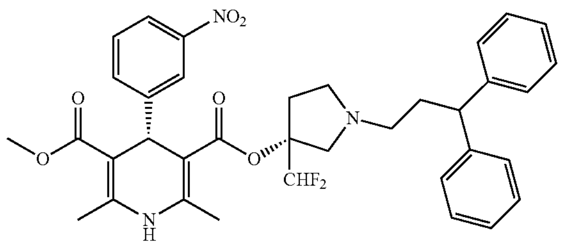 [SMILES: COC(=O)C1=C(C)NC(C)=C(C(=O)O[C@]2(C(F)F)CCN(CCC(c3ccccc3)c3ccccc3)C2)[C@H]1c1cccc([N+](=O)[O-])c1] | (S)-3-[(R)-3-difluoromethyl-1-(3,3-diphenylpropyl)pyrrolidin-3-yl] 5-methyl 2,6-dimethyl-4-(3-nitrophenyl)-1,4-dihydropyridine-3,5-dicarboxylate |
| 69 | 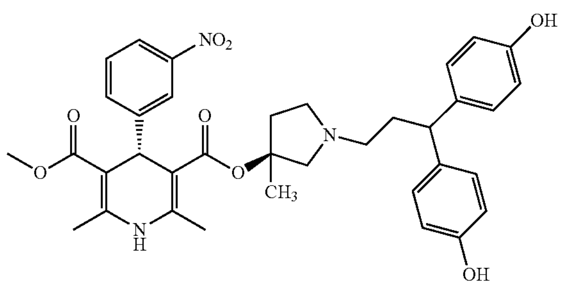 [SMILES: COC(=O)C1=C(C)NC(C)=C(C(=O)O[C@@]2(C)CCN(CCC(c3ccc(O)cc3)c3ccc(O)cc3)C2)[C@H]1c1cccc([N+](=O)[O-])c1] | (S)-3-[(S)-1-(3,3-bis(4-hydroxyphenyl-propyl)-3-methylpyrrolidin-3-yl] 5-methyl 2,6-dimethyl-4-(3-nitrophenyl)-1,4-dihydropyridine-3,5-dicarboxylate |
| 71 | 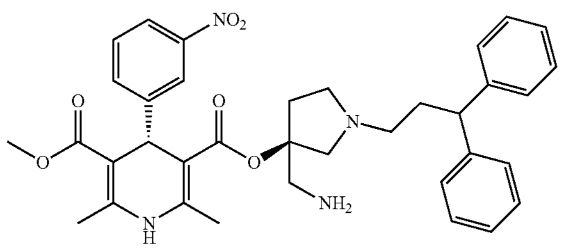 [SMILES: COC(=O)C1=C(C)NC(C)=C(C(=O)O[C@@]2(CN)CCN(CCC(c3ccccc3)c3ccccc3)C2)[C@H]1c1cccc([N+](=O)[O-])c1] | (S)-3-[(R)-3-aminomethyl-1-(3,3-diphenyl-propyl)pyrrolidin-3-yl] 5-methyl 2,6-dimethyl-4-(3-nitrophenyl)-1,4-dihydropyridine-3,5-dicarboxylate |
| 73 | 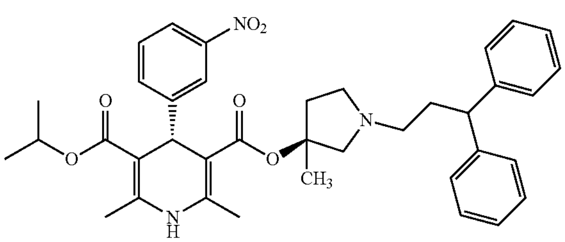 [SMILES: CC1=C(C(=O)OC(C)C)[C@H](c2cccc([N+](=O)[O-])c2)C(C(=O)O[C@@]2(C)CCN(CCC(c3ccccc3)c3ccccc3)C2)=C(C)N1] | (S)-3-[(S)-1-(3,3-diphenylpropyl)-3-methylpyrrolidin-3-yl] 5-isopropyl 2,6-dimethyl-4-(3-nitrophenyl)-1,4-dihydropyridine-3,5-dicarboxylate |
| 75 | 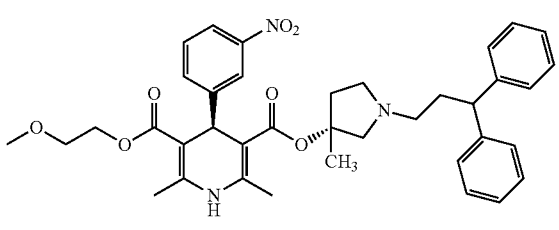 [SMILES: COCCOC(=O)C1=C(C)NC(C)=C(C(=O)O[C@]2(C)CCN(CCC(c3ccccc3)c3ccccc3)C2)[C@@H]1c1cccc([N+](=O)[O-])c1] | (R)-3-[(R)-1-(3,3-diphenylpropyl)-3-methylpyrrolidin-3-yl] 5-(2-methoxyethyl) 2,6-dimethyl-4-(3-nitrophenyl)-1,4-dihydropyridine-3,5-dicarboxylate |

-continued

| Compound | Structure | Chemical Name |
|---|---|---|
| 76 | 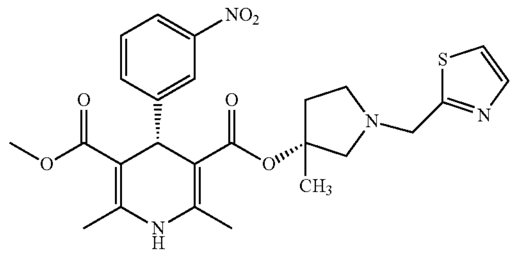 [SMILES: COC(=O)C1=C(C)NC(C)=C(C(=O)O[C@]2(C)CCN(Cc3nccs3)C2)[C@H]1c1cccc([N+](=O)[O-])c1] | (S)-3-[(R)-3-methyl-1-(thiazol-2-ylmethyl)pyrrolidin-3-yl] 5-methyl 2,6-dimethyl-4-(3-nitrophenyl)-1,4-dihydropyridine-3,5-dicarboxylate |
| 77 | 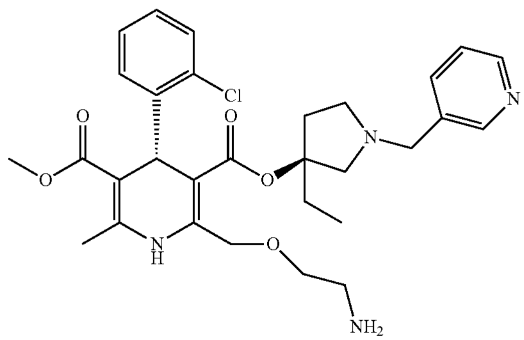 [SMILES: CC[C@]1(OC(=O)C2=C(COCCN)NC(C)=C(C(=O)OC)[C@@H]2c2ccccc2Cl)CCN(Cc2cccnc2)C1] | (S)-3-[(S)-3-ethyl-1-(pyridine-3-ylmethyl)pyrrolidin-3-yl] 5-methyl 2-(2-aminoethoxy)methyl-4-(2-chlorophenyl)-6-methyl-1,4-dihydropyridine-3,5-dicarboxylate |
| 78 | 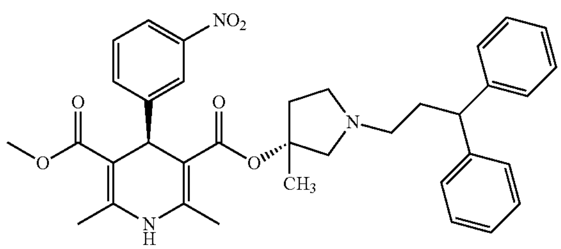 | (R)-3-[(R)-1-(3,3-diphenylpropyl)-3-methylpyrrolidin-3-yl] 5-methyl 2,6-dimethyl-4-(3-nitrophenyl)-1,4-dihydropyridine-3,5-dicarboxylate |
| 79 | 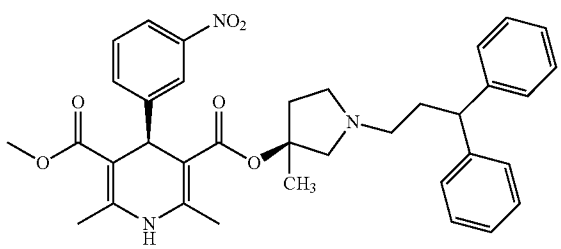 [SMILES: COC(=O)C1=C(C)NC(C)=C(C(=O)O[C@@]2(C)CCN(CCC(c3ccccc3)c3ccccc3)C2)[C@@H]1c1cccc([N+](=O)[O-])c1] | (R)-3-[(S)-1-(3,3-diphenylpropyl)-3-methylpyrrolidin-3-yl] 5-methyl 2,6-dimethyl-4-(3-nitrophenyl)-1,4-dihydropyridine-3,5-dicarboxylate. |

4. The compound of claim 1, a pharmaceutically acceptable salt or a stereoisomer thereof, wherein said compound is selected from

| Compound | Structure | Chemical Name |
|---|---|---|
| 2 | 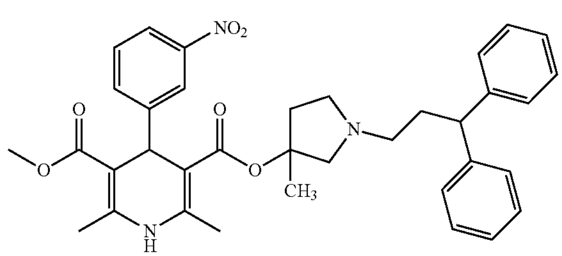 [SMILES: COC(=O)C1=C(C)NC(C)=C(C(=O)OC2(C)CCN(CCC(c3ccccc3)c3ccccc3)C2)C1c1cccc([N+](=O)[O-])c1] | 3-[1-(3,3-diphenylpropyl)-3-methylpyrrolidin-3-yl] 5-methyl 2,6-dimethyl-4-(3-nitrophenyl)-1,4-dihydropyridine-3,5-dicarboxylate |

| Compound | Structure | Chemical Name |
|---|---|---|
| 4 | 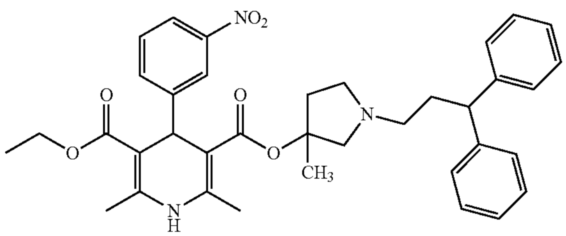 [SMILES: CCOC(=O)C1=C(C)NC(C)=C(C(=O)OC2(C)CCN(CCC(c3ccccc3)c3ccccc3)C2)C1c1cccc([N+](=O)[O-])c1] | 3-[1-(3,3-diphenylpropyl)-3-methylpyrrolidin-3-yl] 5-ethyl 2,6-dimethyl-4-(3-nitrophenyl)-1,4-dihydropyridine-3,5-dicarboxylate |
| 6 | 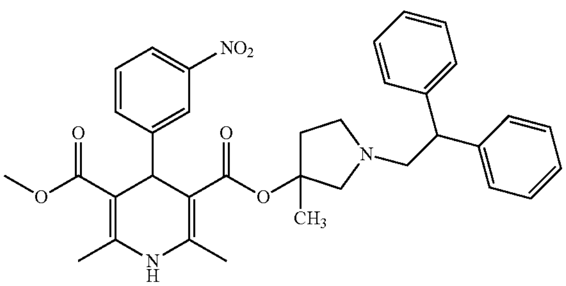 [SMILES: COC(=O)C1=C(C)NC(C)=C(C(=O)OC2(C)CCN(CC(c3ccccc3)c3ccccc3)C2)C1c1cccc([N+](=O)[O-])c1] | 3-[1-(2,2-diphenylethyl)-3-methylpyrrolidin-3-yl] 5-methyl 2,6-dimethyl-4-(3-nitrophenyl)-1,4-dihydropyridine-3,5-dicarboxylate |
| 8 | 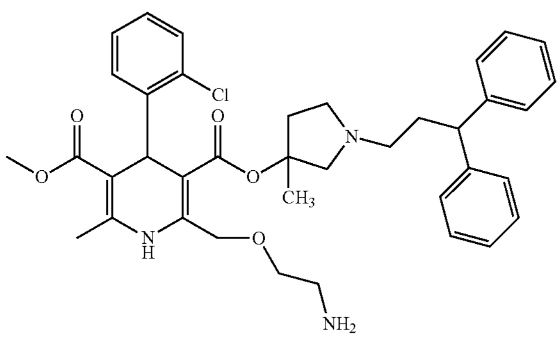 [SMILES: COC(=O)C1=C(C)NC(COCCN)=C(C(=O)OC2(C)CCN(CCC(c3ccccc3)c3ccccc3)C2)C1c1ccccc1Cl] | 3-[1-(3,3-diphenylpropyl)-3-methylpyrrolidin-3-yl] 5-methyl 2-[(2-aminoethoxy)methyl]-4-(2-chlorophenyl)-6-methyl-1,4-dihydropyridine-3,5-dicarboxylate |
| 11 | 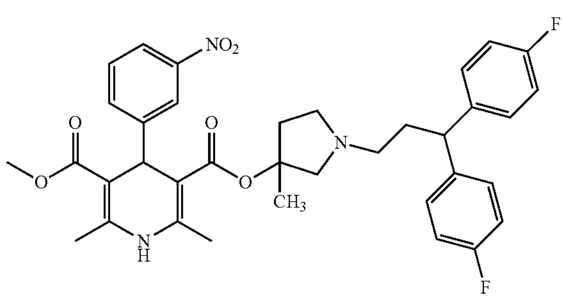 [SMILES: COC(=O)C1=C(C)NC(C)=C(C(=O)OC2(C)CCN(CCC(c3ccc(F)cc3)c3ccc(F)cc3)C2)C1c1cccc([N+](=O)[O-])c1] | 3-[1-(3,3-bis(4-fluorophenyl)propyl)-3-methylpyrrolidin-3-yl] 5-methyl 2,6-dimethyl-4-(3-nitrophenyl)-1,4-dihydropyridine-3,5-dicarboxylate |
| 14 | 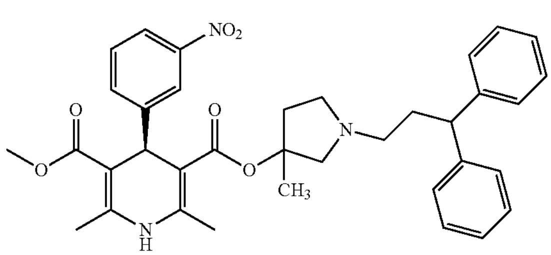 [SMILES: COC(=O)C1=C(C)NC(C)=C(C(=O)OC2(C)CCN(CCC(c3ccccc3)c3ccccc3)C2)[C@@H]1c1cccc([N+](=O)[O-])c1] | (4R)-3-[1-(3,3-diphenylpropyl)-3-methylpyrrolidin-3-yl] 5-methyl 2,6-dimethyl-4-(3-nitrophenyl)-1,4-dihydropyridine-3,5-dicarboxylate |

-continued

| Compound | Structure | Chemical Name |
|---|---|---|
| 15 | 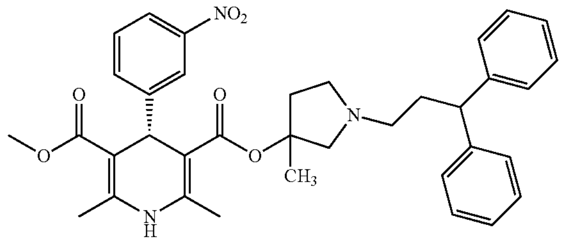 | (4S)-3-[1-(3,3-diphenylpropyl)-3-methylpyrrolidin-3-yl] 5-methyl 2,6-dimethyl-4-(3-nitrophenyl)-1,4-dihydropyridine-3,5-dicarboxylate |
| 16 | 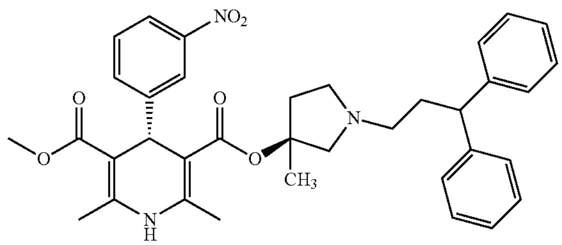 [SMILES: COC(=O)C1=C(C)NC(C)=C(C(=O)O[C@@]2(C)CCN(CCC(c3ccccc3)c3ccccc3)C2)[C@H]1c1cccc([N+](=O)[O-])c1] | (S)-3-[(S)-1-(3,3-diphenylpropyl)-3-methylpyrrolidin-3-yl] 5-methyl 2,6-dimethyl-4-(3-nitrophenyl)-1,4-dihydropyridine-3,5-dicarboxylate |
| 17 | 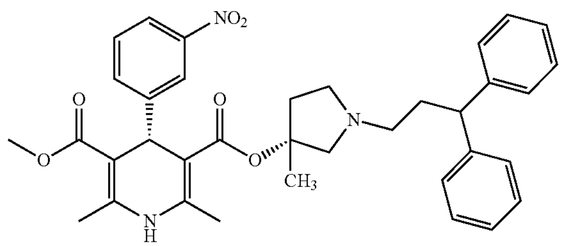 [SMILES: COC(=O)C1=C(C)NC(C)=C(C(=O)O[C@]2(C)CCN(CCC(c3ccccc3)c3ccccc3)C2)[C@H]1c1cccc([N+](=O)[O-])c1] | (S)-3-[(R)-1-(3,3-diphenylpropyl)-3-methylpyrrolidin-3-yl] 5-methyl 2,6-dimethyl-4-(3-nitrophenyl)-1,4-dihydropyridine-3,5-dicarboxylate |
| 18 | 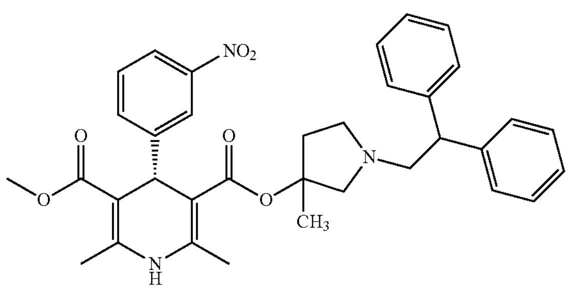 | (4S)-3-[1-(2,2-diphenylethyl)-3-methylpyrrolidin-3-yl] 5-methyl 2,6-dimethyl-4-(3-nitrophenyl)-1,4-dihydropyridine-3,5-dicarboxylate |
| 19 | 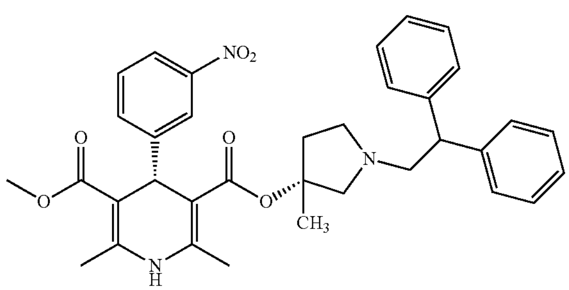 | (S)-3-[(R)-1-(2,2-diphenylethyl)-3-methylpyrrolidin-3-yl] 5-methyl 2,6-dimethyl-4-(3-nitrophenyl)-1,4-dihydropyridine-3,5-dicarboxylate |
| 20 | 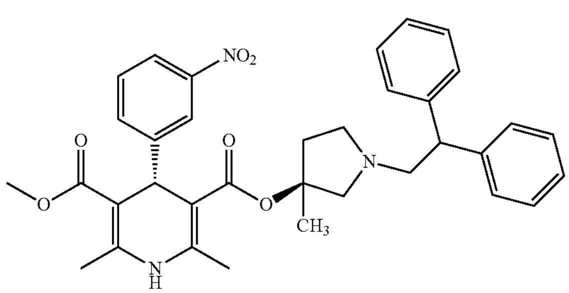 [SMILES: COC(=O)C1=C(C)NC(C)=C(C(=O)O[C@@]2(C)CCN(CC(c3ccccc3)c3ccccc3)C2)[C@H]1c1cccc([N+](=O)[O-])c1] | (S)-3-[(S)-1-(2,2-diphenylethyl)-3-methylpyrrolidin-3-yl] 5-methyl 2,6-dimethyl-4-(3-nitrophenyl)-1,4-dihydropyridine-3,5-dicarboxylate |

| Compound | Structure | Chemical Name |
|---|---|---|
| 27 | 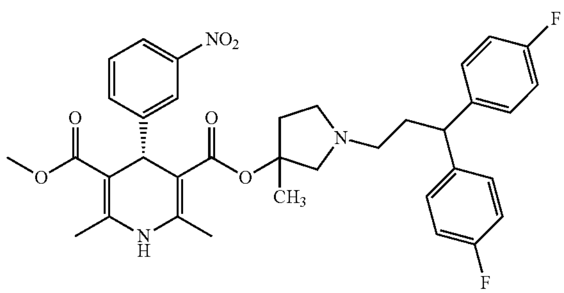 | (4S)-3-[1-(3,3-bis(4-fluorophenyl)propyl)-3-methylpyrrolidin-3-yl] 5-methyl 2,6-dimethyl-4-(3-nitrophenyl)-1,4-dihydropyridine-3,5-dicarboxylate |
| 78 | 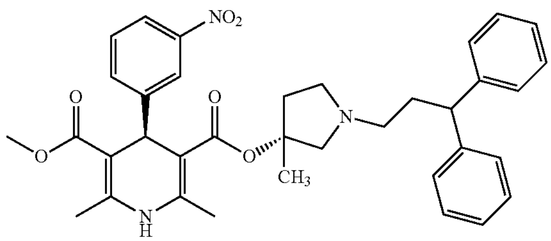 [SMILES: COC(=O)C1=C(C)NC(C)=C(C(=O)O[C@]2(C)CCN(CCC(c3ccccc3)c3ccccc3)C2)[C@@H]1c1cccc([N+](=O)[O-])c1] | (R)-3-[(R)-1-(3,3-diphenylpropyl)-3-methylpyrrolidin-3-yl] 5-methyl 2,6-dimethyl-4-(3-nitrophenyl)-1,4-dihydropyridine-3,5-dicarboxylate |
| 79 | 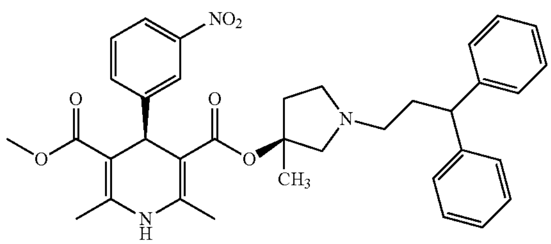 [SMILES: COC(=O)C1=C(C)NC(C)=C(C(=O)O[C@@]2(C)CCN(CCC(c3ccccc3)c3ccccc3)C2)[C@@H]1c1cccc([N+](=O)[O-])c1] | (R)-3-[(S)-1-(3,3-diphenylpropyl)-3-methylpyrrolidin-3-yl] 5-methyl 2,6-dimethyl-4-(3-nitrophenyl)-1,4-dihydropyridine-3,5-dicarboxylate. |

5. A process for preparing the compound of general formula (I) of claim 1, comprising the following steps:

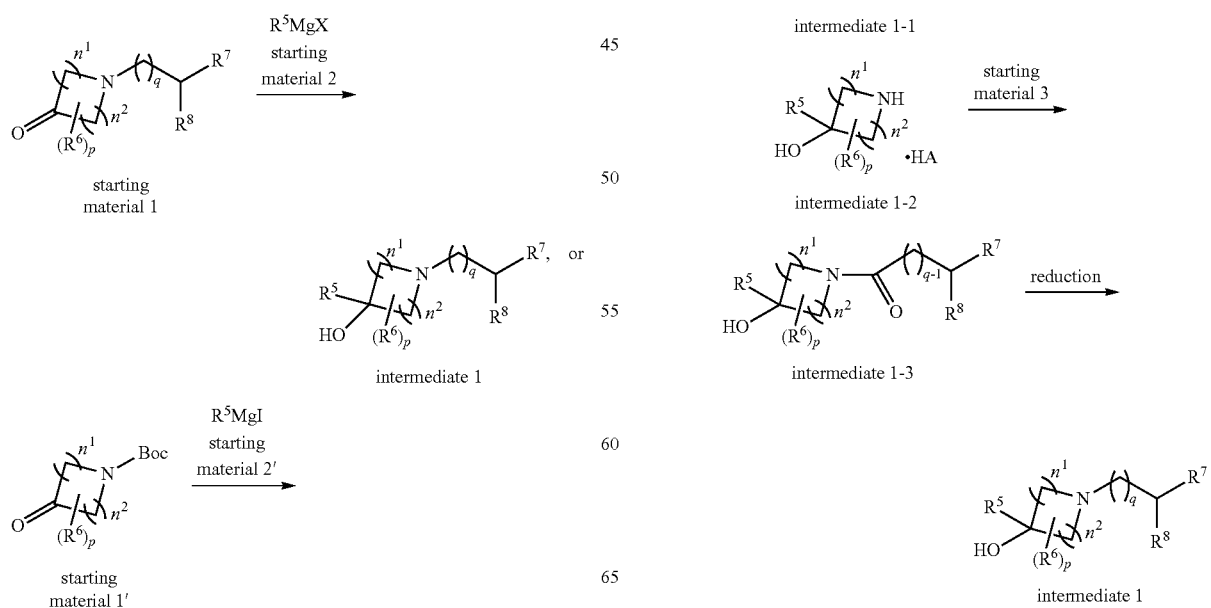

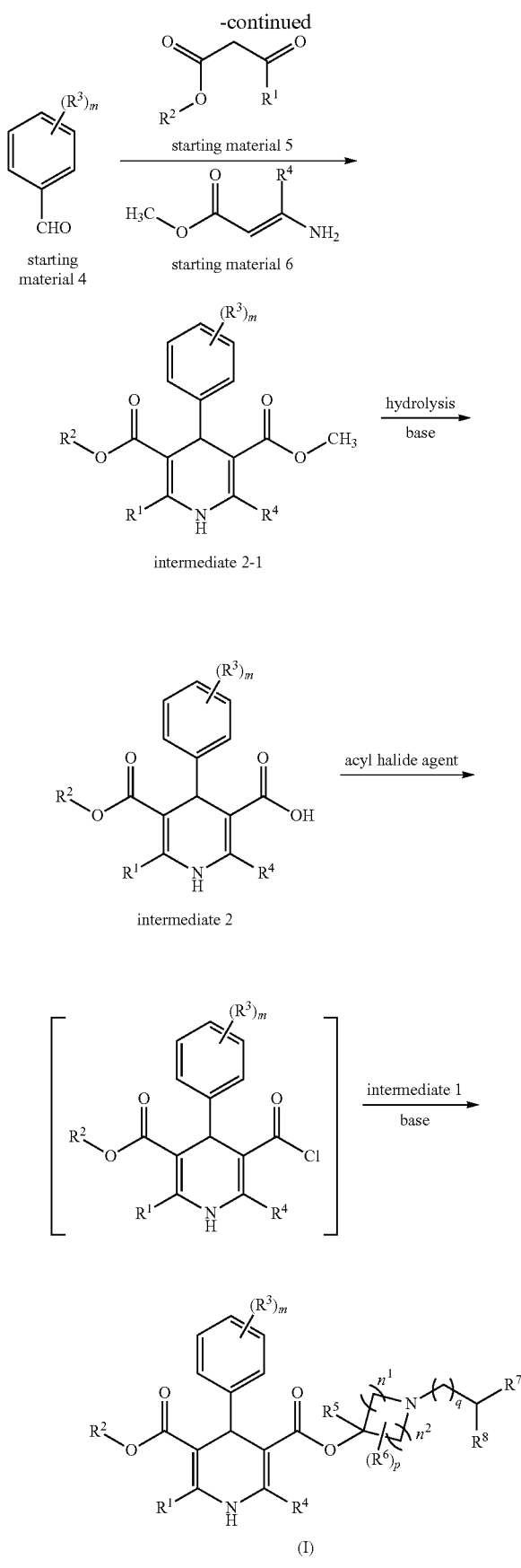

wherein $R^1, R^2, R^3, R^4, R^5, R^6, R^7, R^8, m, n^1, n^2, p$ and $q$ are as defined in claim 1;
starting material 2=$R^5MgX$, wherein X is Br or I;
starting material 2'=$R^5MgI$,
starting material 3=

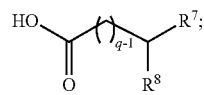

step 1:
starting material 1 and starting material 2 are subjected to a nucleophilic substitution reaction at a low temperature to produce intermediate 1; or
starting material 1' and starting material 2' are subjected to a nucleophilic substitution reaction to produce intermediate 1-1, which is subjected to a salification reaction with an acid HA to produce intermediate 1-2; the resulting intermediate 1-2 and starting material 3 are subjected to a coupling reaction to produce intermediate 1-3; and then intermediate 1-3 is reduced with a reductant to produce intermediate 1;

step 2:
starting material 4, starting material 5 and starting material 6 are subjected to a condensation reaction under reflux in an organic solvent to produce intermediate 2-1, which is hydrolyzed in the presence of a base to produce intermediate 2; and step 3:
intermediate 2 and an acyl halide agent are reacted at a low temperature, and then the resulting material and intermediate 1 are subject to a hydrolyzation reaction under a basic condition at a low temperature to produce the compound of formula (I).

6. A pharmaceutical composition containing a compound of claim 1, a pharmaceutically acceptable salt or a stereoisomer thereof.

7. A pharmaceutical composition containing a compound of claim 2, a pharmaceutically acceptable salt or a stereoisomer thereof.

8. A pharmaceutical composition containing a compound of claim 3, a pharmaceutically acceptable salt or a stereoisomer thereof.

9. A pharmaceutical composition containing a compound of claim 4, a pharmaceutically acceptable salt or a stereoisomer thereof.

10. The pharmaceutical composition of claim 6, further comprising therapeutic agent(s) selected from: angiotensin II antagonists or a pharmaceutically acceptable salt thereof; HMG-Co-A reductase inhibitors or a pharmaceutically acceptable salt thereof; aldosterone receptor antagonists (MRA) or a pharmaceutically acceptable salt thereof; angiotensin converting enzyme/neutral endopeptidase (ACE/NEP) dual inhibitors or a pharmaceutically acceptable salt thereof; antidiabetics; weight-loss drugs; endothelin receptor blockers; CETP inhibitors; Na-K-ATPase membrane pump inhibitors; β-adrenergic receptor inhibitors; α-adrenergic receptor blockers; neutral endopeptidase (NEP) inhibitors and inotropic agents.

11. A pharmaceutical formulation containing a compound of claim 1, a pharmaceutically acceptable salt or a stereoisomer thereof and one or more pharmaceutically acceptable carriers, in any one of pharmaceutically acceptable dosage forms.

12. A method for treating kidney injury, cardiovascular diseases and/or endocrine diseases, comprising the step of administrating a compound of claim 1, a pharmaceutically acceptable salt or a stereoisomer thereof to a mammal in need thereof; wherein said diseases are selected from high blood pressure, heart failure, myocardial infarction, angina pectoris, cardiac hypertrophy, myocarditis, cardiovascular fibrosis, baroreceptor dysfunction, fluid overload and arhythmia, primary/secondary aldosteronism, Addison's disease, Cushing's syndrome and Bartter's syndrome.

13. The pharmaceutical composition of claim 10, wherein the angiotensin II antagonists comprise losartan, valsartan, irbesartan, olmesartan, or candesartan.

14. The pharmaceutical composition of claim 10, wherein the HMG-Co-A reductase inhibitors comprise lovastatin, simvastatin, pravastatin, mevastatin, fluvastatin, atorvastatin, cerivastatin, Rosuvastatin.

15. The pharmaceutical composition of claim 10, wherein the aldosterone receptor antagonists (MRA) comprise spironolactone or eplerenone.

16. The pharmaceutical composition of claim 10, wherein the angiotensin converting enzyme/neutral endopeptidase (ACE/NEP) dual inhibitors comprise captopril, alacepril, enalapril, lisinopril, perindopril, ramipril, quinapril, delapril, cilazapril, benazepril, spirapril, trandolapril, moexipril, imidapril, or fosinopril.

17. The pharmaceutical composition of claim 10, wherein the antidiabetics comprise metformin, glibenclamide, glipizide, glibornuride, gliclazide, gliquidone, sitagliptin, vildagliptin, saxagliptin, alogliptin benzoate, or linagliptin.

18. The pharmaceutical composition of claim 10, wherein the endothelin receptor blockers comprise bosentan.

19. The pharmaceutical composition of claim 10, wherein the β-adrenergic receptor inhibitors comprise metoprolol or carvedilol.

20. The pharmaceutical composition of claim 10, wherein the α-adrenergic receptor blockers comprise prazosin, terazosin, or doxazosin.

21. A compound of one of the following structures:

| Compound | Structure | Chemical Name |
|---|---|---|
| 5 | 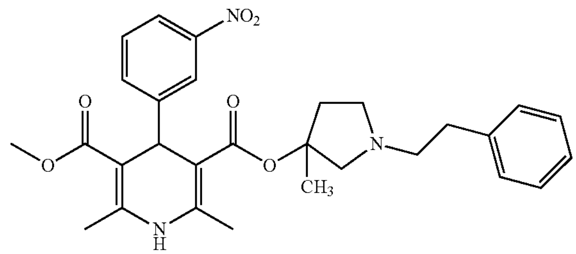 [SMILES: COC(=O)C1=C(C)NC(C)=C(C(=O)OC2(C)CCN(CCc3ccccc3)C2)C1c1cccc([N+](=O)[O-])c1] | 3-(1-phenylethyl-3-methylpyrrolidin-3-yl) 5-methyl 2,6-dimethyl-4-(3-nitrophenyl)-1,4-dihydropyridine-3,5-dicarboxylate; |
| 21 | 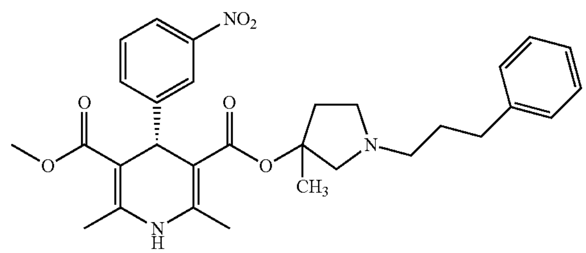 [SMILES: COC(=O)C1=C(C)NC(C)=C(C(=O)OC2(C)CCN(CCCc3ccccc3)C2)[C@H]1c1cccc([N+](=O)[O-])c1] | (4S)-3-[3-methyl-1-(3-phenylpropyl)pyrrolidin-3-yl] 5-methyl 2,6-dimethyl-4-(3-nitrophenyl)-1,4-dihydropyridine-3,5-dicarboxylate; |
| 22 |  | (4S)-3-(3-methyl-1-phenylethylpyrrolidin-3-yl) 5-methyl 2,6-dimethyl-4-(3-nitrophenyl)-1,4-dihydropyridine-3,5-dicarboxylate; | or a pharmaceutically acceptable salt or a stereoisomer thereof.

* * * * *